US007432060B2

(12) United States Patent
Lee

(10) Patent No.: US 7,432,060 B2
(45) Date of Patent: *Oct. 7, 2008

(54) METHODS FOR DIAGNOSIS OF CARDIOVASCULAR DISEASE

(75) Inventor: Richard T. Lee, Weston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/024,607

(22) Filed: Nov. 8, 2001

(65) Prior Publication Data

US 2005/0130136 A1 Jun. 16, 2005

Related U.S. Application Data

(60) Provisional application No. 60/247,457, filed on Nov. 9, 2000.

(51) Int. Cl.
*G01N 33/53* (2006.01)
*C12Q 1/68* (2006.01)

(52) U.S. Cl. ........................................... 435/7.1; 435/6

(58) Field of Classification Search ....................... None
See application file for complete search history.

(56) References Cited

U.S. PATENT DOCUMENTS

| | | | |
|---|---|---|---|
| 5,217,899 A | 6/1993 | Shapiro et al. | |
| 5,348,879 A | 9/1994 | Shapiro et al. | |
| 5,786,163 A | 7/1998 | Hall | |
| 6,288,218 B1 | 9/2001 | Levinson | |
| 6,323,334 B1 | 11/2001 | Kingsbury et al. | |
| 2002/0072674 A1 | 6/2002 | Criton et al. | |
| 2003/0124624 A1 | 7/2003 | Tominaga et al. | |
| 2004/0048286 A1* | 3/2004 | Lee | 435/6 |
| 2006/0216755 A1 | 9/2006 | Lee | |

FOREIGN PATENT DOCUMENTS

| | | |
|---|---|---|
| JP | 6178687 | 6/1994 |
| JP | 7031479 | 2/1995 |
| WO | 98/07754 A1 | 2/1998 |
| WO | WO 09/07754 * | 2/1998 |
| WO | WO 98/38311 * | 9/1998 |
| WO | 99/34217 | 7/1999 |
| WO | 00/35951 A1 | 6/2000 |
| WO | WO 00/35473 A2 | 6/2000 |
| WO | WO 00/73498 A1 | 12/2000 |
| WO | WO 01/70817 A1 | 9/2001 |
| WO | WO 02/38794 A2 | 5/2002 |

OTHER PUBLICATIONS

Saccani S, Polentarutti N, Penton-Rol G, Sims JE, and Mantovani A. 1998. Cytokine. vol. 10(10):773-780.*

Kumar S, Maritsa MN, Griswold, DE, and Young PE. 1997. Biochem. Biophyl Res Comm. vol. 235:474-478.*

Baumgarten G, Knuefermann P, Mann, DL. 2000. Trends Cardiovasc Med. vol. 10(5):216-223.*

GenBank Submission: NIH/NCBI; Accession No. NP_003847, Feb. 3, 2006.*

GenBank Submission: NIH/NCBI; Accession No. NP_003856, Feb. 3, 2006.*

GenBank Submission: NIH/NCBI; Accession No. NP_057316, Feb. 3, 2006.*

GenBank Submission: NIH/NCBI; Accession No. NP_016232, Feb. 3, 2006.*

GenBank Submission: NIH/NCBI; Accession No. D13695, Feb. 3, 1999.*

GenBank Submission: NIH/NCBI; Accession No. Y07519, Mar. 23, 1999.*

GenBank Submission: NIH/NCBI; Accession No. AAA67172, May 23, 1995.*

GenBank Submission: NIH/NCBI; Accession No. D12763, Feb. 1, 2000.*

GenBank Submission: NIH/NCBI; Accession No. E07716, Sep. 29, 1997.*

GenBank Submission: NIH/NCBI; Accession No. AB012701, Aug. 24, 2000.*

GenBank Submission: NIH/NCBI; Accession No. AB029084, Oct. 31, 1999.*

GenBank Submission: NIH/NCBI; Accession No.D12764, May 29, 2002.*

GenBank Submission: NIH/NCBI; Accession No. U04319, May 24, 1995.*

GenBank Submission: NIH/NCBI; Accession No. NM_013037, Apr. 15, 2005.*

GenBank Submission: NIH/NCBI; Accession No. U04317, May 27, 1994.*

GenBank Submission: NIH/NCBI; Accession No. E08652, Nov. 4, 2005.*

GenBank Submission: NIH/NCBI; Accession No. AC007248, Apr. 21, 2005.*

Office Action mailed Mar. 26, 2008 for U.S. Appl. No. 11/411,780 (B0801.70284US01).*

Office Action mailed May 2, 2008 for U.S. Appl. No. 11/435,482 (B0801.70284US00).*

(Continued)

*Primary Examiner*—Robert Landsman
*Assistant Examiner*—Bruce D. Hissong
(74) *Attorney, Agent, or Firm*—Wolf, Greenfield and Sacks, P.C.

(57) ABSTRACT

This invention pertains to methods and compositions for the diagnosis and treatment of cardiovascular conditions. More specifically, the invention relates to isolated molecules that can be used to diagnose and/or treat cardiovascular conditions including cardiac hypertrophy, myocardial infarction, stroke, arteriosclerosis, and heart failure.

16 Claims, 6 Drawing Sheets

OTHER PUBLICATIONS

Kuroiwa et al., Construction of ELISA system to quantify human ST2 protein in sera of patients. Hybridoma. Apr. 2000;19(2):151-9.
Shimpo et al., Serum levels of the interleukin-1 receptor family member ST2 predict mortality and clinical outcome in acute myocardial infarction. Circulation. May 11, 2004;109(18):2186-90.
Weinberg et al., Identification of serum soluble ST2 receptor as a novel heart failure biomarker. Circulation. Feb. 11, 2003;107(5):721-6. Online version published Jan. 13, 2003.
Weinberg et al., Expression and regulation of ST2, an interleukin-1 receptor family member, in cardiomyocytes and myocardial infarction. Circulation. Dec. 3, 2002;106(23):2961-6.
Aukrust et al., Cytokine network in congestive heart failure secondary to ischemic or idiopathic dilated cardiomyopathy. Am J Cardiol. Feb. 1, 1999;83(3):376-82.
Brown, Techniques for mechanical stimulation of cells in vitro: a review. J Biomech. Jan. 2000;33(1):3-14. Review.
Cheng et al., Mechanical strain tightly controls fibroblast growth factor-2 release from cultured human vascular smooth muscle cells. Circ Res. Jan. 1997;80(1):28-36.
Coyle et al., Crucial role of the interleukin 1 receptor family member T1/ST2 in T helper cell type 2-mediated lung mucosal immune responses. J Exp Med. Oct. 4, 1999(7):895-902.
De Keulenaer et al., Identification of IEX-1 as a biomechanically controlled nuclear factor-kappaB target gene that inhibits cardiomyocyte hypertrophy. Circ Res. Apr. 5, 2002;90(6):690-6.
Feng et al., Transcriptional profile of mechanically induced genes in human vascular smooth muscle cells. Circ Res. Dec. 3-17, 1999;85(12):1118-23.
Gwechenberger et al., Cardiac myocytes produce interleukin-6 in culture and in viable border zone of reperfused infarctions. Circulation. Feb. 2, 1999;99(4):546-51.
Hirota et al., Loss of a gp130 cardiac muscle cell survival pathway is a critical event in the onset of heart failure during biomechanical stress. Cell. Apr. 16, 1999;97(2):189-98.
Iwahana et al., Different promoter usage and multiple transcription initiation sites of the interleukin-1 receptor-related human ST2 gene in UT-7 and TM12 cells. Eur J Biochem. Sep. 1999;264(2):397-406.
Izakov et al., Cooperative effects due to calcium binding by troponin and their consequences for contraction and relaxation of cardiac muscle under various conditions of mechanical loading. Circ Res. Nov. 1991;69(5):1171-84.
Joyce et al., Two inhibitors of pro-inflammatory cytokine release, interleukin-10 and interleukin-4, have contrasting effects on release of soluble p75 tumor necrosis factor receptor by cultured monocytes. Eur J Immunol. Nov. 1994;24(11):2699-705.
Löhning et al., T1/ST2 is preferentially expressed on murine Th2 cells, independent of interleukin 4, interleukin 5, and interleukin 10, and important for Th2 effector function. Proc Natl Acad Sci U S A. Jun. 9, 1998;95(12):6930-5.
MacGowan et al., Circulating interleukin-6 in severe heart failure. Am J Cardiol. Apr. 15, 1997;79(8):1128-31.
Mann et al., Stress activated cytokines and the heart. Cytokine Growth Factor Rev. Dec. 1996;7(4):341-54.
Mitcham et al., T1/ST2 signaling establishes it as a member of an expanding interleukin-1 receptor family. J Biol Chem. Mar. 8, 1996;271(10):5777-83.
Murphy et al., Signaling and transcription in T helper development. Annu Rev Immunol. 2000;18:451-94.
Murray et al., Chronic beta-adrenergic stimulation induces myocardial proinflammatory cytokine expression. Circulation. May 23, 2000;101(20):2338-41.
Nichols et al., The influence of 'diastolic' length on the contractility of isolated cat papillary muscle. J Physiol. Apr. 1985;361:269-79.
Ng et al., Diagnosis of heart failure using urinary natriuretic peptides. Clin Sci (Lond). Feb. 2004;106(2):129-33.
Ohtsuka et al., Effect of beta-blockers on circulating levels of inflammatory and anti-inflammatory cytokines in patients with dilated cardiomyopathy. J Am Coll Cardiol. Feb. 2001;37(2):412-7.
O'Neill et al., The IL-1 receptor/toll-like receptor superfamily: crucial receptors for inflammation and host defense. Immunol Today. May 2000;21(5):206-9.
Potter et al., Mutations in the murine fitness 1 gene result in defective hematopoiesis. Blood. Sep. 1, 1997;90(5):1850-7.
Prabhu et al., beta-adrenergic blockade in developing heart failure: effects on myocardial inflammatory cytokines, nitric oxide, and remodeling. Circulation. May 2, 2000;101(17):2103-9.
Pulkki et al., Cytokines and cardiomyocyte death. Ann Med. Aug. 1997;29(4):339-43.
Roig et al., Serum interleukin-6 in congestive heart failure secondary to idiopathic dilated cardiomyopathy. Am J Cardiol. Sep. 1, 1998;82(5):688-90, A8.
Schaffer et al., Device for the application of a dynamic biaxially uniform and isotropic strain to a flexible cell culture membrane. J Orthop Res. Sep. 1994;12(5):709-19.
Sutton et al., Left ventricular remodeling after myocardial infarction: pathophysiology and therapy. Circulation. Jun. 27, 2000;101(25):2981-8.
Tominaga et al., The existence of a growth-specific DNA binding factor for the promoter region of mouse ST2 gene. FEBS Lett. Nov. 14, 1994;354(3):311-4.
Tominaga et al., A putative protein of a growth specific cDNA from BALB/c-3T3 cells is highly similar to the extracellular portion of mouse interleukin 1 receptor. FEBS Lett. Dec. 4, 1989;258(2):301-4.
Townsend et al., T1/ST2-deficient mice demonstrate the importance of T1/ST2 in developing primary T helper cell type 2 responses. J Exp Med. Mar. 20, 2000;191(6):1069-76.
Trehu et al., Phase I trial of interleukin 2 in combination with the soluble tumor necrosis factor receptor p75 IgG chimera. Clin Cancer Res. Aug. 1996;2(8):1341-51.
Tsutamoto et al., Interleukin-6 spillover int he peripheral circulation increases with the severity of heart failure, and the high plasma level of interleukin-6 is an important prognostic predictor in patients with congestive heart failure. J Am Coll Cardiol. Feb. 1998;31(2):391-8.
Vahl et al., Length dependence of calcium- and force-transients in normal and failing human myocardium. J Mol Cell Cardiol. May 1998;30(5):957-66.
Yamamoto et al., Induction of tenascin-C in cardiac myocytes by mechanical deformation. Role of reactive oxygen species. J Biol Chem. Jul. 30, 1999;274(31):21840-6.
Yamamoto et al., Mechanical strain suppresses inducible nitric-oxide synthase in cardiac myocytes. J Biol Chem. May 1998;273(19):11862-6.
Yamamoto et al., Regulation of cardiomyocyte mechanotransduction by the cardiac cycle. Circulation. Mar. 13, 2001;103(10):1459-64.
Yamaoka et al., Anti-inflammatory cytokine profile in human heart failure: behavior of interleukin-10 in association with tumor necrosis factor-alpha. Jpn Cir J. Dec. 1999;63(12):951-6.
Yanagisawa et al., Presence of a novel primary response gene ST2L, encoding a product highly similar to the interleukin 1 receptor type 1. FEBS Lett. Feb. 22, 1993;318(1):83-7.
Yanagisawa et al., The expression of ST2 gene in helper T cells and the binding of ST2 protein to myeloma-derived RPM18226 cells. J Biochem (Tokyo). Jan. 1997;121(1):95-103.
Gutstein et al., Role of inositol 1,4,5-trisphosphate receptors in regulating apoptotic signaling and heart failure. Heart Vessels. 1997;Suppl 12:53-7.
Laine et al., Effect of ryanodine on atrial natriuretic peptide secretion by contracting and quiescent rat atrium. Pflugers Arch. Feb. 1994;426(3-4):276-83.
Tung et al., Influence of stretch on excitation threshold of single frog ventricular cells. Exp Physiol. Mar. 1995;80(2):221-35.
Papapetropoulos A, et al. Nitric oxide synthase inhibitors attenuate transforming-growth-factor-beta 1-stimulated capillary organization in vitro. Am J Pathol. May 1997;150(5):1835-44.
Carter RW, et al. Regulation of ST2L expression on T helper (Th) type 2 cells. Eur. J Immunol. Oct. 2001;31(10):2979-85 Abstract Only.
Chan WL, et al. Human IL-18 receptor and ST2L are stable and selective markers for the respective type 1 and type 2 circulating lymphocytes. J. Immunol. Aug. 1, 2001;16793):1238-44 Abstract Only.
Ohki R et al. Identification of mechanically induced genes in human monocytic cells by DNA microarrays. J. Hypertens., Apr. 2002; 20(4):685-691 Abstract Only.

Tominaga S et al. "Nucleotide sequence of a complementary DNA for human ST2" *Biochim Biophys Acta*. Dec. 29, 1992;1171(2):215-8 Abstract Only.
GenBank Submission; NIH/NCBI; Accession NO. U04319 (printed Aug. 23, 2000) (2 pages).
GenBank Submission; NIH/NCBI; Accession NO. U04317 (printed Aug. 23, 2000) (2 pages).
GenBank Submission; NIH/NCBI; Accession NO. E08652 (printed Aug. 23, 2000) (2 pages).
NCB1 BLASTN 2.2.2 [Dec. 14, 2001], BLAST Results (21 pages).
NCBI BLASTN 2.2.2 [Dec. 14, 2001], BLAST Results (15 pages).
NCBI BLASTN 2.0.14 [Jun. 29, 2000], BLAST Results, Query 2065 letters, (5 pages) printed Aug. 23, 2000.
NCBI BLASTN 2.0.14 Jun. 29, 2000, BLAST Results, 2586 letters, (5 pages) printed Aug. 23, 2000.
NCBI BLASTN 2.0.14 [Jun. 29, 2000], BLAST Results, 2065 letters, (5 pages) printed Aug. 23, 2000.
NCBI BLASTN 2.0.14 Jun. 29, 2000, BLAST Results, 2586 letters, (5 pages) printed Aug. 23, 2000.
Monoclonal Antibody: Anti-Human ST2; Medical & Biological Laboratories Co., Ltd., Aug. 23, 2000 (2 pages).
Millenium Pharmaceuticals, Inc. Millenium Pharmaceuticals Identifies a Key mediator of Allergic Immune Response. Press Release Oct. 4, 1999, 2 pages.
Tang Z, et al. Gene Expression profiling during the transition to failure in TNF-α over-expressing mice demonstrates the development of autoimmune myocarditis. Journal of Molecular and Cellular Cardiology 2004; 36:515-30.
Nakano M, et al. Elevation of Soluble Thrombomodulin Antigen Levels in the Derum and Urine of Streptozotocin-Induced Diabetes Model Rats. Thrombosis Research 2000; 99:83-91.
Hanyu T, et al. Urinary Thrombomodulin in Patients with Rheumatoid Arthritis: Relationship to Disease Subset. 1999; 18:385-9.
Nakano M, et al. Characterization of Soluble Thrombomodulin Fragments in Human Urine. Thromb. Haemost. 1998; 79(2):331-337.
Sims Je, IL-1 and IL-18 Receptors, and Their Extended Family. Current Opinion in Immunology. 2002; 14:117-122.
Oshikawa, K, et al. Elevated Soluble ST2 Protein Levels in Sera od Patients with Asthma with an Acute Exacerbation. Am. J. Respir. Crit. CAre Med. 2001; 164:277-81.
Kuroiwa K, et al., Identification of Human ST2 Protein in the Sera of Patients with Autoimmune Diseases. Biochemical and Biophysical Research Cummunications 2001;284:1104-8.
Onda H, et al. Identification of Genes Differentialll Expressed in Canine Vasospastic Cerebral Arteries After Subarachnoid Hemorrhage. Journal of Cerebral Blood Flow & Metabolism 1999; 19:1279-1288.
Weinberg Eo, et al. Expression and Regulation of ST2, an Interleukin-1 Receptor Family Member, in Cardiomyocytes and Myocardial Infarction Circulation 2002; 106:2961-6; published online Nov. 11, 2002.
GenBank Submission; NIH/NCBI; Accession No. AL117622 (printed Sep. 25, 2007) (2 pages).
GenBank Submission; NIH/NCBI; Accession No. AB022176 (printed Sep. 25, 2007) (2 pages).
GenBank Submission; NIH/NCBI; Accession No. AB024518 (printed Sep. 25, 2007) (2 pages).
GenBank Submission; NIH/NCBI; Accession No. X60184 (printed Sep. 25, 2007) (5 pages).
GenBank Submission; NIH/NCBI; Accession No. E07714 (printed Sep. 25, 2007) (2 pages).
GenBank Submission; NIH/NCBI; Accession No. E07716 (printed Oct. 18, 2005) (2 pages).
GenBank Submission; NIH/NCBI; Accession No. D12763 (printed Oct. 18, 2005) (2 pages).
Aukrust et al., Cytokine network in congestive heart failure secondary to ischemic or idiopathic dilated cardiomyopathy. Am J Cardiol. Feb. 1, 1999;83(3):376-82.
Brown, Techniques for mechanical stimulation of cells in vitro: a review. J Biomech. Jan. 2000;33(1):3-14. Review.
Cheng et al., Mechanical strain tightly controls fibroblast growth factor-2 release from cultured human vascular smooth muscle cells. Circ Res. Jan. 1997;80(1):28-36.
Coyle et al., Crucial role of the interleukin 1 receptor family member T1/ST2 in T helper cell type 2-mediated lung mucosal immune responses. J Exp Med. Oct. 4, 1999(7):895-902.
De Keulenaer et al., Identification of IEX-1 as a biomechanically controlled nuclear factor-kappaB target gene that inhibits cardiomyocyte hypertrophy. Circ Res. Apr. 5, 2002;90(6):690-6.
Feng et al., Transcriptional profile of mechanically induced genes in human vascular smooth muscle cells. Circ Res. Dec. 3-17, 1999;85(12):1118-23.
Gwechenberger et al., Cardiac myocytes produce interleukin-6 in culture and in viable border zone of reperfused infarctions. Circulation. Feb. 2, 1999;99(4):546-51.
Hirota et al., Loss of a gp130 cardiac muscle cell survival pathway is a critical event in the onset of heart failure during biomechanical stress. Cell. Apr. 16, 1999;97(2):189-98.
Iwahana et al., Different promoter usage and multiple transcription initiation sites of the interleukin-1 receptor-related human ST2 gene in UT-7 and TM12 cells. Eur J Biochem. Sep. 1999;264(2):397-406.
Izakov et al., Cooperative effects due to calcium binding by troponin and their consequences for contraction and relaxation of cardiac muscle under various conditions of mechanical loading. Circ Res. Nov. 1991;69(5):1171-84.
Joyce et al., Two inhibitors of pro-inflammatory cytokine release, interleukin-10 and interleukin-4, have contrasting effects on release of soluble p75 tumor necrosis factor receptor by cultured monocytes. Eur J Immunol. Nov. 1994;24(11):2699-705.
Löhning et al., T1/ST2 is preferentially expressed on murine Th2 cells, independent of interleukin 4, interleukin 5, and interleukin 10, and important for Th2 effector function. Proc Natl Acad Sci U S A. Jun. 9, 1998;95(12):6930-5.
MacGowan et al., Circulating interleukin-6 in severe heart failure. Am J Cardiol. Apr. 15, 1997;79(8):1128-31.
Mann et al., Stress activated cytokines and the heart. Cytokine Growth Factor Rev. Dec. 1996;7(4):341-54.
Mitcham et al., T1/ST2 signaling establishes it as a member of an expanding interleukin-1 receptor family. J Biol Chem. Mar. 8, 1996;271(10):5777-83.
Murphy et al., Signaling and transcription in T helper development. Annu Rev Immunol. 2000;18:451-94.
Vidal et al., Prognostic Value of Cytokines and Neurohormones in Server Heart Failure, Rev Esp Cardiol 2002; 55(5):481-6.
Naozaki et al., Soluble Tumor Necrosis Factor Receptors are Elevated in Relation to Severity of Congestive Heart Failure, Jpn Circ J 1997; 61:657-64.
Orus et al., Prognostic Value of Serum Cytokines in Patients with Congestive Heart Failure, J Heart Lung Transplant 2000; 19:419-25.
[No Author Listed] Information Hyperlinked Over Proteins - Symbol ILIRL1. http://www.ihop-net.org/UniPub/iHOP/gismo/94438.html?ORGANISM ID=1.
Albert et al., Prospective study of C-reactive protein, homocysteine, and plasma lipid levels as predictors of sudden cardiac death. Circulation. Jun. 4, 2002;105(22):2595-9.
Auer et al., C-reactive protein and coronary artery disease. Jpn Heart J. Nov. 2002;43(6):607-19.
Feldman et al., C-reactive protein is an independent predictor of mortality in women with HIV-1 infection. J Acquir Immune Defic Syndr. Feb. 1, 2003;32(2):210-4. Abstract Only.
Forssmann et al., The heart is the center of a new endocrine, paracrine, and neuroendocrine system. Arch Histol Cytol. 1989; 52 Suppl:293-315. Abstract Only.
Heeschen et al., Predictive value of C-reactive protein and troponin T in patients with unstable angina: a comparative analysis. Capture Investigators. Chimeric c7E3 AntiPlatelet Therapy in Unstable angina REfractory to standard treatment trial. J Am Coll Cardiol. May 2000;35(6):1535-42. Abstract Only.
Januzzi et al., Utility of amino-terminal pro-brain natriuretic peptide testing for prediction of 1-year mortality in patients with dyspnea treated in the emergency department. Arch. Intern Med. Feb. 13, 2006; 166(3)315-20.
Kida et al., [Pathophysiologic role of natriuretic peptides] Rinsho Byori. Aug. 1989;37(8):875-82.
Lammerding et al., Mechanotransduction in cardiac myocytes. Ann N Y Acad Sci. May 2004;1015:53-70.

Mackenna et al., Role of mechanical factors in modulating cardiac fibroblast function and extracellular matrix synthesis. Cardiovasc Res. May 2000;46(2):257-63.

Mukoyama et al., Augmented secretion of brain natriuretic peptide in acute myocardial infarction. Biochem Biophys Res Commun. Oct. 15, 1991;180(1):431-6. Abstract Only.

Sussman et al., Dance band on the Titanic: biomechanical signaling in cardiac hypertrophy. Circ Res. Nov. 15, 2002;91(10):888-98.

Van Kimmenade et al., Utility of amino-terminal pro-brain natriuretic peptide, galectin-3, and apelin for the evaluation of patients with acute heart failure. J Am Coll Cardiol. Sep. 19, 2006;48(6):1217-24.

Zebrack et al., Usefulness of high-sensitivity C-reactive protein in protein in predicting long-term risk of death or acute myocardial infarction in patients with unstable or stable angina pectoris or acute myocardial infarction. Am J CArdiol. Jan. 15, 2002;89(2):145-9.

* cited by examiner

METHODS FOR DIAGNOSIS OF CARDIOVASCULAR DISEASE

RELATED APPLICATIONS

This application claims priority under 35 U.S.C. §119(e) from Provisional U.S. Patent Application Ser. No. 60/247,457 filed on Nov. 9, 2000, entitled CARDIOVASCULAR DISEASE DIAGNOSTIC AND THERAPEUTIC TARGETS. The contents of the provisional application are hereby expressly incorporated by reference.

GOVERNMENT SUPPORT

This invention was made with government support under grant number HL054759 awarded by The National Institute of Health. The government has certain rights in the invention.

FIELD OF THE INVENTION

This invention relates to methods and compositions for the diagnosis and treatment of cardiovascular conditions. More specifically, the invention relates to isolated molecules that can be used to treat cardiovascular conditions including cardiac hypertrophy, myocardial infarction, stroke, arteriosclerosis, and heart failure.

BACKGROUND OF THE INVENTION

Despite significant advances in therapy, cardiovascular disease remains the single most common cause of morbidity and mortality in the developed world. Thus, prevention and therapy of cardiovascular conditions such as myocardial infarction and stroke is an area of major public health importance. Currently, several risk factors for future cardiovascular disorders have been described and are in wide clinical use in the detection of individuals at high risk. Such screening tests include evaluations of total and HDL cholesterol levels. However, a large number of cardiovascular disorders occur in individuals with apparently low to moderate risk profiles, and ability to identify such patients is limited. Moreover, accumulating data suggests that the beneficial effects of certain preventive and therapeutic treatments for patients at risk for or known to have cardiovascular disorders differs in magnitude among different patient groups. At this time, however, data describing diagnostic tests to determine whether certain therapies can be expected to be more or less effective are lacking.

SUMMARY OF THE INVENTION

This invention provides methods and compositions for the diagnosis and treatment of cardiovascular conditions. More specifically, a number of genes were identified that are upregulated in cardiac cells when the cells are subjected to mechanically-induced deformation. In view of these discoveries, it is believed that the molecules of the present invention can be used to treat vascular and cardiovascular conditions including cardiac hypertrophy, myocardial infarction, stroke, arteriosclerosis, and heart failure.

Additionally, methods for using these molecules in the diagnosis of any of the foregoing vascular and cardiovascular conditions, are also provided.

Furthermore, compositions useful in the preparation of therapeutic preparations for the treatment of the foregoing conditions, are also provided.

The present invention thus involves, in several aspects, polypeptides, isolated nucleic acids encoding those polypeptides, functional modifications and variants of the foregoing, useful fragments of the foregoing, as well as therapeutics and diagnostics relating thereto.

According to one aspect of the invention, a method of diagnosing a condition characterized by aberrant expression of a nucleic acid molecule or an expression product thereof (or of unique fragments of the foregoing molecules thereof), is provided. The method involves contacting a biological sample from a subject with an agent, wherein said agent specifically binds to said nucleic acid molecule, an expression product thereof, or a fragment of an expression product thereof, and measuring the amount of bound agent and determining therefrom if the expression of said nucleic acid molecule or of an expression product thereof is aberrant, aberrant expression being diagnostic of the disorder, wherein the nucleic acid molecule is at least one nucleic acid molecule selected from the group consisting of Fit-1 (SEQ ID NOs: 1 and 2 for Fit-1S; SEQ ID NOs: 3 and 4 for Fit-1M), vacuolar ATPase (SEQ ID NOs: 5 and 6), CD44 (SEQ ID NOs: 7 and 8), Lot-1 (SEQ ID NOs: 9 and 10), AA892598 (SEQ ID NO: 11), and Mrg-1 (SEQ ID NO: 12). In some embodiments, the disorder is a cardiovascular condition selected from the group consisting of myocardial infarction, stroke, arteriosclerosis, and heart failure. In one embodiment, the disorder is cardiac hypertrophy. In certain embodiments, biological samples include biopsy samples, and biological fluids such as blood.

According to still another aspect of the invention, a method for determining a stage (e.g, regression, progression or onset) of a cardiovascular condition in a subject characterized by aberrant expression of a nucleic acid molecule or an expression product thereof (or of unique fragments of the foregoing molecules thereof), is provided. The method involves monitoring a sample from a patient for a parameter selected from the group consisting of (i) a nucleic acid molecule selected from the group consisting of Fit-1, vacuolar ATPase, CD44, Lot-1, AA892598, and Mrg-1 (or a unique fragment thereof), (ii) a polypeptide encoded by the nucleic acid, (iii) a peptide derived from the polypeptide (or of a unique fragment thereof), and (iv) an antibody which selectively binds the polypeptide or peptide (or a unique fragment thereof), as a determination of a stage (e.g., regression, progression or onset) of said cardiovascular condition in the subject. In some embodiments, the sample is a biological fluid or a tissue as described in any of the foregoing embodiments. In certain embodiments, the step of monitoring comprises contacting the sample with a detectable agent selected from the group consisting of (a) an isolated nucleic acid molecule which selectively hybridizes under stringent conditions to the nucleic acid molecule of (i), (b) an antibody which selectively binds the polypeptide of (ii), or the peptide of (iii), and (c) a polypeptide or peptide which binds the antibody of (iv). The antibody, polypeptide, peptide, or nucleic acid can be labeled with a radioactive label or an enzyme. In further embodiments, the method further comprises assaying the sample for the peptide. In still further embodiments, monitoring the sample occurs over a period of time.

According to another aspect of the invention, a kit is provided. The kit comprises a package containing an agent that selectively binds to any of the foregoing isolated nucleic acids (Fit-1, vacuolar ATPase, CD44, Lot-1, AA892598, and Mrg-1), or expression products thereof, and a control for comparing to a measured value of binding of said agent any of the foregoing isolated nucleic acids or expression products thereof. In some embodiments, the control is a predetermined value for comparing to the measured value. In certain embodiments, the control comprises an epitope of the expression product of any of the foregoing isolated nucleic acids.

According to one aspect of the invention, a method for treating a cardiovascular condition, is provided. The method involves administering to a subject in need of such treatment a molecule selected from the group consisting of Fit-1 (alternatively referred to herein as T1/ST2), CD44, Lot-1, AA892598, and Mrg-1, in an amount effective to treat the cardiovascular condition. In certain embodiments, the cardiovascular condition is selected from the group consisting of myocardial infarction, stroke, arteriosclerosis, and heart failure. In one embodiment, the molecule administered is vacuolar ATPase. In some embodiments, the method further comprises co-administering an agent selected from the group consisting of an anti-inflammatory agent, an anti-thrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, or an angiotensin system inhibitor.

According to another aspect of the invention, a method for treating cardiac hypertrophy, is provided. The method involves administering to a subject in need of such treatment an agent that increases expression of a nucleic acid molecule selected from the group consisting of Fit-1, vacuolar ATPase, CD44, Lot-1, AA892598, and Mrg-1, or an expression product thereof, in an amount effective to treat cardiac hypertrophy in the subject.

According to a further aspect of the invention, a method for treating a subject to reduce the risk of a cardiovascular condition developing in the subject, is provided. The method involves administering to a subject that expresses decreased levels of a molecule selected from the group consisting of Fit-1, vacuolar ATPase, CD44, Lot-1, AA892598, and Mrg-1, an agent for reducing the risk of the cardiovascular disorder in an amount effective to lower the risk of the subject developing a future cardiovascular disorder, wherein the agent is an anti-inflammatory agent, an anti-thrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, or an angiotensin system inhibitor, or an agent that increases expression of a molecule selected from the group consisting of Fit-1, vacuolar ATPase, CD44, Lot-1, AA892598, and Mrg-1.

According to one aspect of the invention, a method for identifying a candidate agent useful in the treatment of a cardiovascular condition, is provided. The method involves determining expression of a set of nucleic acid molecules in a cardiac cell or tissue under conditions which, in the absence of a candidate agent, permit a first amount of expression of the set of nucleic acid molecules, wherein the set of nucleic acid molecules comprises at least one nucleic acid molecule selected from the group consisting of Fit-1, vacuolar ATPase, CD44, Lot-1, AA892598, and Mrg-1, contacting the cardiac cell or tissue with the candidate agent, and detecting a test amount of expression of the set of nucleic acid molecules, wherein an increase in the test amount of expression in the presence of the candidate agent relative to the first amount of expression indicates that the candidate agent is useful in the treatment of the cardiovascular condition. In certain embodiments, the cardiovascular condition is selected from the group consisting of cardiac hypertrophy (e.g., maladaptive hypertrophy), myocardial infarction, stroke, arteriosclerosis, and heart failure. In some embodiments, the set of nucleic acid molecules comprises at least two, at least three, at least four, or even at least five nucleic acid molecules, each selected from the group consisting of Fit-1, vacuolar ATPase, CD44, Lot-1, AA892598, and Mrg-1.

According to another aspect of the invention, a pharmaceutical composition is provided. The composition comprises an agent comprising an isolated nucleic acid molecule selected from the group consisting of Fit-1, vacuolar ATPase, CD44, Lot-1, AA892598, and Mrg-1, or an expression product thereof, in a pharmaceutically effective amount to treat a cardiovascular condition, and a pharmaceutically acceptable carrier. In some embodiments, the agent is an expression product of the isolated nucleic acid molecule selected from the group consisting of Fit-1, vacuolar ATPase, CD44, Lot-1, AA892598, and Mrg-1. In certain embodiments, the cardiovascular condition is selected from the group consisting of cardiac hypertrophy, myocardial infarction, stroke, arteriosclerosis, and heart failure.

According to a further aspect of the invention, methods for preparing medicaments useful in the treatment of a cardiovascular condition are also provided.

According to still another aspect of the invention, a solid-phase nucleic acid molecule array, is provided. The array consists essentially of a set of nucleic acid molecules, expression products thereof, or fragments (of either the nucleic acid or the polypeptide molecule) thereof, wherein at least two and as many as all of the nucleic acid molecules selected from the group consisting of Fit-1, vacuolar ATPase, CD44, Lot-1, AA892598, and Mrg-1 (including expression products thereof, or fragments thereof), are fixed to a solid substrate. In some embodiments, the solid-phase array further comprises at least one control nucleic acid molecule. In certain embodiments, the set of nucleic acid molecules comprises at least three, at least four, or even at least five nucleic acid molecules, each selected from the group consisting of Fit-1, vacuolar ATPase, CD44, Lot-1, AA892598, and Mrg-1. In preferred embodiments, the set of nucleic acid molecules comprises a maximum number of 100 different nucleic acid molecules. In important embodiments, the set of nucleic acid molecules comprises a maximum number of 10 different nucleic acid molecules.

In certain embodiments, the solid substrate includes a material selected from the group consisting of glass, silica, aluminosilicates, borosilicates, metal oxides such as alumina and nickel oxide, various clays, nitrocellulose, and nylon. Preferably the substrate is glass. In some embodiments, the nucleic acid molecules are fixed to the solid substrate by covalent bonding.

These and other objects of the invention will be described in further detail in connection with the detailed description of the invention.

BRIEF DESCRIPTION OF THE SEQUENCES

SEQ ID NO:1 is the nucleotide sequence of the rat Fit-1S cDNA.

SEQ ID NO:2 is the predicted amino acid sequence of the translation product of rat Fit-1S cDNA (SEQ ID NO:1).

SEQ ID NO:3 is the nucleotide sequence of the rat Fit-1M cDNA.

SEQ ID NO:4 is the predicted amino acid sequence of the translation product of the rat Fit-1M cDNA (SEQ ID NO:3).

SEQ ID NO:5 is the nucleotide sequence of the rat vacuolar ATPase cDNA (GenBank Acc. No. Y12635).

SEQ ID NO:6 is the predicted amino acid sequence of the translation product of the rat vacuolar ATPase cDNA (SEQ ID NO:5).

SEQ ID NO:7 is the nucleotide sequence of the rat glycoprotein CD44 cDNA (GenBank Acc. No. M61875).

SEQ ID NO:8 is the predicted amino acid sequence of the translation product of the rat glycoprotein CD44 cDNA (SEQ ID NO:7).

SEQ ID NO:9 is the nucleotide sequence of the rat Lot-1 cDNA (GenBank Acc. No. U72620).

SEQ ID NO:10 is the predicted amino acid sequence of the translation product of the rat Lot-1 cDNA (SEQ ID NO:9).

SEQ ID NO:11 is the nucleotide sequence of the rat AA892598 (EST196401) cDNA.

SEQ ID NO:12 is the nucleotide sequence of the rat Mrg-1 cDNA (GenBank Acc. No. AA900476).

SEQ ID NO:13 is the nucleotide sequence of the mouse ST2 cDNA (GenBank Acc. No. Y07519).

SEQ ID NO:14 is the nucleotide sequence of the mouse ST2L cDNA (GenBank Acc. No. D13695).

SEQ ID NO:15 is the nucleotide sequence of the bovine vacuolar H+-ATPase cDNA (GenBank Acc. No. M88690).

SEQ ID NO:16 is the nucleotide sequence of the human vacuolar H+-ATPase cDNA (GenBank Acc. No. NM_001693).

SEQ ID NO:17 is the nucleotide sequence of the mouse vacuolar H+-ATPase cDNA (GenBank Acc. No. NM_007509).

SEQ ID NO:18 is the nucleotide sequence of the human vacuolar H+-ATPase cDNA (56,000 subunit -HO57) (GenBank Acc. No. L35249).

SEQ ID NO:19 is the nucleotide sequence of the human vacuolar H+-ATPase cDNA (B subunit) (GenBank Acc. No. M60346).

SEQ ID NO:20 is the nucleotide sequence of the bovine vacuolar H+-ATPase cDNA (B subunit) (GenBank Acc. No. M83131).

SEQ ID NO:21 is the nucleotide sequence of the gallus vacuolar H+-ATPase cDNA (GenBank Acc. No. U61724).

SEQ ID NO:22 is the nucleotide sequence of the human CD44R cDNA (GenBank Acc. No. X56794).

SEQ ID NO:23 is the nucleotide sequence of the human CD44 cDNA (GenBank Acc. No. U40373).

SEQ ID NO:24 is the nucleotide sequence of the mouse CD44 cDNA (GenBank Acc. No. M27129).

SEQ ID NO:25 is the nucleotide sequence of the hamster CD44 cDNA (GenBank Acc. No. M33827).

SEQ ID NO:26 is the nucleotide sequence of the human LOT1 cDNA (GenBank Acc. No. U72621).

SEQ ID NO:27 is the nucleotide sequence of the human ZAC zinc finger protein cDNA (GenBank Acc. No. AJ006354).

SEQ ID NO:28 is the nucleotide sequence of the mouse ZAC1 zinc finger protein cDNA (GenBank Acc. No. AF147785).

SEQ ID NO:29 is the nucleotide sequence having GenBank Acc. No. AF191918.1.

SEQ ID NO:30 is the nucleotide sequence of the human putative nucleotide binding protein, estradiol-induced (E21G3) cDNA (GenBank Acc. No. NM_014366).

SEQ ID NO:31 is the nucleotide sequence of the mouse mrg-1 cDNA (GenBank Acc. No. Y15163).

SEQ ID NO:32 is the nucleotide sequence of the human p35srj cDNA (GenBank Acc. No. AF129290).

SEQ ID NO:33 is the nucleotide sequence of the human p35srj (mrg-1) cDNA (GenBank Acc. No. AF109161).

DETAILED DESCRIPTION OF THE INVENTION

Figure 1:
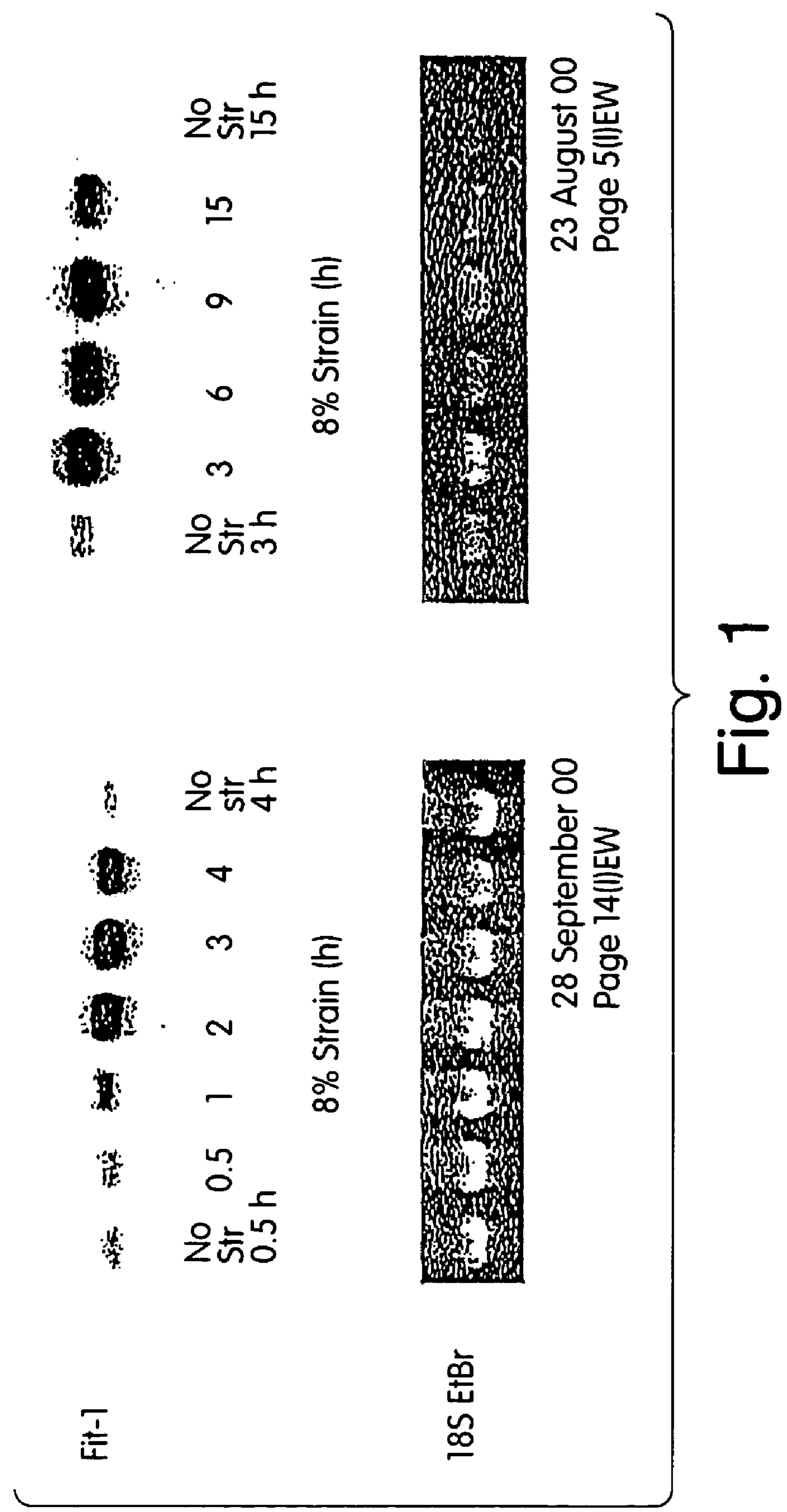
FIG. 1 depicts by a Northern Blot the effects of 8% cyclic mechanical strain on the expression of Fit-1 in cultured cardiac myocytes over the course of time.

The invention involves the discovery of a number of genes that are upregulated in cardiac cells when the cells are subjected to a mechanically-induced strain deformation. In view of this discovery, it is believed that the molecules of the present invention can be used to treat cardiovascular conditions including cardiac hypertrophy, myocardial infarction, stroke, arteriosclerosis, and/or heart failure.

Additionally, methods for using these molecules in the diagnosis of any of the foregoing cardiovascular conditions, are also provided.

Furthermore, compositions useful in the preparation of therapeutic preparations for the treatment of the foregoing conditions, are also provided.

"Upregulated," as used herein, refers to increased expression of a gene and/or its encoded polypeptide. "Increased expression" refers to increasing (i.e., to a detectable extent)

replication, transcription, and/or translation of any of the nucleic acids of the invention (Fit-1, vacuolar ATPase, CD44, Lot-1, AA892598, and Mrg-1), since upregulation of any of these processes results in concentration/amount increase of the polypeptide encoded by the gene (nucleic acid). Conversely, "downregulation," or "decreased expression" as used herein, refers to decreased expression of a gene and/or its encoded polypeptide. The upregulation or downregulation of gene expression can be directly determined by detecting an increase or decrease, respectively, in the level of mRNA for the gene, or the level of protein expression of the gene-encoded polypeptide, using any suitable means known to the art, such as nucleic acid hybridization or antibody detection methods, respectively, and in comparison to controls.

A "cardiac cell", as used herein, refers to a cardiomyocyte.

A "molecule," as used herein, embraces both "nucleic acids" and "polypeptides."

"Expression," as used herein, refers to nucleic acid and/or polypeptide expression.

As used herein, a "subject" is a mammal or a non-human mammal. In all embodiments human nucleic acids, polypeptides, and human subjects are preferred. Although only rat sequences are exemplified in the Sequence Listing and the Examples section, it is believed that the results obtained using such compositions are predictive of the results that may be obtained using homologous human sequences.

In general human homologs and alleles typically will share at least 80% nucleotide identity and/or at least 85% amino acid identity to the characterized rat sequences of the invention. In further instances, human homologs and alleles typically will share at least 90%, 95%, or even 99% nucleotide identity and/or at least 95%, 98%, or even 99% amino acid identity to the characterized rat sequences, respectively. The homology can be calculated using various, publicly available software tools developed by NCBI (Bethesda, Md.). Exemplary tools include the heuristic algorithm of Altschul S F, et al., (*J Mol Biol,* 1990, 215:403-410), also known as BLAST. Pairwise and ClustalW alignments (BLOSUM30 matrix setting) as well as Kyte-Doolittle hydropathic analysis can be obtained using public (EMBL, Heidelberg, Germany) and commercial (e.g., the MacVector sequence analysis software from Oxford Molecular Group/Genetics Computer Group, Madison, Wis., Accelrys, Inc., San Diego, Calif.). Watson-Crick complements of the foregoing nucleic acids also are embraced by the invention.

In screening for human related genes, such as homologs and alleles of the rat sequences described elsewhere herein, a Southern blot may be performed using stringent conditions, together with a probe. The term "stringent conditions" as used herein refers to parameters with which the art is familiar. Nucleic acid hybridization parameters may be found in references which compile such methods, e.g. *Molecular Cloning. A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. For example, stringent conditions may refer to hybridizaotn at 65° C. in 6×SSC. Alternatively, stringent conditions, as used herein, may refer, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetra acetic acid. After hybridization, the membrane upon which the DNA is transferred is washed at 2×SSC at room temperature and then at 0.1×SSC/0.1×SDS at temperatures up to 68° C. In a further example, an alternative to the use of an aqueous hybridization solution is the use of a formamide hybridization solution. Stringent hybridization conditions can thus be achieved using, for example, a 50% formamide solution and 42° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of human homologs and alleles of the rat nucleic acids of the invention. The skilled artisan also is familiar with the methodology for screening cells and libraries for expression of such molecules which then are routinely isolated, followed by isolation of the pertinent nucleic acid molecule and sequencing.

Given the teachings herein of full-length rat cDNA clones, other mammalian sequences such as the human (mouse, bovine, etc.) cDNAs corresponding to the related rat nucleic acids can be isolated from cDNA libraries using standard colony hybridization techniques, or can be identified using a homology search, for example, in GenBank using any of the algorithms described elsewhere herein. For example, sequences with GenBank Accession numbers Y07519.1 (SEQ ID NO:13) and D13695.1 (SEQ ID NO:14) for Fit-1 homologs), M88690.1 (SEQ ID NO:15), NM_001693.1 (SEQ ID NO:16), NM_007509.1 (SEQ ID NO:17), L35249.1 (SEQ ID NO:18), M60346.1 (SEQ ID NO:19), M83131.1 (SEQ ID NO:20 and U61724.1 (SEQ ID NO:21) for vacuolar ATPase homologs), X56794.1 (SEQ ID NO:22), U40373.1 (SEQ ID NO:23), M27129.1 (SEQ ID NO:24), and M33827.1 (SEQ ID NO:25) for CD44 homologs), U72621.3 (SEQ ID NO:26), AJ006354.1 (SEQ ID NO:27), and AF147785.1 (SEQ ID NO:28) for Lot-1 homologs), AF191918.1 (SEQ ID NO:29) and NM_014366.1 (SEQ ID NO:30) for AA892598 homologs), and Y15163.1 (SEQ ID NO:31), AF129290.1 (SEQ ID NO:32), and AF109161.1 (SEQ ID NO:33) for Mrg-1 homologs), can be used interchangeably with the homologous rat sequences of the invention, in all aspects of the invention without departing from the essence of the invention.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulated by recombinant DNA techniques well known in the art. Thus, a nucleotide sequence contained in a vector in which 5' and 3' restriction sites are known or for which polymerase chain reaction (PCR) primer sequences have been disclosed is considered isolated, but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulated by standard techniques known to those of ordinary skill in the art.

According to the invention, expression of any of the foregoing nucleic acids (i.e., Fit-1, vacuolar ATPase, CD44, Lot-1, AA892598, and Mrg-1), uncluding unique fragments of the foregoing, can be determined using different methodologies. A "unique fragment," as used herein, with respect to a nucleic acid is one that is a "signature" for the larger nucleic acid. For example, the unique fragment is long enough to assure that its precise sequence is not found in molecules within the human genome outside of the sequence for each nucleic acid defined above (Fit-1, vacuolar ATPase, CD44, Lot-1, AA892598, and Mrg-1, including their human alleles). Those of ordinary skill in the art may apply no more than routine procedures to determine if a fragment is unique within the human genome. Unique fragments, however, exclude fragments completely composed of nucleotide sequences previously published as of the filing date of this application.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for other uses such as PCR. Unique fragments also can be used to produce fusion proteins for generating antibodies, or determining binding of the polypeptide fragments, or for generating immunoassay components. Likewise, unique fragments can be employed to produce nonfused fragments of, for example, the Fit-1, vacuolar ATPase, CD44, Lot-1, AA892598, and Mrg-1 polypeptides, useful, for example, in the preparation of antibodies, immunoassays or therapeutic applications. Unique fragments further can be used as antisense molecules to inhibit the expression of the foregoing nucleic acids and polypeptides respectively.

As will be recognized by those skilled in the art, the size of the unique fragment will depend upon its conservancy in the genetic code. Thus, some regions of SEQ ID NOs: 1, 3, 5, 7, 9, 11 and 12, and complements will require longer segments to be unique while others will require only short segments, typically between 12 and 32 nucleotides long (e.g., 12, 13, 14, 15, 16, 17, 18, 19, 20, 21, 22, 23, 24, 25, 26, 27, 28, 29, 30, 31 and 32 bases) or more, up to the entire length of each of the disclosed sequences. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, (provided the sequence is unique as described above). For example, virtually any segment of the region of SEQ ID NO:1 beginning at nucleotide 1 and ending at nucleotide 2586, or SEQ ID NO:3 beginning at nucleotide 1 and ending at nucleotide 2065, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, (iii) for sequencing, (iv) as a therapeutic, etc.

In certain aspects, the invention embraces antisense oligonucleotides that selectively bind to a nucleic acid molecule encoding a polypeptide, to decrease the polypeptide's activity.

As used herein, the terms "antisense molecules," "antisense oligonucleotide," and "antisense" describe an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of an antisense oligonucleotide and its degree of complementarity with its target will depend upon the specific target selected, including the sequence of the target and the particular bases which comprise that sequence. It is preferred that an antisense oligonucleotide be constructed and arranged so as to bind selectively with a target under physiological conditions, i.e., to hybridize substantially more to the target sequence than to any other sequence in the target cell under physiological conditions. Based upon SEQ ID NOs: 1, 3, 5, 7, 9, 11 and 12, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med,* 1995, 1(11):1116-1118; *Nat. Biotech.,* 1996, 14:840-844). Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5): 439-457, 1994) and at which proteins are not expected to bind. Finally, although, SEQ ID NOs: 1, 3, 5, 7, 9, 11 and 12 disclose cDNA sequences, one of ordinary skill in the art may easily derive the genomic DNA corresponding to the foregoing sequences. Thus, the present invention also provides for antisense oligonucleotides which are complementary to the genomic DNA corresponding to SEQ ID NOs: 1, 3, 5, 7, 9, 11 and 12. Similarly, antisense to allelic or homologous human cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified"

oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose in place of ribose. The present invention, thus, contemplates pharmaceutical preparations containing modified antisense molecules that are complementary to and hybridizable with, under physiological conditions, nucleic acids encoding the polypeptides with SEQ ID NOs: 2, 4, 6, 8, and/or 10, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves expression vectors coding for proteins encoded by the nucleic acids corresponding to SEQ ID NOs: 1, 3, 5, 7, 9, 11 and/or 12, fragments and variants thereof, and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as *Escherichia coli* and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will often include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is disclosed by Warnier et al., in intradermal injection in mice for immunization against P1A (*Int. J. Cancer,* 67:303-310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described SEQ ID NOs: 1, 3, 5, 7, 9, 11 and/or 12 cDNA sequence-containing expression vectors, to transfect host cells and cell lines, be these prokaryotic (e.g., *Escherichia coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells.

The invention also provides isolated polypeptides (including whole proteins and partial proteins), encoded by the foregoing nucleic acids (SEQ ID NOs: 1, 3, 5, 7, 9, 11 and 12), and include the polypeptides of SEQ ID NOs: 2, 4, 6, 8, and/or 10, and unique fragments thereof. Such polypeptides are useful, for example, alone or as part of fusion proteins to generate antibodies, as components of an immunoassay, etc. Polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment for each of the foregoing polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of a polypeptide will require longer segments to be unique while others will require only short segments, typically between 5 and 12 amino acids (e.g. 5, 6, 7, 8, 9, 10, 11 and 12 amino acids long or more, including each integer up to the full length of each polypeptide).

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, interaction with other molecules, etc. One important activity is the ability to act as a signature for identifying the polypeptide. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the polypeptides described above. As used herein, a "variant" of a polypeptide is a polypeptide which contains one or more modifications to the primary amino acid sequence of a natural (e.g., "wild-type": a polypeptide with an amino acid sequence selected from the group consisting of SEQ ID NO: 2, 4, 6, 8, and 10) polypeptide. Modifications which create a polypeptide variant are typically made to the nucleic acid which encodes the polypeptide, and can include deletions, point mutations, truncations, amino acid substitutions and addition of amino acids or non-amino acid moieties to: (1) reduce or eliminate an activity of a polypeptide; (2) enhance a property of a polypeptide, such as protein stability in an expression system or the stability of protein-ligand binding; (3) provide a novel activity or property to a polypeptide, such as addition of an antigenic epitope or addition of a detectable moiety; or (4) to provide equivalent or better binding to a polypeptide receptor or other molecule. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the polypeptide's amino acid sequence. One of skill in the art will be familiar with methods for predicting the effect on protein conformation of a change in protein sequence, and can thus "design" a variant polypeptide according to known methods. One example of such a method is described by Dahiyat and Mayo in *Science* 278:82-87, 1997, whereby proteins can be designed de novo. The method can be applied to a known protein to vary only a portion of the polypeptide sequence. By applying the computational methods of Dahiyat and Mayo, specific variants of any of the foregoing polypeptides can be proposed and tested to determine whether the variant retains a desired conformation.

Variants can include polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encodes a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *Escherichia coli*, are well known to those of ordinary skill in the art. Still other mutations can be made to the noncoding sequences of a gene or cDNA clone to enhance expression of the polypeptide.

The skilled artisan will realize that conservative amino acid substitutions may be made in any of the foregoing polypeptides to provide functionally equivalent variants of the foregoing polypeptides, i.e., the variants retain the functional capabilities of each polypeptide. As used herein, a "conservative amino acid substitution" refers to an amino acid substitution which does not significantly alter the the tertiary structure and/or activity of the polypeptide. Variants can be prepared according to methods for altering polypeptide sequence known to one of ordinary skill in the art, and include those that are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of polypeptides, i.e., variants of polypeptides which retain the function of the natural ("wild-type") polypeptides, are contemplated by the invention. Conservative amino acid substitutions in the amino acid sequence of polypeptides to produce functionally equivalent variants of each polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide. The activity of functionally equivalent fragments of polypeptides can be tested by cloning the gene encoding the altered polypeptide into a bacterial or mammalian expression vector, introducing the vector into an appropriate host cell, expressing the altered polypeptide, and testing for a functional capability of the polypeptides as disclosed herein.

The invention as described herein has a number of uses, some of which are described elsewhere herein. First, the invention permits isolation of polypeptides. A variety of methodologies well-known to the skilled artisan can be utilized to obtain isolated molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptides. Those skilled in the art also can readily follow known methods for isolating polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and use standard mutagenesis techniques to create one or more dominant negative variant polypeptides. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected activity and/or for retention of such an activity. Other similar methods for creating and testing dominant negative variants of a protein will be apparent to one of ordinary skill in the art.

The isolation of the cDNAs of the invention also makes it possible for the artisan to diagnose a disorder characterized by an aberrant expression of any of the foregoing cDNAs. These methods involve determining expression of each of the identified nucleic acids, and/or polypeptides derived therefrom. In the former situation, such determinations can be carried out via any standard nucleic acid determination assay, including the polymerase chain reaction, or assaying with labeled hybridization probes as exemplified below. In the latter situation, such determination can be carried out via any standard immunological assay using, for example, antibodies which bind to the secreted protein.

The invention also embraces isolated peptide binding agents which, for example, can be antibodies or fragments of antibodies ("binding polypeptides"), having the ability to selectively bind to any of the polypeptides of the invention (e.g., SEQ ID NO: 2, 4, 6, 8, or 10). Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567; 5,225,539; 5,585,089; 5,693,762 and 5,859,205. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to polypeptides of the invention (e.g., SEQ ID NO: 2, 4, 6, 8, or 10), and complexes of both the polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

The invention further provides efficient methods of identifying agents or lead compounds for agents active at the level of a polypeptide or polypeptide fragment dependent cellular function. In particular, such functions include interaction with other polypeptides or fragments. Generally, the screening methods involve assaying for compounds which interfere with the activity of a polypeptide of the invention, although compounds which enhance such activity also can be assayed using the screening methods. Such methods are adaptable to automated, high throughput screening of compounds. Target indications include cellular processes modulated by such polypeptides, for example, overexpression in cells under mechanical strains.

A wide variety of assays for candidate (pharmacological) agents are provided, including, labeled in vitro protein-ligand binding assays, electrophoretic mobility shift assays, immunoassays, cell-based assays such as two- or three-hybrid screens, expression assays, etc. The transfected nucleic acids can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding a polypeptide of the invention fused to a GAL4 DNA binding domain and a nucleic acid encoding a reporter gene operably joined to a gene expression regulatory region, such as one or more GAL4 binding sites. Activation of reporter gene transcription occurs when the reporter fusion polypeptide binds an agent such as to enable transcription of the reporter gene. Agents which modulate polypeptide mediated cell function are then detected through a change in the expression of reporter gene. Methods for determining changes in the expression of a reporter gene are known in the art.

Polypeptide fragments used in the methods, when not produced by a transfected nucleic acid are added to an assay mixture as an isolated polypeptide. Polypeptides preferably are produced recombinantly, although such polypeptides may be isolated from biological extracts. Recombinantly produced polypeptides include chimeric proteins comprising a fusion of a protein of the invention with another polypeptide, e.g., a polypeptide capable of providing or enhancing protein-protein binding, sequence specific nucleic acid binding (such as GAL4), enhancing stability of the polypeptide of the invention under assay conditions, or providing a detectable moiety, such as green fluorescent protein or a Flag epitope.

The assay mixture is comprised of a natural intracellular or extracellular binding target capable of interacting with a polypeptide of the invention. While natural polypeptide binding targets may be used, it is frequently preferred to use portions (e.g., peptides or nucleic acid fragments) or analogs (i.e., agents which mimic the polypeptide's binding properties of the natural binding target for purposes of the assay) of the polypeptide binding target so long as the portion or analog provides binding affinity and avidity to the polypeptide fragment measurable in the assay.

The assay mixture also comprises a candidate agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate agents are small organic compounds, i.e., those having a molecular weight of more than about 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be modified through conventional chemical, physical, and biochemical means. Further, known (pharmacological) agents may be subjected to directed or random chemical modifications such as acylation, alkylation, esterification, amidification, etc. to produce structural analogs of the agents.

A variety of other reagents also can be included in the mixture. These include reagents is such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The mixture of the foregoing assay materials is incubated under conditions whereby, but for the presence of the candidate agent, the chosen polypeptide of the invention specifically binds a cellular binding target, a portion thereof or analog thereof. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, a non-specific protein, etc. When the solid substrate is a magnetic bead(s), the bead(s) may be washed one or more times with a washing solution and isolated using a magnet.

Detection may be effected in any convenient way for cell-based assays such as two- or three-hybrid screens. The transcript resulting from a reporter gene transcription assay of a polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc), or indirect detection (e.g., epitope tag such as the FLAG epitope, enzyme tag such as horseseradish peroxidase, etc.). The label may be bound to a binding partner of the polypeptide, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The invention provides polypeptide-specific binding agents, methods of identifying and making such agents, and their use in diagnosis, therapy and pharmaceutical development. For example, polypeptide-specific pharmacological agents are useful in a variety of diagnostic and therapeutic applications, especially where disease or disease prognosis is associated with altered polypeptide binding characteristics. Novel polypeptide-specific binding agents include polypeptide-specific antibodies, cell surface receptors, and other natural intracellular and extracellular binding agents identified with assays such as two hybrid screens, and non-natural intracellular and extracellular binding agents identified in screens of chemical libraries and the like.

In general, the specificity of polypeptide binding to a specific molecule is determined by binding equilibrium constants. Targets which are capable of selectively binding a polypeptide preferably have binding equilibrium constants of at least about $10^7$ $M^{-1}$, more preferably at least about $10^8$ $M^{-1}$, and most preferably at least about $10^9$ $M^{-1}$. A wide variety of cell based and cell free assays may be used to demonstrate polypeptide-specific binding. Cell based assays include one, two and three hybrid screens, assays in which polypeptide-mediated transcription is inhibited or increased, etc. Cell free assays include protein binding assays, immunoassays, etc. Other assays useful for screening agents which bind polypeptides of the invention include fluorescence resonance energy transfer (FRET), and electrophoretic mobility shift analysis (EMSA).

According to still another aspect of the invention, a method of diagnosing a disorder characterized by aberrant expression of a nucleic acid molecule, an expression product thereof, or a fragment of an expression product thereof, is provided. The method involves contacting a biological sample isolated from a subject with an agent that specifically binds to the nucleic acid molecule, an expression product thereof, or a fragment of an expression product thereof, and determining the interaction between the agent and the nucleic acid molecule or the expression product as a determination of the disorder, wherein the nucleic acid molecule is selected from the group consisting of Fit-1, vacuolar ATPase, CD44, Lot-1, AA892598, and Mrg-1. In some embodiments, the disorder is a cardiovascular condition selected from the group consisting of myocardial infarction, stroke, arteriosclerosis, and heart failure. In one embodiment, the disorder is cardiac hypertrophy.

In the case where the molecule is a nucleic acid molecule, such determinations can be carried out via any standard nucleic acid determination assay, including the polymerase chain reaction, or assaying with labeled hybridization probes as exemplified herein. In the case where the molecule is an expression product of the nucleic acid molecule, or a fragment of an expression product of the nucleic acid molecule, such determination can be carried out via any standard immunological assay using, for example, antibodies which bind to any of the polypeptide expression products.

"Aberrant expression" refers to decreased expression (underexpression) or increased expression (overexpression) of any of the foregoing molecules (Fit-1, vacuolar ATPase, CD44, Lot-1, AA892598, and Mrg-1, nucleic acids and/or polypeptides) in comparison with a control (i.e., expression of the same molecule in a healthy or "normal" subject). A "healthy subject," as used herein, refers to a subject who is not at risk for developing a future cardiovascular condition (see earlier discussion and Harrison's Principles of Experimental Medicine, 13th Edition, McGraw-Hill, Inc., N.Y.—hereinafter "Harrison's"). Healthy subjects also do not otherwise exhibit symptoms of disease. In other words, such subjects, if examined by a medical professional, would be characterized as healthy and free of symptoms of a cardiovascular disorder or at risk of developing a cardiovascular disorder.

When the disorder is a cardiovascular condition selected from the group consisting of cardiac hypertrophy, myocardial infarction, stroke, arteriosclerosis, and heart failure, increased expression of any of the foregoing molecules in comparison with a control (e.g., a healthy individual) is indicative of the presence of the disorder, or indicative of the risk for developing such disorder in the future.

The invention also provides novel kits which could be used to measure the levels of the nucleic acids of the invention, or expression products of the invention.

In one embodiment, a kit comprises a package containing an agent that selectively binds to an isolated nucleic acid selected from the group consisting of Fit-1, vacuolar ATPase, CD44, Lot-1, AA892598, and Mrg-1, or expression products thereof, and a control for comparing to a measured value of binding of said agent any of the foregoing isolated nucleic acids or expression products thereof. Kits are generally comprised of the following major elements: packaging, an agent of the invention, a control agent, and instructions. Packaging may be a box-like structure for holding a vial (or number of vials) containing an agent of the invention, a vial (or number of vials) containing a control agent, and instructions. Individuals skilled in the art can readily modify the packaging to suit individual needs. In some embodiments, the control is a predetermined value for comparing to the measured value. In certain embodiments, the control comprises an epitope of the expression product of any of the foregoing isolated nucleic acids.

Figure 7:
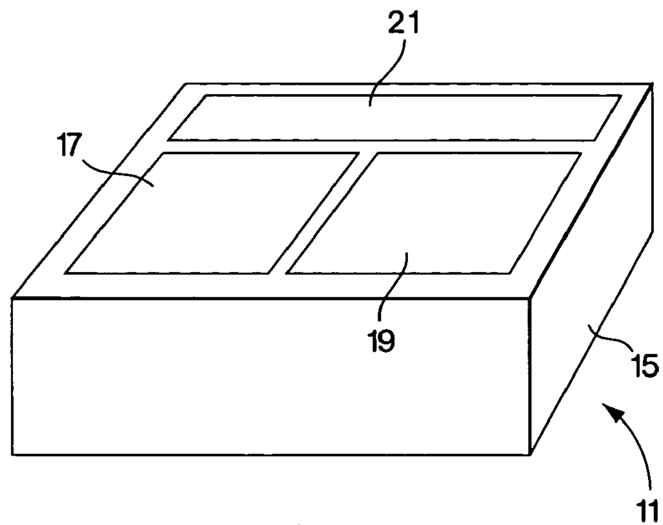
FIG. 7 depicts a kit embodying features of the present invention.

In the case of nucleic acid detection, pairs of primers for amplifying a nucleic acid molecule of the invention can be included. The preferred kits would include controls such as known amounts of nucleic acid probes, epitopes (such as Fit-1, vacuolar ATPase, CD44, Lot-1, AA892598, and Mrg-1 expression products) or anti-epitope antibodies, as well as instructions or other printed material. In certain embodiments the printed material can characterize risk of developing a cardiovascular condition based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with any of the foregoing proteins of the invention and a container containing labeled anti-human IgG antibodies. A well of the plate is contacted with, for example, a biological fluid, washed and then contacted with the anti-IgG antibody. The label is then detected. A kit embodying features of the present invention, generally designated by the numeral 11, is illustrated in FIG. 7. Kit 11 is comprised of the following major elements: packaging 15, an agent of the invention 17, a control agent 19, and instructions 21. Packaging 15 is a box-like structure for holiding a vial (or number of vials) containing an agent of the invention 17, a vial (or number of vials) containing a control agent 19, and instructions 21. Individuals skilled in the art can readily modify packaging 15 to suit individual needs.

The invention also embraces methods for treating a cardiovascular condition. In some embodiments, the method involves administering to a subject in need of such treatment a molecule selected from the group consisting of Fit-1, vacuolar ATPase, CD44, Lot-1, AA892598, and Mrg-1, in an amount effective to treat the cardiovascular condition. In certain embodiments, the method involves administering to a subject in need of such treatment an agent that increases expression of any of the foregoing molecules (Fit-1, vacuolar ATPase, CD44, Lot-1, AA892598, and Mrg-1), in an amount effective to treat the cardiovascular condition.

"Agents that increase expression" of a nucleic acid or a polypeptide, as used herein, are known in the art, and refer to sense nucleic acids, polypeptides encoded by the nucleic acids, and other agents that enhance expression of such molecules (e.g., transcription factors specific for the nucleic acids that enhance their expression). Any agents that increase exression of a molecule (and as described herein, increase its activity), are useful according to the invention.

In certain embodiments, the molecule is a nucleic acid. In some embodiments the nucleic acid is operatively coupled to a gene expression sequence which directs the expression of the nucleic acid molecule within a cardiomyocyte. The "gene expression sequence" is any regulatory nucleotide sequence, such as a promoter sequence or promoter-enhancer combination, which facilitates the efficient transcription and translation of the nucleic acid to which it is operably joined. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, α-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are activated in the presence of an inducing agent. For example, the metallothionein promoter is activated to increase transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined nucleic acid. The gene expression sequences optionally includes enhancer sequences or upstream activator sequences as desired.

Preferably, any of the nucleic acid molecules of the invention (e.g., Fit-1, vacuolar ATPase, CD44, Lot-1, AA892598, and Mrg-1) is linked to a gene expression sequence which permits expression of the nucleic acid molecule in a cell such as a cardiomyocyte and/or a vascular endothelial cell (including a smooth muscle cell). More preferably, the gene expression sequence permits expression of the nucleic acid molecule in a cardiomyocyte, and does not permit expression of the molecule in a cell selected from the group consisting of a neuronal cell, a fibroblast, and a cell of hematopoietic origin. A sequence which permits expression of the nucleic acid molecule in a cardiomyocyte, is one which is selectively active in such a cell type, thereby causing expression of the nucleic acid molecule in the cell. The cardiac myosin heavy chain gene promoter, for example, can be used to express any of the foregoing nucleic acid molecules of the invention in a cardiomyocyte. Those of ordinary skill in the art will be able to easily identify alternative promoters that are capable of expressing a nucleic acid molecule in a cardiomyocyte.

The nucleic acid sequence and the gene expression sequence are said to be "operably joined" when they are covalently linked in such a way as to place the transcription and/or translation of the nucleic acid coding sequence under the influence or control of the gene expression sequence. If it is desired that the nucleic acid sequence be translated into a functional protein, two DNA sequences are said to be operably joined if induction of a promoter in the 5' gene expression sequence results in the transcription of the nucleic acid sequence and if the nature of the linkage between the two DNA sequences does not (1) result in the introduction of a frame-shift mutation, (2) interfere with the ability of the promoter region to direct the transcription of the nucleic acid sequence, and/or (3) interfere with the ability of the corresponding RNA transcript to be translated into a protein. Thus, a gene expression sequence would be operably linked to a nucleic acid sequence if the gene expression sequence were capable of effecting transcription of that nucleic acid sequence such that the resulting transcript might be translated into the desired protein or polypeptide.

The molecules of the invention can be delivered to the preferred cell types of the invention alone or in association with a vector. In its broadest sense, a "vector" is any vehicle capable of facilitating: (1) delivery of a molecule to a target cell and/or (2) uptake of the molecule by a target cell. Preferably, the vectors transport the molecule into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing a nucleic acid or a protein) can be selectively delivered to a cardiomyocyte cell in, e.g., the myocardium. Methodologies for targeting include conjugates, such as those described in U.S. Pat. No. 5,391,723 to Priest. Another example of a well-known targeting vehicle is a liposome. Liposomes are commercially available from Gibco BRL (Life Technologies Inc., Rockville, Md.). Numerous methods are published for making targeted liposomes. Preferably, the molecules of the invention are targeted for delivery to cardiomyocytes, and/or vascular endothelial cells.

In general, the vectors useful in the invention include, but are not limited to, plasmids, phagemids, viruses, other vehicles derived from viral or bacterial sources that have been manipulated by the insertion or incorporation of the nucleic acid sequences of the invention, and additional nucleic acid fragments (e.g., enhancers, promoters) which can be attached to the nucleic acid sequences of the invention. Viral vectors are a preferred type of vector and include, but are not limited to, nucleic acid sequences from the following viruses: adenovirus; adeno-associated virus; retrovirus, such as Moloney murine leukemia virus; Harvey murine sarcoma virus; murine mammary tumor virus; rouse sarcoma virus; SV40-type viruses; polyoma viruses; Epstein-Barr viruses; papilloma viruses; herpes virus; vaccinia virus; polio virus; and RNA viruses such as a retrovirus. One can readily employ other vectors not named but known in the art.

A particularly preferred virus for certain applications is the adeno-associated virus, a double-stranded DNA virus. The adeno-associated virus is capable of infecting a wide range of cell types and species and can be engineered to be replication-deficient i.e., capable of directing synthesis of the desired proteins, but incapable of manufacturing an infectious particle. It further has advantages, such as heat and lipid solvent stability, high transduction frequencies in cells of diverse lineages, including hematopoietic cells, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient. Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Cliffton, N.J. (1991).

Another preferred retroviral vector is the vector derived from the Moloney murine leukemia virus, as described in Nabel, E. G., et al., *Science,* 1990, 249:1285-1288. These vectors reportedly were effective for the delivery of genes to all three layers of the arterial wall, including the media. Other preferred vectors are disclosed in Flugelman, et al., *Circulation,* 1992, 85:1110-1117. Additional vectors that are useful for delivering molecules of the invention are described in U.S. Pat. No. 5,674,722 by Mulligan, et. al.

In addition to the foregoing vectors, other delivery methods may be used to deliver a molecule of the invention to a cell such as a cardiomyocyte and/or a vascular endothelial cell, and facilitate uptake thereby.

A preferred such delivery method of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 μm can encapsulate large macromolecules. RNA, DNA, and intact virions can be encapsulated within the aqueous interior and be delivered to cells in a biologically active form (Fraley, et al., *Trends Biochem. Sci.,* 1981, 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, such as the myocardium or the vascular cell wall, by coupling the liposome to a specific ligand such as a monoclonal antibody, sugar, glycolipid, or protein. Ligands which may be useful for targeting a liposome to the vascular wall include, but are not limited to, the viral coat protein of the Hemagglutinating virus of Japan. Additionally, the vector may be coupled to a nuclear targeting peptide, which will direct the nucleic acid to the nucleus of the host cell.

Liposomes are commercially available from Gibco BRL, for example, as LIPOFECTIN™ and LIPOFECTACE™, which are formed of cationic lipids such as N-[1-(2,3-dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235-241 (1985). Novel liposomes for the intracellular delivery of macromolecules, including nucleic acids, are also described in PCT International application no. PCT/US96/07572 (Publication No. WO 96/40060, entitled "Intracellular Delivery of Macromolecules").

In one particular embodiment, the preferred vehicle is a biocompatible micro particle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", which claims priority to U.S. patent application Ser. No. 213,668, filed Mar. 15, 1994). PCT/US/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the nucleic acids described herein are encapsulated or dispersed within the biocompatible, preferably biodegradable polymeric matrix disclosed in PCT/US/03307. The polymeric matrix preferably is in the form of a micro particle such as a micro sphere (wherein a nucleic acid is dispersed throughout a solid polymeric matrix) or a microcapsule (wherein a nucleic acid is stored in the core of a polymeric shell). Other forms of the polymeric matrix for containing the nucleic acids of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular surface. The matrix composition also can be selected not to degrade, but rather, to release by diffusion over an extended period of time.

Both non-biodegradable and biodegradable polymeric matrices can be used to deliver the nucleic acids of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the nucleic acids of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and co-polymers thereof, alkyl cellulose, hydroxyalkyl celluloses, cellulose ethers, cellulose esters, nitrocelluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methylmethacrylate), poly (ethylmethacrylate), poly(butylmethacrylate), poly(isobutylmethacrylate), poly(hexylmethacrylate), poly (isodecylmethacrylate), poly(laurylmethacrylate), poly (phenylmethacrylate), poly(methylacrylate), poly (isopropylacrylate), poly(isobutylacrylate), poly (octadecylacrylate), polyethylene, polypropylene, poly (ethyleneglycol), poly(ethyleneoxide), poly (ethyleneterephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Thus, the invention provides a composition of the above-described molecules of the invention for use as a medicament, methods for preparing the medicament and methods for the sustained release of the medicament in vivo.

Compaction agents also can be used in combination with a vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, e.g., to deliver an isolated nucleic acid of the invention in a form that is more efficiently taken up by the cell or, more preferably, in combination with one or more of the above-described vectors.

Other exemplary compositions that can be used to facilitate uptake by a target cell of the nucleic acids of the invention include calcium phosphate and other chemical mediators of intracellular transport, microinjection compositions, electroporation and homologous recombination compositions (e.g., for integrating a nucleic acid into a preselected location within the target cell chromosome).

The invention also provides methods for the diagnosis and therapy of vascular and cardiovascular disorders. Such disorders include myocardial infarction, stroke, arteriosclerosis, heart failure, and cardiac hypertrophy.

The methods of the invention are useful in both the acute and the prophylactic treatment of any of the foregoing conditions. As used herein, an acute treatment refers to the treatment of subjects having a particular condition. Prophylactic treatment refers to the treatment of subjects at risk of having the condition, but not presently having or experiencing the symptoms of the condition.

In its broadest sense, the terms "treatment" or "to treat" refer to both acute and prophylactic treatments. If the subject in need of treatment is experiencing a condition (or has or is having a particular condition), then treating the condition refers to ameliorating, reducing or eliminating the condition or one or more symptoms arising from the condition. In some preferred embodiments, treating the condition refers to ameliorating, reducing or eliminating a specific symptom or a specific subset of symptoms associated with the condition. If the subject in need of treatment is one who is at risk of having a condition, then treating the subject refers to reducing the risk of the subject having the condition.

Stroke (also referred to herein as ischemic stroke and/or cerebrovascular ischemia) is often cited as the third most common cause of death in the industrial world, ranking behind ischemic heart disease and cancer. Strokes are responsible for about 300,000 deaths annually in the United States and are a leading cause of hospital admissions and long-term disabilities. Accordingly, the socioeconomic impact of stroke and its attendant burden on society is practically immeasurable.

"Stroke" is defined by the World Health Organization as a rapidly developing clinical sign of focal or global disturbance of cerebral function with symptoms lasting at least 24 hours. Strokes are also implicated in deaths where there is no apparent cause other than an effect of vascular origin.

Strokes are typically caused by blockages or occlusions of the blood vessels to the brain or within the brain. With complete occlusion, arrest of cerebral circulation causes cessation of neuronal electrical activity within seconds. Within a few minutes after the deterioration of the energy state and ion homeostasis, depletion of high energy phosphates, membrane ion pump failure, efflux of cellular potassium, influx of sodium chloride and water, and membrane depolarization occur. If the occlusion persists for more than five to ten minutes, irreversible damage results. With incomplete ischemia, however, the outcome is difficult to evaluate and depends largely on residual perfusion and the availability of oxygen. After a thrombotic occlusion of a cerebral vessel, ischemia is rarely total. Some residual perfusion usually persists in the ischemic area, depending on collateral blood flow and local perfusion pressure.

Cerebral blood flow can compensate for drops in mean arterial blood pressure from 90 to 60 mm Hg by autoregulation. This phenomenon involves dilatation of downstream resistant vessels. Below the lower level of autoregulation (about 60 mm Hg), vasodilatation is inadequate and the cerebral blood flow falls. The brain, however, has perfusion reserves that can compensate for the fall in cerebral blood flow. This reserve exists because under normal conditions only about 35% of the oxygen delivered by the blood is extracted. Therefore, increased oxygen extraction can take place, provided that normoxia and normocapnea exist. When distal blood pressure falls below approximately 30 mm Hg, the two compensatory mechanisms (autoregulation and perfusion reserve) are inadequate to prevent failure of oxygen delivery.

As blood flow drops below the ischemic threshold of 23 ml/100 g/minute, symptoms of tissue hypoxia develop. Severe ischemia may be lethal. When the ischemia is moderate, it will result in "penumbra." In the neurological context, penumbra refers to a zone of brain tissue with moderate ischemia and paralyzed neuronal function, which is reversible with restoration of adequate perfusion. The penumbra forms a zone of collaterally perfused tissue surrounding a core of severe ischemia in which an infarct has developed. In other words, the penumbra is the tissue area that can be saved, and is essentially in a state between life and death.

Although an ischemic event can occur anywhere in the vascular system, the carotid artery bifurcation and the origin of the internal carotid artery are the most frequent sites for thrombotic occlusions of cerebral blood vessels, which result in cerebral ischemia. The symptoms of reduced blood flow due to stenosis or thrombosis are similar to those caused by middle cerebral artery disease. Flow through the ophthalmic artery is often affected sufficiently to produce amaurosis fugax or transient monocular blindness. Severe bilateral internal carotid artery stenosis may result in cerebral hemispheric hypoperfusion. This manifests with acute headache ipsilateral to the acutely ischemic hemisphere. Occlusions or decrease of the blood flow with resulting ischemia of one anterior cerebral artery distal to the anterior communicating artery produces motor and cortical sensory symptoms in the contralateral leg and, less often, proximal arm. Other manifestations of occlusions or underperfusion of the anterior cerebral artery include gait ataxia and sometimes urinary incontinence due to damage to the parasagital frontal lobe. Language disturbances manifested as decreased spontaneous speech may accompany generalized depression of psychomotor activity.

Most ischemic strokes involve portions or all of the territory of the middle cerebral artery with emboli from the heart or extracranial carotid arteries accounting for most cases. Emboli may occlude the main stem of the middle cerebral artery, but more frequently produce distal occlusion of either the superior or the inferior branch. Occlusions of the superior branch cause weakness and sensory loss that are greatest in the face and arm. Occlusions of the posterior cerebral artery distal to its penetrating branches cause complete contralateral loss of vision. Difficulty in reading (dyslexia) and in performing calculations (dyscalculia) may follow ischemia of the dominant posterior cerebral artery. Proximal occlusion of the posterior cerebral artery causes ischemia of the branches penetrating to calamic and limbic structures. The clinical results are hemisensory disturbances that may chronically change to intractable pain of the defective side (thalamic pain).

A subject having a stroke is so diagnosed by symptoms experienced and/or by a physical examination including interventional and non-interventional diagnostic tools such as CT and MR imaging. The methods of the invention are advantageous for the treatment of various clinical presentations of stroke subjects. A subject having a stroke may present with one or more of the following symptoms: paralysis, weakness, decreased sensation and/or vision, numbness, tingling, aphasia (e.g., inability to speak or slurred speech, difficulty reading or writing), agnosia (i.e., inability to recognize or identify sensory stimuli), loss of memory, co-ordination difficulties, lethargy, sleepiness or unconsciousness, lack of bladder or bowel control and cognitive decline (e.g., dementia, limited attention span, inability to concentrate). Using medical imaging techniques, it may be possible to identify a subject having a stroke as one having an infarct or one having hemorrhage in the brain.

An important embodiment of the invention is treatment of a subject with an abnormally elevated risk of an ischemic stroke. As used herein, subjects having an abnormally elevated risk of an ischemic stroke are a category determined according to conventional medical practice (see earlier discussion); such subjects may also be identified in conventional medical practice as having known risk factors for stroke or having increased risk of cerebrovascular events. This category includes, for example, subjects which are having elected vascular surgery. Typically, the risk factors associated with cardiac disease are the same as are associated with stroke. The primary risk factors include hypertension, hypercholesterolemia, and smoking. Atrial fibrillation or recent myocardial infarction are also important risk factors. In addition, modified levels of expression of a nucleic acid molecule selected from the group consisting of Fit-1, vacuolar ATPase, CD44, Lot-1, AA892598, and Mrg-1, or an expression product thereof, are also, according to the present invention, important risk factors.

As used herein, subjects having an abnormally elevated risk of an ischemic stroke also include individuals undergoing surgical or diagnostic procedures which risk release of emboli, lowering of blood pressure or decrease in blood flow to the brain, such as carotid endarterectomy, brain angiography, neurosurgical procedures in which blood vessels are compressed or occluded, cardiac catheterization, angioplasty, including balloon angioplasty, coronary by-pass surgery, or similar procedures. Subjects having an abnormally elevated risk of an ischemic stroke also include individuals having any cardiac condition that may lead to decreased blood flow to the brain, such as atrial fibrillation, ventrical tachycardia, dilated cardiomyopathy and other cardiac conditions requiring anticoagulation. Subjects having an abnormally elevated risk of an ischemic stroke also include individuals having conditions including arteriopathy or brain vasculitis, such as that caused by lupus, congenital diseases of blood vessels, such as CADASIL syndrome, or migraine, especially prolonged episodes.

The treatment of stroke can be for patients who have experienced a stroke or can be a prophylactic treatment. Short term prophylactic treatment is indicated for subjects having surgical or diagnostic procedures which risk release of emboli, lowering of blood pressure or decrease in blood flow to the brain, to reduce the injury due to any ischemic event that occurs as a consequence of the procedure. Longer term or chronic prophylactic treatment is indicated for subjects having cardiac conditions that may lead to decreased blood flow to the brain, or conditions directly affecting brain vasculature. If prophylactic, then the treatment is for subjects having an abnormally elevated risk of an ischemic stroke, as described above. If the subject has experienced a stroke, then the treatment can include acute treatment. Acute treatment for stroke subjects means administration of an agent of the invention at the onset of symptoms of the condition or within 48 hours of the onset, preferably within 24 hours, more preferably within 12 hours, more preferably within 6 hours, and even more preferably within 3 hours of the onset of symptoms of the condition.

Criteria for defining hypercholesterolemic and/or hypertriglyceridemic subjects are well known in the art (see, e.g., "Harrison's"). Hypercholesterolemic subjects and hypertriglyceridemic subjects are associated with increased incidence of premature coronary heart disease. A hypercholesterolemic subject has an LDL level of >160 mg/dL or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject has a triglyceride (TG) level of >250 mg/dL. Thus, a hyperlipidemic subject is defined as one whose cholesterol and triglyceride levels equal or exceed the limits set as described above for both the hypercholesterolemic and hypertriglyceridemic subjects.

"Myocardial infarction" is a focus of necrosis resulting from inadequate perfusion of the cardiac tissue. Myocardial infarction generally occurs with the abrupt decrease in coronary blood flow that follows a thrombotic occlusion of a coronary artery previously narrowed by atherosclerosis. Generally, infarction occurs when an atherosclerotic plaque fissures, ruptures, or ulcerates, and a mural thrombus forms leading to coronary artery occlusion.

The diagnosis of myocardial infarction in a subject determines the need for treating the subject according to the methods of the invention. A number of laboratory tests, well known in the art, are described, for example, in Harrison's. Generally, the tests may be divided into four main categories: (1) nonspecific indexes of tissue necrosis and inflammation, (2) electrocardiograms, (3) serum enzyme changes (e.g., creatine phosphokinase levels), and (4) cardiac imaging. A person of ordinary skill in the art could easily apply any of the foregoing tests to determine when a subject is at risk, is suffering, or has suffered, a myocardial infarction. In addition, decreased levels of expression of a nucleic acid molecule selected from the group consisting of Fit-1, vacuolar ATPase, CD44, Lot-1, AA892598, and Mrg-1, or an expression product thereof, are also, according to the present invention, important risk factors. A positively identified subject would thus benefit from a method of treatment of the invention.

According to the invention, the method involves administering to a subject having a myocardial infarction any of the foregoing molecules (Fit-1, vacuolar ATPase, CD44, Lot-1, AA892598, and Mrg-1) in an amount effective to treat the cardiovascular disorder in the subject. By "having a myocardial infarction" it is meant that the subject is at risk of developing, is currently having, or has suffered a myocardial infarction. It is believed that immediate administration of the molecule would greatly benefit the subject by inhibiting apoptotic cell-death of cardiomyocytes (the cells mostly affected by the infarct) prior to, or following the infarct. By "immediate" it is meant that administration occurs before (if it is diagnosed in time), or within 48 hours from the myocardial infarct, although administration up to 14 days after the episode may also be beneficial to the subject.

Another important embodiment of the invention is the treatment of ischemic injury resulting from arteriosclerosis. Arteriosclerosis is a term used to describe a thickening and hardening of the arterial wall. It is believed to be responsible for the majority of deaths in the United States and in most westernized societies. Atherosclerosis is one type of arteriosclerosis that is believed to be the cause of most coronary artery disease, aortic aneurysm and arterial disease of the lower extremities (including peripheral vascular arteriopathy), as well as contributing to cerebrovascular disease. Atherosclerosis is the leading cause of death in the United States.

A normal artery typically is lined on its inner-side only by a single layer of endothelial cells, the intima. The intima overlays the media, which contains only a single cell type, the smooth muscle cell. The outer-most layer of the artery is the adventitia. With aging, there is a continuous increase in the thickness of the intima, believed to result in part from migration and proliferation of smooth muscle cells from the media. A similar increase in the thickness of the intima also occurs as a result of various traumatic events or interventions, such as occurs when, for example, a balloon dilatation procedure causes injury to the vessel wall. The invention is used in connection with treating ischemic injury resulting from arteriosclerotic conditions. An arteriosclerotic condition as used herein means classical atherosclerosis, accelerated atherosclerosis, atherosclerosis lesions and any other arteriosclerotic conditions characterized by undesirable endothelial and/or vascular smooth muscle cell proliferation, including vascular complications of diabetes.

Another important embodiment of the invention is the treatment of heart failure. Heart failure is a clinical syndrome of diverse etiologies linked by the common denominator of impaired heart pumping and is characterized by the failure of the heart to pump blood commensurate with the requirements of the metabolizing tissues, or to do so only from an elevating filling pressure.

Another important embodiment of the invention is the treatment of cardiac hypertrophy. This condition is typically characterized by left ventricular hypertrophy, usually of a nondilated chamber, without obvious antecedent cause. Current methods of diagnosis include the electrocardiogram and the echocardiogram. Many patients, however, are asymptomatic and may be relatives of patients with known disease. Unfortunately, the first manifestation of the disease may be sudden death, frequently occurring in children and young adults, often during or after physical exertion.

Agents for reducing the risk of or treating a cardiovascular disorder include those selected from the group consisting of anti-inflammatory agents, anti-thrombotic agents, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), calcium channel blockers, beta-adrenergic receptor blockers, cyclooxygenase-2 inhibitors, angiotensin system inhibitors, and/or any combinations thereof. One preferred agent is aspirin.

The mode of administration and dosage of a therapeutic agent of the invention will vary with the particular stage of the condition being treated, the age and physical condition of the subject being treated, the duration of the treatment, the nature of the concurrent therapy (if any), the specific route of administration, and the like factors within the knowledge and expertise of the health practitioner.

As described herein, the agents of the invention are administered in effective amounts to treat any of the foregoing cardiovascular disorders. In general, an effective amount is any amount that can cause a beneficial change in a desired tissue of a subject. Preferably, an effective amount is that amount sufficient to cause a favorable phenotypic change in a particular condition such as a lessening, alleviation or elimination of a symptom or of a condition as a whole.

In general, an effective amount is that amount of a pharmaceutical preparation that alone, or together with further doses, produces the desired response. This may involve only slowing the progression of the condition temporarily, although more preferably, it involves halting the progression of the condition permanently or delaying the onset of or preventing the condition from occurring. This can be monitored by routine methods. Generally, doses of active compounds would be from about 0.01 mg/kg per day to 1000 mg/kg per day. It is expected that doses ranging from 50-500 mg/kg will be suitable, preferably orally and in one or several administrations per day.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. Lower doses will result from certain forms of administration, such as intravenous administration.

In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The agents of the invention may be combined, optionally, with a pharmaceutically-acceptable carrier to form a pharmaceutical preparation. The term "pharmaceutically-acceptable carrier," as used herein, means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. In some aspects, the pharmaceutical preparations comprise an agent of the invention in an amount effective to treat a disorder.

The pharmaceutical preparations may contain suitable buffering agents, including: acetic acid in a salt; citric acid in a salt; boric acid in a salt; or phosphoric acid in a salt. The pharmaceutical compositions also may contain, optionally, suitable preservatives, such as: benzalkonium chloride; chlorobutanol; parabens or thimerosal.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, intradermal, transdermal, or parenteral routes. The term "parenteral" includes subcutaneous, intravenous, intramuscular, or infusion. Intravenous or intramuscular routes are not particularly suitable for long-term therapy and prophylaxis. As an example, pharmaceutical compositions for the acute treatment of subjects having a migraine headache may be formulated in a variety of different ways and for a variety of administration modes including tablets, capsules, powders, suppositories, injections and nasal sprays.

The pharmaceutical preparations may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of an agent of the invention, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid may be used in the preparation of injectables. Formulations suitable for oral, subcutaneous, intravenous, intramuscular, etc. administrations can be found in *Remington's Pharmaceutical Sciences*, Mack Publishing Co., Easton, Pa.

The term "permit entry" of a molecule into a cell according to the invention has the following meanings depending upon the nature of the molecule. For an isolated nucleic acid it is meant to describe entry of the nucleic acid through the cell membrane and into the cell nucleus, where upon the "nucleic acid transgene" can utilize the cell machinery to produce functional polypeptides encoded by the nucleic acid. By "nucleic acid transgene" it is meant to describe all of the nucleic acids of the invention with or without the associated vectors. For a polypeptide, it is meant to describe entry of the polypeptide through the cell membrane and into the cell cytoplasm, and if necessary, utilization of the cell cytoplasmic machinery to functionally modify the polypeptide (e.g., to an active form).

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a liposome, a retrovirus, or other virus) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time release, delayed release or sustained release delivery systems. Such systems can avoid repeated administrations of an agent of the present invention, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775; 4,675,189; and 5,736,152; and (b) diffusional systems in which an active component permeates at a controlled rate from a polymer such as described in U.S. Pat. Nos. 3,854,480; 5,133,974; and 5,407,686. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active ingredient for at least 30 days, and preferably 60 days. Long-term sustained release implants are well-known to those of ordinary skill in the art and include some of the release systems described above. Specific examples include, but are not limited to, long-term sustained release implants described in U.S. Pat. No. 4,748,024, and Canadian Patent No. 1330939.

The invention also involves the administration, and in some embodiments co-administration, of agents other than the molecules of the invention (Fit-1, vacuolar ATPase, CD44, Lot-1, AA892598, and Mrg-1, nucleic acids and polypeptides, and/or fragments thereof) that when administered in effective amounts can act cooperatively, additively or synergistically with a molecule of the invention to: (i) modulate cardiac cell anti-apoptotic activity, and (ii) treat any of the conditions in which cardiac cell anti-apoptotic activity of a molecule of the invention is involved. Agents other than the molecules of the invention include anti-inflammatory agents, anti-thrombotic agents, anti-coagulants, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules, calcium channel blockers, beta-adrenergic receptor blockers, cyclooxygenase-2 inhibitors, angiotensin system inhibitors, anti-hypertensive agents, and/or combinations thereof.

"Anti-inflammatory" agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; and Zomepirac Sodium. One preferred anti-inflammatory agent is aspirin.

"Anti-thrombotic" and/or "fibrinolytic" agents include plasminogen (to plasmin via interactions of prekallikrein, kininogens, Factors XII, XIIIa, plasminogen proactivator, and tissue plasminogen activator[TPA]) Streptokinase; Urokinase: Anisoylated Plasminogen-Streptokinase Activator Complex; Pro-Urokinase; (Pro-UK); rTPA (alteplase or activase; "r" denotes recombinant); rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; Retaplase; Trifenagrel; Warfarin; and Dextrans.

"Anti-platelet" agents include Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; and Anagrelide.

"Lipid reducing" agents include gemfibrozil, cholystyramine, colestipol, nicotinic acid, probucol lovastatin, fluvastatin, simvastatin, atorvastatin, pravastatin, and cirivastatin.

"Direct thrombin inhibitors" include hirudin, hirugen, hirulog, agatroban, PPACK, and thrombin aptamers.

"Glycoprotein IIb/IIIa receptor inhibitors" embraces both antibodies and non-antibodies, and include, but are not limited, to ReoPro (abcixamab), lamifiban, and tirofiban.

"Calcium channel blockers" are a chemically diverse class of compounds having important therapeutic value in the control of a variety of diseases including several cardiovascular disorders, such as hypertension, angina, and cardiac arrhythmias (Fleckenstein, *Cir. Res.* v. 52, (suppl. 1), p. 13-16 (1983); Fleckenstein, *Experimental Facts and Therapeutic Prospects*, John Wiley, New York (1983); McCall, D., *Curr Pract Cardiol*, v. 10, p. 1-11 (1985)). Calcium channel blockers are a heterogeneous group of drugs that prevent or slow the entry of calcium into cells by regulating cellular calcium channels. (Remington, *The Science and Practice of Pharmacy*, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexylene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol,7-(2-hydroxy-3-t-butylaminpropoxy)phthalide. The above-identified compounds can be used as isomeric mixtures, or in their respective levorotating or dextrorotating form.

Cyclooxygenase-2 (COX-2) is a recently identified form of a cyclooxygenase. "Cyclooxygenase" is an enzyme complex present in most tissues that produces various prostaglandins and thromboxanes from arachidonic acid. Non-steroidal, anti-inflammatory drugs exert most of their anti-inflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It and was originally identified in bovine seminal vesicles.

Cyclooxygenase-2 (COX-2) has been cloned, sequenced and characterized initially from chicken, murine and human sources (see, e.g., U.S. Pat. No. 5,543,297, issued Aug. 6, 1996 to Cromlish et al., and assigned to Merck Frosst Canada, Inc., Kirkland, Calif., entitled: "Human cyclooxygenase-2 cDNA and assays for evaluating cyclooxygenase-2 activity"). This enzyme is distinct from COX-1. COX-2 is rapidly and readily inducible by a number of agents including mitogens, endotoxin, hormones, cytokines and growth factors. As prostaglandins have both physiological and pathological roles, the constitutive enzyme, COX-1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar anti-inflammatory, antipyretic and analgesic properties to a conventional non-steroidal anti-inflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective "COX-2 inhibitors" are known in the art. These include, but are not limited to, COX-2 inhibitors described in U.S. Pat. No. 5,474,995 "Phenyl heterocycles as COX-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-Benzylindol-3-yl propanoic acid derivatives as cyclooxygenase inhibitors"; U.S. Pat. No. 5,604,260 "5-Methanesulfonamido-1-indanones as an inhibitor of cyclooxygenase-2"; U.S. Pat. No. 5,639,780 N-Benzyl indol-3-yl butanoic acid derivatives as cyclooxygenase inhibitors"; U.S. Pat. No. 5,677,318 "Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-Diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif. or Merck & Co., Inc. (Rahway, N.J.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An "angiotensin system inhibitor" is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

"Angiotensin II antagonists" are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [$(San^1)(Val^5)(Ala^8)$] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile), imidazole-5-acetic acid (see Long et al., *J. Pharmacol. Exp. Ther.* 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(−1-naphthyl)-L-alanyl-(4, thiazolyl)-L-alanyl (35,45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxyphenyl)methyl] 1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D. Searle and Company).

"Angiotensin converting enzyme," (ACE), is an enzyme which catalyzes the conversion of angiotensin I to angiotensin II. ACE inhibitors include amino acids and derivatives thereof, peptides, including di- and tripeptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

"Renin inhibitors" are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies described above.

Anticoagulant agents include, but are not limited to, Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bivalirudin; Bromindione; Dalteparin Sodium; Desirudin; Dicumarol; Heparin Calcium; Heparin Sodium; Lyapolate Sodium; Nafamostat Mesylate; Phenprocoumon; Tinzaparin Sodium; and Warfarin Sodium.

Heparin may stabilize symptoms in evolving stroke, but anticoagulants are useless (and possibly dangerous) in acute completed stroke, and are contraindicated in hypertensives because of the increased possibility of hemorrhage into the brain or other organs. Although the timing is controversial, anticoagulants may be started to prevent recurrent cardiogenic emboli. Clot lysing agents, including tissue plasminogen activator and streptokinase, are being evaluated for the very early treatment of acute stroke. Nimodipine has recently been shown to improve survival and clinical outcome after ischemic stroke.

Other than aspirin, ticlopidine is another antiplatelet agent that has been shown to be beneficial for stroke treatment. Endarterectomy may be indicated in patients with 70 to 99 percent narrowing of a symptomatic internal carotid artery. However, most authorities agree that carotid endarterectomy is not indicated in patients with TIAs that are referable to the basilar-vertebral system, in patients with significant deficits from prior strokes, or in patients in whom a stroke is evolving.

HMG-CoA (3-hydroxy-3-methylglutaryl-coenzyme A) reductase is the microsomal enzyme that catalyzes the rate limiting reaction in cholesterol biosynthesis (HMG-CoA6Mevalonate). An HMG-CoA reductase inhibitor inhibits HMG-CoA reductase, and as a result inhibits the synthesis of cholesterol. A number of HMG-CoA reductase inhibitors has been used to treat individuals with hypercholesterolemia. More recently, HMG-CoA reductase inhibitors have been shown to be beneficial in the treatment of stroke (Endres M, et al., *Proc Natl Acad Sci USA,* 1998, 95:8880-5).

HMG-CoA reductase inhibitors useful for co-administration with the agents of the invention include, but are not limited to, simvastatin (U.S. Pat. No. 4,444,784); lovastatin (U.S. Pat. No. 4,231,938); pravastatin sodium (U.S. Pat. No. 4,346,227); fluvastatin (U.S. Pat. No. 4,739,073); atorvastatin (U.S. Pat. No. 5,273,995); cerivastatin, and numerous others described in U.S. Pat. No. 5,622,985; U.S. Pat. No. 5,135,935; U.S. Pat. No. 5,356,896; U.S. Pat. No. 4,920,109; U.S. Pat. No. 5,286,895; U.S. Pat. No. 5,262,435; U.S. Pat. No. 5,260,332; U.S. Pat. No. 5,317,031; U.S. Pat. No. 5,283,256; U.S. Pat. No. 5,256,689; U.S. Pat. No. 5,182,298; U.S. Pat. No. 5,369,125; U.S. Pat. No. 5,302,604; U.S. Pat. No. 5,166,171; U.S. Pat. No. 5,202,327; U.S. Pat. No. 5,276,021; U.S. Pat. No. 5,196,440; U.S. Pat. No. 5,091,386; U.S. Pat. No. 5,091,378; U.S. Pat. No. 4,904,646; U.S. Pat. No. 5,385,932; U.S. Pat. No. 5,250,435; U.S. Pat. No. 5,132,312; U.S. Pat. No. 5,130,306; U.S. Pat. No. 5,116,870; U.S. Pat. No. 5,112,857; U.S. Pat. No. 5,102,911; U.S. Pat. No. 5,098,931; U.S. Pat. No. 5,081,136; U.S. Pat. No. 5,025,000; U.S. Pat. No. 5,021,453; U.S. Pat. No. 5,017,716; U.S. Pat. No. 5,001,144; U.S. Pat. No. 5,001,128; U.S. Pat. No. 4,997,837; U.S. Pat. No. 4,996,234; U.S. Pat. No. 4,994,494; U.S. Pat. No. 4,992,429; U.S. Pat. No. 4,970,231; U.S. Pat. No. 4,968,693; U.S. Pat. No. 4,963,538; U.S. Pat. No. 4,957,940; U.S. Pat. No. 4,950,675; U.S. Pat. No. 4,946,864; U.S. Pat. No. 4,946,860; U.S. Pat. No. 4,940,800; U.S. Pat. No. 4,940,727; U.S. Pat. No. 4,939,143; U.S. Pat. No. 4,929,620; U.S. Pat. No. 4,923,861; U.S. Pat. No. 4,906,657; U.S. Pat. No. 4,906,624; and U.S. Pat. No. 4,897,402, the disclosures of which patents are incorporated herein by reference.

Nitric oxide (NO) has been recognized as a messenger molecule with many physiologic roles, in the cardiovascular, neurologic and immune systems (Griffith, T M et al., *J Am Coll Cardiol,* 1988, 12:797-806). It mediates blood vessel relaxation, neurotransmission and pathogen suppression. NO is produced from the guanidino nitrogen of L-arginine by NO Synthase (Moncada, S and Higgs, E A, *Eur J Clin Invest,* 1991, 21:361-374). Agents that upregulate endothelial cell Nitric Oxide Synthase include, but are not limited to, L-arginine, rho GTPase function inhibitors (see International Application WO 99/47153, the disclosure of which is incorporated herein by reference), and agents that disrupt actin cytoskeletal organization (see International Application WO 00/03746, the disclosure of which is incorporated herein by reference).

"Co-administering," as used herein, refers to administering simultaneously two or more compounds of the invention (e.g., a Fit-1, vacuolar ATPase, CD44, Lot-1, AA892598, and/or Mrg-1, nucleic acid and/or polypeptide, and an agent known to be beneficial in the treatment of, for example, a cardiovascular condition, e.g., an anticoagulant-), as an admixture in a single composition, or sequentially, close enough in time so that the compounds may exert an additive or even synergistic effect, i.e., on reducing cardiomyocyte cell-death in a cardiovascular condition.

The invention also embraces solid-phase nucleic acid molecule arrays. The array consists essentially of a set of nucleic acid molecules, expression products thereof, or fragments (of either the nucleic acid or the polypeptide molecule) thereof, each nucleic acid molecule selected from the group consisting of Fit-1, vacuolar ATPase, CD44, Lot-1, AA892598, and Mrg-1, fixed to a solid substrate. In some embodiments, the solid-phase array further comprises at least one control nucleic acid molecule. In certain embodiments, the set of nucleic acid molecules comprises at least one, at least two, at least three, at least four, or even at least five nucleic acid molecules, each selected from the group consisting of Fit-1, vacuolar ATPase, CD44, Lot-1, AA892598, and Mrg-1, provided that when only one nucleic acid molecule is present on the array, the nucleic acid molecule is not vacuolar ATPase. In preferred embodiments, the set of nucleic acid molecules comprises a maximum number of 100 different nucleic acid molecules. In important embodiments, the set of nucleic acid molecules comprises a maximum number of 10 different nucleic acid molecules.

According to the invention, standard hybridization techniques of microarray technology are utilized to assess patterns of nucleic acid expression and identify nucleic acid expression. Microarray technology, which is also known by other names including: DNA chip technology, gene chip technology, and solid-phase nucleic acid array technology, is well known to those of ordinary skill in the art and is based on, but not limited to, obtaining an array of identified nucleic acid probes (e.g., molecules described elsewhere herein such as Fit-1, vacuolar ATPase, CD44, Lot-1, AA892598, and/or Mrg-1) on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in Nature Genetics, Vol. 21, January 1999, the entire contents of which is incorporated by reference herein.

According to the present invention, microarray substrates may include but are not limited to glass, silica, aluminosilicates, borosilicates, metal oxides such as alumina and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of two or more of the nucleic acid molecules set forth as SEQ ID NOs: 1, 3, 5, 7, 9, 11 and/or 12. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, but are not limited to: amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Nature Genetics, Vol. 21, January 1999) or chromium (Gwynne and Page, 2000). In this embodiment, presynthesized probes are applied to the substrate in a precise, predetermined volume and grid pattern, utilizing a computer-controlled robot to apply probe to the substrate in a contact-printing manner or in a non-contact manner such as inkjet or piezo-electric delivery. Probes may be covalently linked to the substrate with methods that include, but are not limited to, UV-irradiation and heat.

Targets are nucleic acids selected from the group, including but not limited to, DNA, genomic DNA, cDNA, RNA, mRNA and may be natural or synthetic. In all embodiments, nucleic acid molecules from subjects suspected of developing or having a cardiovascular condition, are preferred. In certain embodiments of the invention, one or more control nucleic acid molecules are attached to the substrate. Preferably, control nucleic acid molecules allow determination of factors including but not limited to: nucleic acid quality and binding characteristics; reagent quality and effectiveness; hybridization success; and analysis thresholds and success. Control nucleic acids may include, but are not limited to, expression products of genes such as housekeeping genes or fragments thereof.

To select a set of cardiovascular disease markers, the expression data generated by, for example, microarray analysis of gene expression, is preferably analyzed to determine which genes in different categories of patients (each category of patients being a different cardiovascular disorder), are significantly differentially expressed. The significance of gene expression can be determined using Permax computer software, although any standard statistical package that can discriminate significant differences is expression may be used. Permax performs permutation 2-sample t-tests on large arrays of data. For high dimensional vectors of observations, the Permax software computes t-statistics for each attribute, and assesses significance using the permutation distribution of the maximum and minimum overall attributes. The main use is to determine the attributes (genes) that are the most different between two groups (e.g., control healthy subject and a subject with a particular cardiovascular disorder), measuring "most different" using the value of the t-statistics, and their significance levels.

Expression of cardiovascular disease nucleic acid molecules can also be determined using protein measurement methods to determine expression of SEQ ID NOs: 2, 4, 6, 8, and/or 10, e.g., by determining the expression of polypeptides encoded by SEQ ID NOs: 1, 3, 5, 7, and/or 9, respectively. Preferred methods of specifically and quantitatively measuring proteins include, but are not limited to: mass spectroscopy-based methods such as surface enhanced laser desorption ionization (SELDI; e.g., Ciphergen ProteinChip System), non-mass spectroscopy-based methods, and immunohistochemistry-based methods such as 2-dimensional gel electrophoresis.

SELDI methodology may, through procedures known to those of ordinary skill in the art, be used to vaporize microscopic amounts of tumor protein and to create a "fingerprint" of individual proteins, thereby allowing simultaneous measurement of the abundance of many proteins in a single sample. Preferably SELDI-based assays may be utilized to characterize cardiovascular conditions as well as stages of such conditions. Such assays preferably include, but are not limited to the following examples. Gene products discovered by RNA microarrays may be selectively measured by specific (antibody mediated) capture to the SELDI protein disc (e.g., selective SELDI). Gene products discovered by protein screening (e.g., with 2-D gels), may be resolved by "total protein SELDI" optimized to visualize those particular markers of interest from among SEQ ID NOs: 1, 3, 5, 7, and/or 9. Predictive models of tumor classification from SELDI measurement of multiple markers from among SEQ ID NOs: 1, 3, 5, 7, and/or 9 may be utilized for the SELDI strategies.

The use of any of the foregoing microarray methods to determine expression of cardiovascular disease nucleic acids can be done with routine methods known to those of ordinary skill in the art and the expression determined by protein measurement methods may be correlated to predetermined levels of a marker used as a prognostic method for selecting treatment strategies for cardiovascular disease patients.

The invention will be more fully understood by reference to the following examples. These examples, however, are merely intended to illustrate the embodiments of the invention and are not to be construed to limit the scope of the invention.

EXAMPLES

Example 1

Experimental Protocols: Materials and Methods

Mechanical Strain Device

Experiments of mechanically overloading cardiomyocytes have generally been performed by stretching cells with no control of the cardiac cycle, an approach that does not allow distinction between mechanical overload in contraction versus relaxation. In the present study, we designed and constructed a unique experimental system that allows precisely controlled mechanical strains as well as electrical pacing in cultured cardiomyocytes, to investigate, inter alia, how cardiomyocyte mechanotransduction is regulated by the cardiac cycle, and identify genes that are involved in such regulation.

The Pacing-Strain Device. The approach to mechanical stimulation used an apparatus that has multiple platens that contact the underside of silicone elastomer membranes to apply a spatially isotropic biaxial strain profile to the membrane (Schaffer J L, et al., *J Orthop Res,* 1993, 12:709-719; and U.S. Provisional Patent application 60/144,134 filed on Jul. 16, 1999 entitled "AN APPARATUS FOR STUDYING MYOCARDIAL MECHANICAL OVERLOAD HYPERTROPHY AND USES THREFOR, by Richard T. Lee. Six individual 78 mm membranes can be stretched at once with varying amplitudes of strain by controlling displacement of each platen with a stepper motor. Measured Green strains are accurate to ~±0.25% at strains from 1-14% (Cheng G C, et al., *Circ Res,* 1997, 80:28-36; Brown T D, *J Biomechanics,* 2000, 33:3-14). Throughout this study, 8% biaxial strain was used.

To control the timing of mechanical strain relative to the cardiac cycle, the computer paced each dish electrically, and controlled: the phase between the mechanical strain and the electrical impulse, the electrical impulse duration, and the voltage of the impulse. In addition, the electrical impulses had alternating polarity to minimize electrochemical effects such as pH gradients at the electrodes. The two outputs were each connected to a single set of electrodes in each dish. The dishes were paced in parallel with a resistance of approximately 500 ohms per dish.

The positive and negative voltage sources were provided by two power supplies (6545A, Hewlett Packard Company, Palo Alto, Calif.). The control circuit was divided into two parts: a high voltage circuit and a low voltage or digital signal circuit. The high voltage circuit was a gate that switched the output based on the input signal. The low voltage circuit accepted two control signals from the computer and accepted the pulse width from a variable resistor, which controlled both the positive and negative voltage gates. The low voltage circuit allowed a voltage pulse between 0-120V DC amplitude and 2-37 ms duration. Lights provided continuous monitoring of the pulses, and the timing of the circuits and calibration were validated by oscilloscope.

The electrodes for each dish were two arc-shaped $AgCl_2$ wire electrodes at the base of the inner surface of the dish, just above the deformable membrane. The electrodes were premade, ethanol-sterilized, and placed into the dish just prior to each experiment to minimize potential toxicity from silver. Using this method no cellular death or detachment was observed in 24 hr experiments. Each arc was 120 degrees; we performed a two dimensional finite element analysis to estimate the uniformity of the potential field with this configuration. These calculations estimate a spatial variation in the potential field of {root mean square}=29%. Thus, this system provides highly uniform biaxial mechanical strain, with a relatively small variation in the voltage field.

Mechanical stimulation protocols. We imposed strain only during first third of the cardiac cycle by electrical stimulation for strain imposed during the "systolic phase", and only during one third of the cardiac cycle in the relaxation phase for strain imposed during "diastolic phase," respectively. Conditions used in this study were: (1) control; (2) strain, no pacing; (3) pacing, no strain; (4) strain imposed during systolic phase; and (5) strain imposed during diastolic phase.

Neonatal rat ventricular myocytes (NRVM) from 1-day old Sprague-Dawley rats were isolated by previously described methods (Springhorn J P, and Claycomb W C., *Biochem J,* 1989; 258:73-78; Arstall M A, et al., *J Mol Cell Cardiol,* 1998, 30:1019-25). NRVM were plated on the coated membrane dish at a density of 2,000,000 cells/dish in DMEM containing 7% FCS and incubated 24 h. Approximate cell confluence was 85-90%. NRVM were then made quiescent by washing with 10 ml of Hanks' balanced salt solution (HBSS, 138 mM NaCl, 5.3 mM KCl, 4.0 mM $NaHCO_3$, 1.3 mM $CaCl_2$, 0.5 mM $MgCl_2$, 0.4 mM $MgSO_4$, 0.4 mM $KH_2PO_4$, 0.3 mM $Na_2HPO_4$, 5.6 mM glucose; Life Technologies, Inc., Rockville, Md.) twice and incubating with 26 ml of DMEM containing 0.2% FCS for 48-72 hours.

In these cell culture conditions, cells beat at 40-60 beats/minute. At this rate, we have observed negligible competition when pacing at a rate of 70 beats/minute. We performed trial capture experiments; nine locations on each dish were sampled. Capture efficiency was similar at all locations, and maximal capture occurred at 60 V and above with 10 ms of pulse width. Therefore, a voltage of 70 V with 10 ms of impulse duration at a rate of 1.2 Hz (70 beats/minute) was selected. Under these conditions we did not observe partial cell detachment.

Transcriptional Profiling. The DNA microarray experiment was performed with rat neonatal cardiac myocytes cultured on fibronectin-coated membranes with serum-free medium for 48 hours. Cells were deformed with an 8% deformation imposed only during systole for a period of 30 minutes, and RNA was prepared after 6 hours of subsequent no strain conditions and no pacing conditions. This time point was based upon previous studies demonstrating that the gene tenascin (positive control for cardiomyocytes) is induced at this time period. The DNA microarray hybridization experiment was performed using the Affymatrix GeneChip RGU34A (Affymetrix, Inc., Santa Clara, Calif.). Data were analyzed using Affymatrix software.

Northern Analyses. The cDNA clones for differentially expressed genes were obtained by PCR using the GenBank sequences. Each clone was sequenced from both 5' and 3' ends to confirm identity. Positive elements in the DNA microarray were confirmed by Northern blot hybridization analysis in at least three independent experiments using three different sources of NRVMs. Total RNA was isolated by the guanidium thiocyanate and phenol chloroform method (Chomcyznski, et al., *Anal. Biochem.,* 1987, 162:156-159). For Northern blotting, 15 μg RNA was loaded on a 1.0% agarose-formaldehyde gel (2.0 mol/l), transferred to a nylon membrane (Amersham Pharmacia Biotech AB, Piscataway, N.J.), and UV cross-linked with a UV Stratalinker (Stratagene, Inc., La Jolla, Calif.). Each probe was hybridized with ExpressHyb solution (Clontech Labs., Inc., Palo Alto, Calif.) at 68° C. for 1 hour. The membrane was washed with 2×SSC, 0.05% SDS solution for 30 to 40 minutes and three times at room temperature and 0.1×SSC, 0.1% SDS solution with continuous shaking at 50° C. for 40 minutes. The membrane was exposed to film at −80° C., and radiographs were scanned and analyzed with Optimas 5.0 software (Optimas Co./Media Cybernetics, Silver Springs, Md.). Densitometric units were normalized to the ethidium-stained 28S ribosomal subunit on the membrane.

Results. FIG. 1 shows the timecourne (early, left; late, right) of the induction of Fit-1 mRNA expression by 8% cyclic mechanical strain in neonatal cardiac myocytes in culture. Maximal induction occurs at 3 hours and is sustained for 15 hours.

Figure 2:
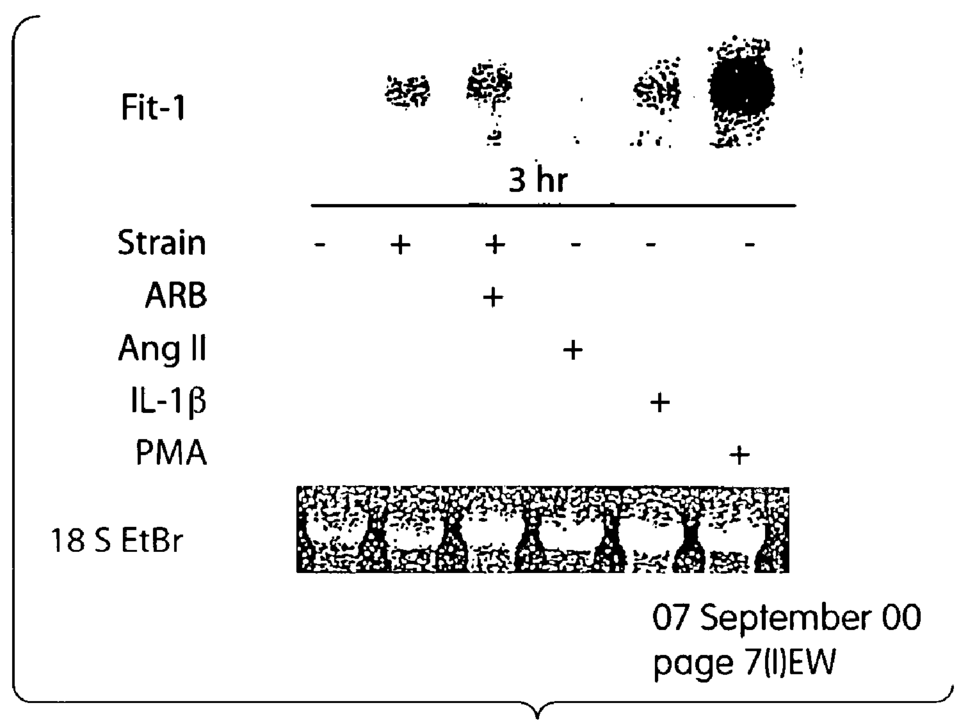
FIG. 2 depicts by a Northern Blot the effects of 8% cyclic mechanical strain, angiotensin receptor blockade, angiotensin II, IL-1b, and phorbal ester, on the expression of Fit-1 in cultured cardiac myocytes over the course of time.

FIG. 2 shows the effects of 8% mechanical strain, angiotensin receptor blockade (ARB, CP-19116, 100 nM), angiotensin II (Ang II, 50 nM), interleukin-1β (IL-1β, 10 ng/ml), and phorbal ester (Pma, 200 nM) for 3 hours on the induction of Fit-1 mRNA expression in cultured neonatal rat cardiac myocytes. The induction of Fit-1 mRNA expression by strain was not blocked by angiotensin receptor blockade; furthermore, treatment with angiotensin II did not induce Fit-1 mRNA expression. Treatment with both IL-1β and PMA were associated with an induction of Fit-1 mRNA expression in the absence of mechanical strain.

Figure 3:
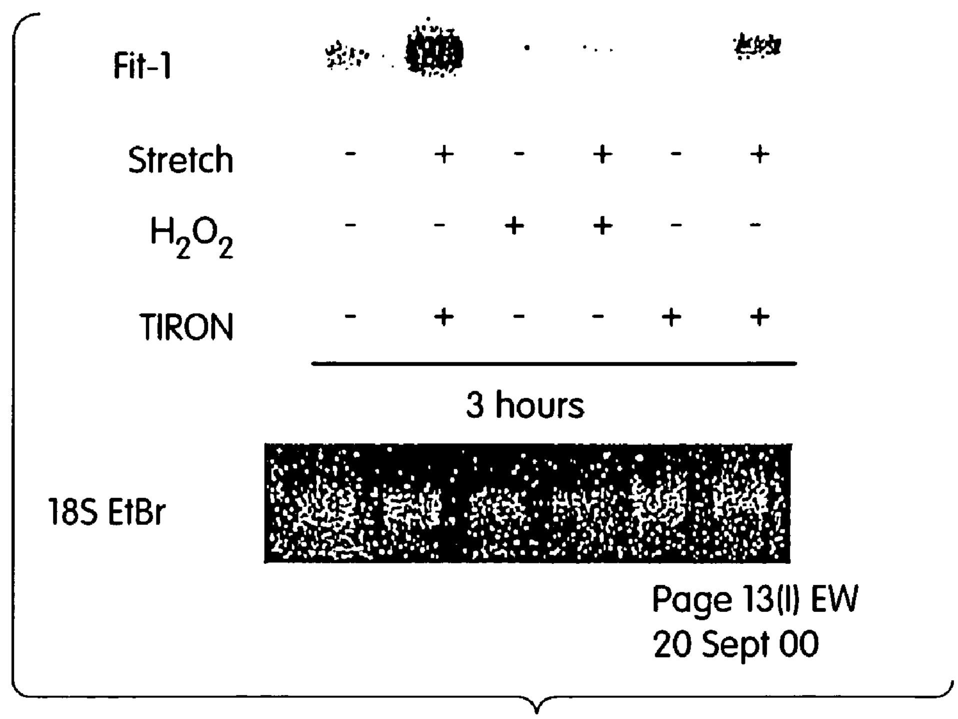
FIG. 3 depicts by a Northern Blot the effects of 8% cyclic mechanical strain, hydrogen peroxide, and TIRON, on the expression of Fit-1 in cultured cardiac myocytes over the course of time.

FIG. 3 shows the effects of 8% mechanical strain, hydrogen peroxide ($H_2O_2$, 100 uM) and the antioxidant, TIRON (10 mN) on the iduction of Fit-1 mRNA expression. Unlike the mRNA expression of the mechanically induced Tenascin-C gene which is induced by $H_2O_2$ in the absence of mechanical strain and blocked by TIRON, $H_2O_2$ does not induce Fit-1 in the absence of strain and blocks the strain-induced induction of Fit-1. TIRON slightly attenuated the mRNA expression of Fit-1 in the absence and presence of strain.

Figure 4:
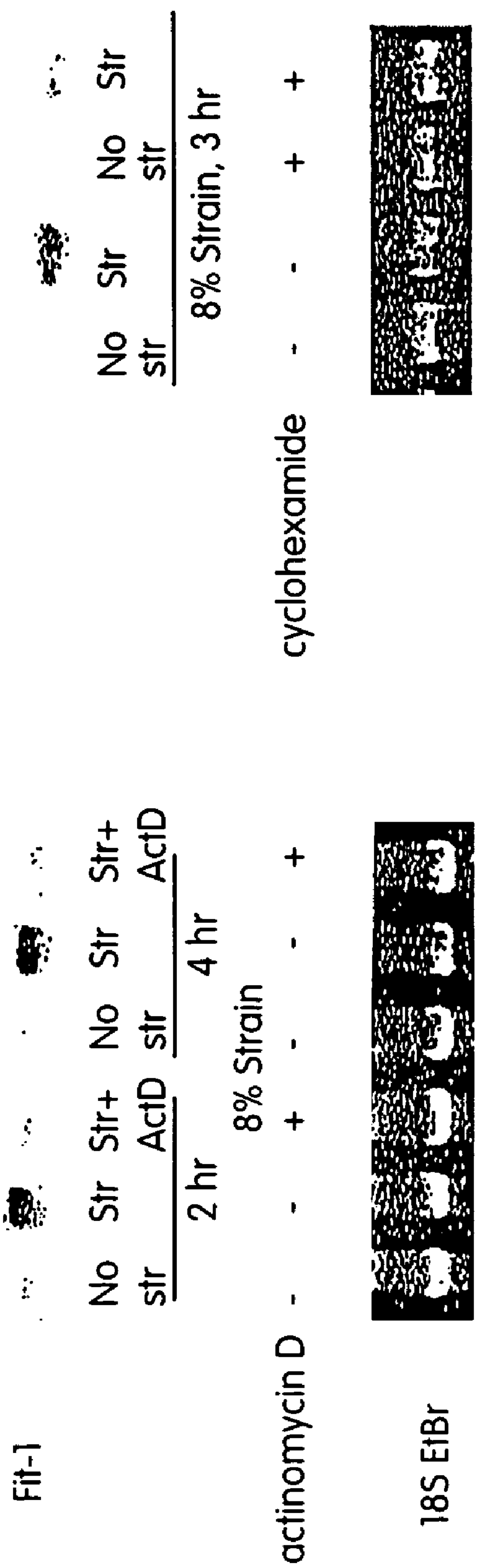
FIG. 4 depicts by a Northern Blot the effects of actinomycin D and cyclohexamide on the induction of Fit-1 expression during an 8% cyclic mechanical strain on cardiac myocytes over the course of time.

FIG. 4 shows the effects of actinomycin D (5 μg/ml, left) and cyclohexamide (10 μg/ml, right) on the induction of Fit-1 mRNA expression by 8% mechanical strain. Actinomycin D and cyclohexamide were applied during mechanical strain. Actinomycin D blocked the induction of Fit-1 mRNA expression at both 2 and 4 hours suggesting that the induction of Fit-1 in response to strain is due to increased transcription of Fit-1. The protein synthesis inhibitor, cyclohexamide blocked the induction of Fit-1 mRNA expression in response to strain suggesting that new protein synthesis is required for the induction of Fit-1 mRNA expression.

Figure 5:
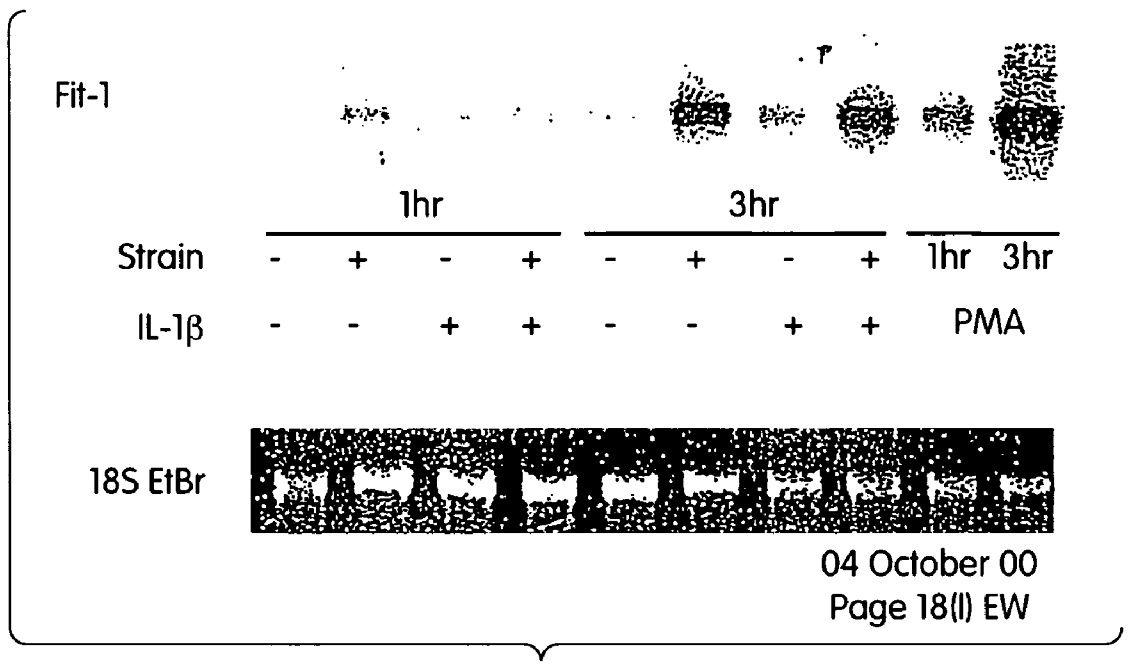
FIG. 5 depicts by a Northern Blot the effects of 8% cyclic mechanical strain alone and in combination with IL-1b, and phorbal ester in the absence of strain, on the expression of Fit-1 in cultured cardiac myocytes over the course of time.

FIG. 5 shows the effects of 8% mechanical strain alone and in combination with interleukin-1β (IL-1β, 10 ng/ml), and phorbal ester in the absence of strain (PMA, 100 ng/ml) on Fit-1 mRNA expression in cultured neonatal cardiac myocytes. Both IL-1β and mechanical strain alone induced Fit-1 mRNA expression but the induction of Fit-1 by mechanical strain in the presence of IL-1β was not futher increased suggesting that mechanical strain and IL-1β do not act in a synergistic or additive manner on the induction of Fit-1. The strongest induction of Fit-1 mRNA expression is seen with PMA. The rank order potency for the induction of Fit-1 mRNA expression is PMA>strain>IL-1β.

Figure 6:
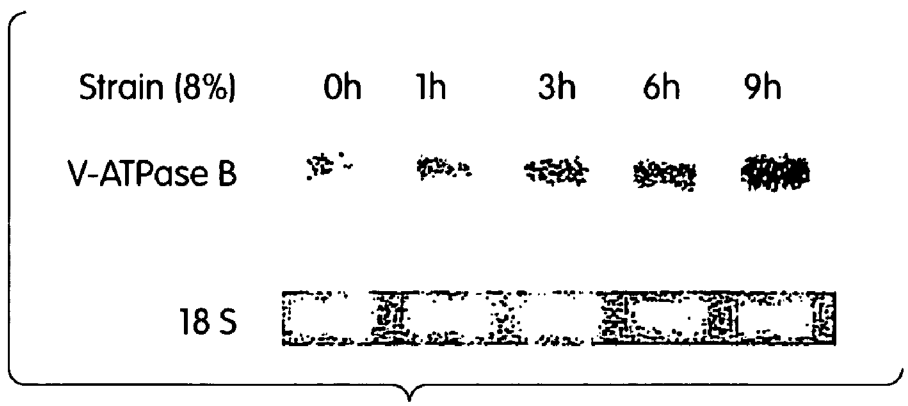
FIG. 6 depicts by a Northern Blot the effects of an 8% cyclic mechanical strain on the expression of vacuolar ATPase in cultured cardiac myocytes over the course of time.

FIG. 6 shows neonatal rat cardiac myocytes were exposed to 8% strain for 0, 1, 3, 6, 9, hours. Total RNA was isolated using RNeasy kit. Five μg of total RNA were size-separated on 1% agarose-formaldehyde gel and transferred to nylon membrane. After cross-linking with UV light, membrane was hybridized with $^{32}$P-labeled probe specific for V-ATPase B subunit. The membrane was then exposed to x-ray film for 3 hours at −80° C. with an intensifying screen.

Example 2

Introduction:

Cytokines and Cardiac Injury. Stress-activated cytokines participate in many forms of cardiac injury and pathophysiological conditions, the most characterized ones being tumor necrosis factor-α, interleukin-1 and interleukin-6. These molecules are not constitutively expressed in the normal heart but are rapidly induced during ischemia and reperfusion or upon hemodynamic overloading, suggesting that they play an important role in the initial myocardial response to stress, injury or growth stimuli (Mann D L, *Cytokine and Growth Factor Reviews.* 1996; 7:341-354; St. John Sutton M G, et al. *Circulation.* 2000;101:2981-2988). However, cytokines have also been shown to be stably expressed in pathologic myocardial conditions including ischemic heart disease and heart failure and are associated with a poor prognosis (Pulkki K J, et al. *Annals of Medicine.* 1997; 29:339-343; Kubota T, et al *Proc Natl Acad. Sci.* 1998;95:6930-6935; Aukrust P, et al. *Am J Cardiol* 1999;83:376-382; MacGowan Ga., et al. *Am J Cardiol* 1997;79:1128-1132; Roig E, et al. *Am J Cardiol* 1998;688-690; Tsutamoto T, et al. *J Am Coll Cardiol* 1998; 31:391-398; Prabhu S D, et al. *Circulation.* 2000;101:2103-2109; Murray D R, et al. *Annu Rev Immunol.* 2000;18:451-494).

Interleukin-1 signaling through the interleukin-1 receptor is an early event in inflammatory cytokine signaling in many different systems (Trehu E G., *Clin Cancer Res.* 1996; 8:1341-51). In cardiac injury, interleukin-6 is produced by cardiac myocytes secondary to stimulation with interleukin-1, tumor necrosis factor-α, or lipopolysaccharide and has been detected in the post-ischemic lymph during reperfusion of ischemic myocardium (Gwechenberger M, et al. *Circulation* 1999;99:546-551). Recently recognized is the potential expression of counteracting anti-inflammatory cytokines in cardiac disease secondary to interleukin-1 signaling. Interleukin-4 and interleukin-10 can suppress the synthesis of tumor necrosis factor-α and enhance the release of soluble tumor necrosis factor receptors, which are ligand sinks for tumor necrosis factor (Joyce D A., 1994; *Eur. J. Immunol* 11:2699-705). Interleukin-10 is increased in patients with heart failure (Yamaoka M, et al. *Jpn Circ J.* 1999;63:951-956) and interleukin-10 serum levels are increased when tumor necrosis factor-α serum levels are increased in patients with dilated cardiomyopathy (Ohtsuka T, et al. *J Am Coll Cardiol.* 2001;37:412-417).

T1/ST2 (fit-1): A Novel Mechanically Induced Receptor. We have identified a novel potential stress-activated signaling pathway in the heart: regulation of the induction of an interleukin-1 family member gene, T1/ST2. Little is known of the induction, signaling and function of T1/ST2 in any cell type and T1/ST2 was shown in separate areas of investigation to have two seemingly unrelated functions. One of these is growth regulation and the other is immune modulation. Both compensatory hypertrophic growth and immune/inflammatory modulation are involved in the pathophysiology of cardiovascular diseases.

Growth. The T1/ST2 gene was first identified by its induction following serum stimulation of resting mouse 3T3 fibroblasts, suggesting that the T1/ST2 gene participates in growth regulation (Tominaga S., FEBS Letters 1989;258:301-304). The same group later identified a longer transcript consisting of transmembrane and cytoplasmic domains homologous to the full-length interleukin-1 receptor (Yanagisawa K, et al. *FEBS Letters.* 1993;318:83-87).

Immunity. T1/ST2 is expressed on T helper-2, but not T helper-1, cells of the adaptive immune system, which produce interleukin-4, interleukin-5 and interleukin-10 (Yanagisawa K I, et al. *J. Biochem.* 1997;121:95-103; Coyle A J, et al. *J Exp Med.* 1999;190:895-902). T helper-2 cells mediate beneficial responses to infection, but are detrimental in the development of allergy and asthma. There is a strong correlation between expression of T1/ST2 and interleukin-4 production on T helper-2 cells (Coyle A J, et al. *J Exp Med.* 1999;190:895-902). T1/ST2 plays a critical role in differentiation to and activation of T helper-2 but not T helper-1 cells (O'Neill L A J, et al. *Immunology Today.* 2000;21:206-209).

Inhibition of T1/ST2 signaling attenuated T helper 2-mediated induction of eosinophil inflammatory responses in lung and inhibited cytokine secretion from T helper-2 cells without modifying interferon-gamma secretion from T helper-1 cells (Coyle A J, et al. *J Exp Med.* 1999;190:895-902). These studies indicate that expression of T1/ST2 can alter the cytokine profile in favor of expression of interleukin-4, interleukin-5 and interleukin-10. Interleukin-10 has recently been shown to have anti-inflammatory effects in the setting of cardiac injury (Ohtsuka T, et al. *J Am Coll Cardiol.* 2001;37:412-417). Similarly, the absence of T1/ST2 expression could result in a shift towards interferon-gamma expression, which may be deleterious following myocardial injury.

Taken together, the involvement of T1/ST2 in growth responses and immune function coupled with the clinical recognition of the role of cytokines in the inflammatory response to ischemia/reperfusion are suggestive that T1/ST2 activation is a growth- or stress-activated signaling pathway that contributes to myocardial growth and remodeling.

Phenotype of T1/ST2 Null Mice. (Townsend M J, et al. *J Exp Med.* 2000;191:1069-1075). The absence of T1/ST2 in T1/ST2 null mice does not compromise their basal immune function in the absence of immune challenge. However, T1/ST2 null mice have an impaired ability to generate IL-4, IL-5, and IL-10, but not IFN-γ (a Th1 cytokine) and to generate a T helper-2 inflammatory response during eosinophilic infiltration in the lung (a Th2 response).

We have begun to study the induction of T1/ST2 in cardiac myocytes and its involvement in survival/death signaling within the context of the myocyte signaling pathways. Preliminary studies presented below show that T1/ST2 is induced in cardiac myocytes in response to interleukin-1 and mechanical strain and that the induction of T1/ST2 by interleukin-1 may be dependent on NF-κB activation. T1/ST2 mRNA is also induced in human adult vascular smooth muscle cells in response to interleukin-1. T1/ST2 protein is expressed in the mouse heart early after myocardial ischemia in vivo as well as in human aorta tissue from patients with unstable plaque.

Figure 8:
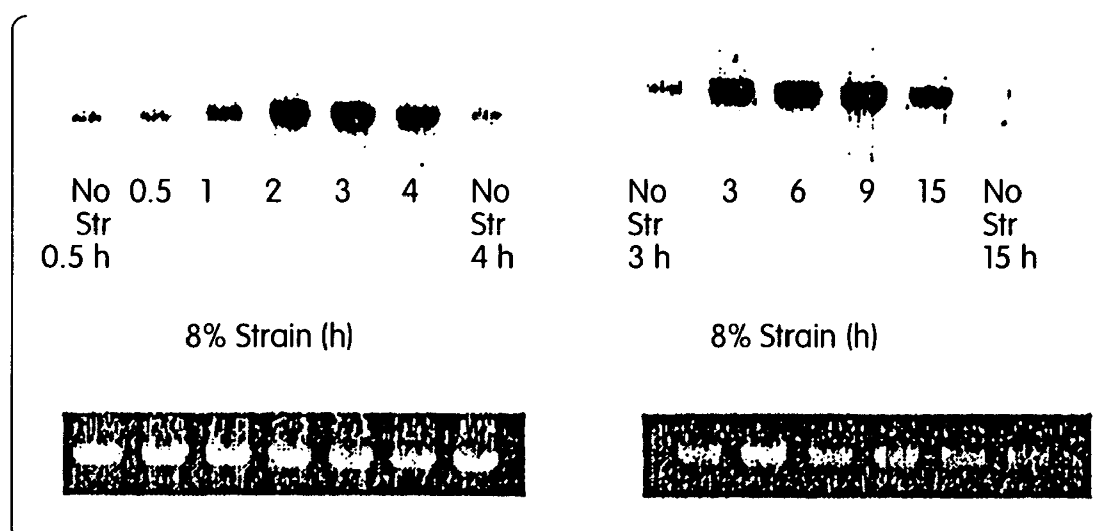
FIG. 8 depicts early (left) and late (right) time course of the mRNA induction of T2/ST2 by mechanical strain in cardiac myocytes. Maximal induction occurs at 3 hours, is sustained for 9 hours and declines by 15 hours. Top panels, T1/ST2 RNA; bottom panels, ethidium bromide. No str, no strain.

Results:

IN VITRO STUDIES. The following studies demonstrate the induction of T1/ST2 by mechanical strain and interleukin-1, possibly through activation of NF-κB. Both transcripts of T1/ST2 (that is, Fit-1S and Fit-1M) are induced by strain in cardiac myocytes. T1/ST2 mRNA is induced by mechanical strain in cultured neonatal cardiac myocytes (FIG. 8).

T1/ST2 mRNA is induced by mechanical strain in cultured neonatal cardiac myocytes. Neonatal rat ventricular myocytes were isolated by collagenase digestion, plated on fibronectin-coated silicone membrane dishes at a density of 3.5 million cells/dish in 13 ml media as previously described (Yamamoto K, et al. *J. Biol. Chem.* 1999;274:21840-21846). This technique yields cultures with ≧95% myocytes. Mechanical deformation was applied using a device that provides uniform biaxial cyclic strain as previously described (Yamamoto K, et al. *J. Biol. Chem.* 1999;274:21840-21846). RNA was extracted (Qiagen) and Northern blotting was performed using as a probe a $^{32}$P-labelled 600 bp PCR fragment specific to rat T1/ST2. Maximal induction occurs at 3 hours, is sustained for 9 hours and declines by 15 hours.

Figure 9:
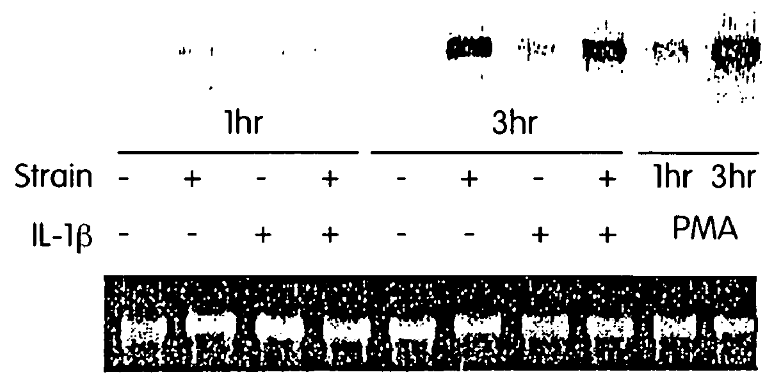
FIG. 9 depicts mRNA induction of T1/ST2 by mechanical strain (8%), interleukin-1 (10 ng/ml) and phorbol ester (PMA, 200 nM) at 1 and 3 hours. PMA>strain>IL-1. Top panel, T1/ST2 mRNA, bottom panel, ethidium bromide.

Both interleukin-1β and mechanical strain each induce T1/ST2 RNA in cardiac myocytes (FIG. 9). Shown is the induction of T1/ST2 by interleukin-1 and strain. We also found that the induction of T1/ST2 by mechanical strain in the presence of interleukin-1β was not further increased suggesting that interleukin-1 does not sensitize myocytes to the effects of mechanical strain (or vice versa) on the induction of T1/ST2. The 1 hour time point was included in the event that induction by strain is saturated at 3 hours and therefore masks an additive effect of interleukin-1β. Shown in the two right lanes are the effects of phorbol ester (PMA) at 1 and 3 hours. The rank order potency for the induction of T1/ST2 mRNA expression is PMA>strain>interleukin-1β. Since interleukin-1β signals through NF-κB and PMA through PKC these results suggest that NF-κB and PKC activation both participate in the is induction of T1/ST2.

Figure 10:
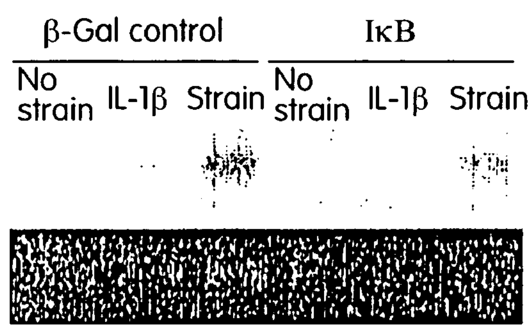
FIG. 10 depicts T1/ST2 may be a gene induced by NF-κB activation during IL-1/IL-receptor signaling in cardiac myocytes. IL-1 and strain induced T1/ST2 mRNA in the presence of infection with control adenovirus (left). With infection of IκB adenovirus (right), which decreases NF-κB DNA binding activity, the IL-1 induction of T1/ST2 was blocked. The strain induction of T1/ST2 was partially blocked by IκB infection suggesting another pathway for induction of T1/ST2 by strain. Top panel, T1/ST2 mRNA; bottom panel, ethidium bromide.

T1/ST2 may be a NF-κB target gene in cardiac myocytes through interleukin-1/interleukin-1 receptor signaling (FIG. 10). Previously reported by us (Yamamoto K, et al. *J. Biol. Chem.* 1999;274:21840-21846), mechanical strain of cardiac myocytes activates NF-κB. To investigate the role of NF-κB in interleukin-1β and strain induction of T1/ST2 RNA, we overexpressed IκBα, which decreases NF-κB DNA binding activity. Cultured cardiac myocytes were infected with IκBα overexpression adenovirus vector or with β-galactosidase control vector and exposed for 4 hours to 8% cyclic mechanical strain or interleukin-1 (10 ng/ml). RNA was analyzed by Northern blotting with $^{32}$P-labeled Fit-1 cDNA probe. Ectopic expression of IκBα blocked interleukin-1β induction of T1/ST2-1 mRNA and partially blocked strain induction of T1/ST2 mRNA expression when compared with T1/ST2 induction in cells treated with the β-galactosidase control vector. These results suggest that T1/ST2 is an early, NF-κB target gene through interleukin-1/interleukin-1 receptor signaling. In contrast, pathways in addition to NF-κB activation may be involved in the induction of T1/ST2 RNA by mechanical strain. T1/ST2 mRNA is also induced by interleukin-1 but not PMA or tumor necrosis factor (TNF) in human adult vascular smooth muscle cells.

In addition to the above-noted results, we have shown that T1/ST2 is induced secondary to NF-κB activation by interleukin-1 and NF-κB is linked to cardiac myocyte survival. Further in vitro studies are performed to confirm that T1/ST2 activation is linked to cell growth and survival.

Figure 11:
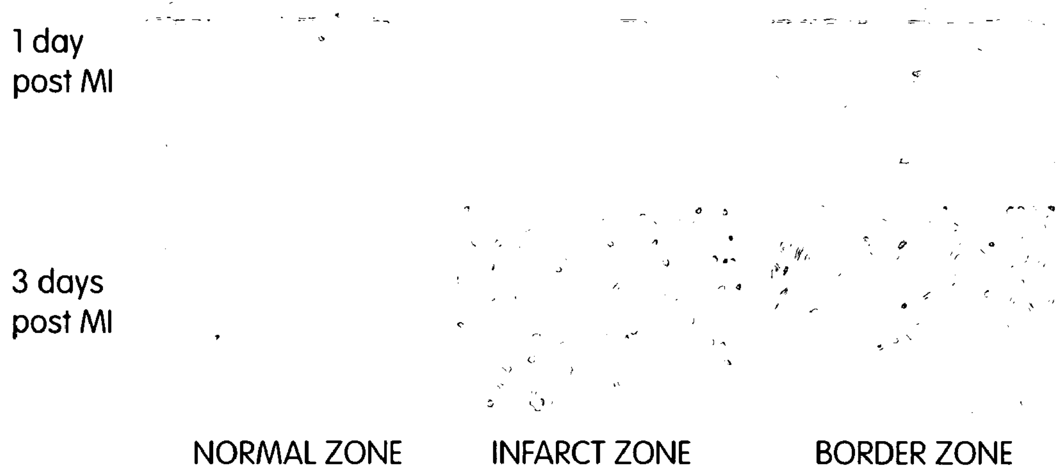
FIG. 11 shows expression of T1/st2 protein following myocardial inftration in mice by immunohistohemistry at 1 day but not 3 days after inffarction. 40× magnification.

IN VIVO STUDIES. In vivo Expression of T1/ST2 Protein in Myocardial Infarction in Mice. FIG. 11 shows protein expression of T1/ST2 using immunohistochemistry in paraffin sections of mouse hearts 1 and 3 days post-infarction. T1/ST2 protein was visualized by DAB staining. This antibody (Morwell Diagnostics) does not distinguish between the two isoforms of T1/ST2. Positive staining (brownish color) is seen 1 day post-infarction (post-MI) in the normal, infarct and border zones but not at 3 days post-MI. These results suggest that ST2 protein is rapidly expressed in response to myocardial injury during the early phase of post-infarction remodeling before the migration of macrophages into the infarct and border zones (see 3 days post-MI). Magnification: 40×.

In addition to the above, we are generating an operational colony of T1/ST2 null mice. Our in vivo studies indicate that T1/ST2 is expressed in the mouse heart following myocardial infarction. The in vivo studies confirm the hypothesis that local cardiac expression of T1/ST2 favorably modifies the process of LV remodeling following ischemia and left ventricular pressure overload. We have also generated adeno-associated viruses to express isoforms of these genes and their effects on null mice are determined.

More recently, we have obtained results which support the utility of the gene/protein called fit-1, or ST-2, as a diagnostic indicator of a cardiovascular condition in humans. We assayed serum levels on 69 patients who participated in the HEART study, a clinical trial of acute myocardial infarction patients. The assay employed a monoclonal assay for the human ST2 protein. The results show that the levels of ST2 correlated with serum creatine phosphokinase levels, which is a standard way of looking at size of heart attack. Also, such levels rapidly decline after the infarct. The levels were: Day 1: 3.8+/−3.3 ng/ml; Day 14: 0.9 +/−0.5; and Day 90: 0.8+/−0.5 and are highly statistically significant. These results also establish that the protein is secreted during heart attacks and can be easily measured, thereby supporting the asserted utility of the invention.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is presented below and is followed by a Sequence Listing.

I claim:

1. A method of diagnosing a cardiovascular condition characterized by increased expression of a Fit-1/ST2 nucleic acid molecule or an expression product thereof, said method comprising:

a) contacting a biological sample from a subject with an agent, wherein said agent specifically binds to said Fit-1/ST2 nucleic acid molecule or an expression product thereof; and b) measuring the amount of bound agent and determining therefrom if the expression of said Fit-1/ST2 nucleic acid molecule or of an expression product thereof is increased relative to a predetermined value, wherein the expression increased relative to a predetermined value is diagnostic of the condition.

2. The method of claim 1, wherein the cardiovascular condition is characterized by mechanical strain, mechanical overload or mechanically-induced deformation in cardiac cells or tissue.

3. The method of claim 1, wherein the cardiovascular condition is selected from the group consisting of myocardial infarction, stroke, arteriosclerosis, and heart failure.

4. The method of claim 1, wherein the cardiovascular condition is cardiac hypertrophy.

5. The method of claim 1, wherein the sample is a biological fluid or a tissue.

6. The method of claim 5, wherein the biological fluid is blood or serum.

7. The method of claim 1, wherein the agent is (i) an isolated nucleic acid molecule that hybridizes to the Fit-1/ST2 nucleic acid molecule or (ii) an antibody that binds the polypeptide encoded by the Fit-1/ST2 nucleic acid molecule, or an antigen-binding fragment of the antibody.

8. The method of claim 7, wherein the nucleic acid or the antibody is labeled with a radioactive label or an enzyme.

9. A method for monitoring a sample of a patient having or to suspected of having cardiovascular condition. comprising:

assaying a sample from the patient for increased expression relative to a predetermined value of (i) a Fit-1/ST2 nucleic acid molecule, or (ii) a polypeptide encoded by the nucleic acid of part (i).

10. The method of claim 9, wherein the step of monitoring comprises contacting the sample with a detectable agent selected from the group consisting of:

(a) an isolated nucleic acid molecule which hybridizes to the nucleic acid molecule of part (i), and (b) an antibody or an antigen binding fragment thereof which binds the polypeptide of part (ii).

11. The method of claim 10, wherein the nucleic acid of part (a) or the antibody of part (b) is labeled with a radioactive label or an enzyme.

12. The method of claim 9, wherein the cardiovascular condition is characterized by mechanical strain, mechanical overload or mechanically-induced deformation in cardiac cells or tissue.

13. The method of claim 9, wherein the cardiovascular condition is selected from the group consisting of myocardial infarction, stroke, arteriosclerosis, and heart failure.

14. The method of claim 9, wherein the cardiovascular condition is cardiac hypertrophy.

15. The method of claim 9, wherein the sample is a biological fluid or a tissue.

16. The method of claim 15, wherein the biological fluid is blood or serum.

* * * * *

UNITED STATES PATENT AND TRADEMARK OFFICE

CERTIFICATE OF CORRECTION

PATENT NO. : 7,432,060 B2
APPLICATION NO. : 10/024607
DATED : October 7, 2008
INVENTOR(S) : Richard T. Lee It is certified that error appears in the above-identified patent and that said Letters Patent is hereby corrected as shown below:

In Claim 9, line 54, please delete “to suspected of having cardiovascular condition.” and insert --suspected of having a cardiovascular condition,--

Signed and Sealed this

Second Day of December, 2008

JON W. DUDAS
*Director of the United States Patent and Trademark Office*

UNITED STATES PATENT AND TRADEMARK OFFICE

CERTIFICATE OF CORRECTION

PATENT NO. : 7,432,060 B2
APPLICATION NO. : 10/024607
DATED : October 7, 2008
INVENTOR(S) : Richard T. Lee It is certified that error appears in the above-identified patent and that said Letters Patent is hereby corrected as shown below:

Column 132, In Claim 9, line 54, please delete "to suspected of having cardiovascular condition." and insert --suspected of having a cardiovascular condition,--

This certificate supersedes the Certificate of Correction issued December 2, 2008.

Signed and Sealed this

Thirtieth Day of December, 2008

JON W. DUDAS
*Director of the United States Patent and Trademark Office*

SEQUENCE LISTING

<160> NUMBER OF SEQ ID NOS: 33

<210> SEQ ID NO 1
<211> LENGTH: 2586
<212> TYPE: DNA
<213> ORGANISM: Rattus norvegicus
<220> FEATURE:
<221> NAME/KEY: mRNA
<222> LOCATION: (1)...(2586)
<223> OTHER INFORMATION: Fit-1S

<400> SEQUENCE: 1

```
gggtagtctg aagagaccag aggaaggagc accaagtagc ctcagggccc tgggtttatt      60
cttcccagcc cttcatctgg gctacactga tttctctttt ggaccctaca tcagacagca     120
cacatcaacc gcctagtgga ctcaccgtta ccttcctgtg ccattgccat cggagagatc     180
tcggccatca atcactagca catgattggc aaatggagaa tggggctttg ggctttggca     240
attctgacag ttcccatgta tttcatagtg acagagggca gaaaaacatc ctggggtcta     300
gaaaacgagg ctttaattgt cagatgcccc caaagaggag gtgcgattaa ccctgtggaa     360
tggtattatt caaatacaaa tgaaagaatt cctactcaaa agagaaatcg gatcttcgtc     420
tcaagagatc gtctgaagtt tctaccagcc aaagtggaag actctgggat ttatacgtgt     480
gttatcagaa gccctgaatc gattaagacc ggatctttga atgtcaccat atataaaaga     540
ccaccaaact gcaaaatccc tgattacatg atgtactcga cagtagatgg atcagataaa     600
aattccaaga taacatgtcc aacaattgcc ttgtataatt ggacagcgcc tgttcagtgg     660
tttaagaact gcaaagctct ccaagggcca aggttcaggg cacacatgtc ctatttgttc     720
attgacaaag tgagtcatgt tgatgaaggt gactacacat gtcgattcac tcacacggag     780
aacggaacca attacattgt gactgccacc agatcattca cagttgaaga aaaaggcttc     840
tctacatttc cagtaattac aaaccctcca cacaactaca cagtggaagt ggaaatagga     900
aaaacagcaa acattgcctg ctcagcttgc tttggcacag cctctcagtt cgttgctgtc     960
ctgtggcaga ttaacaaaac gagaattgga tcttttggca aagcaagaat tcaagaagag    1020
aaaggcccaa ataaaagttc cagcaatggc atgatttgct taacctcact gttaaggata    1080
actggtgtga ccgacaagga cttctccctg aaatatgact gtgtggccat gaaccatcac    1140
ggagtgataa ggcaccccgt aagactgaga aggaaacaac caagtaagga gtgtctctca    1200
caaattgctt gacaaaattg gctgaatttg ctgcaaacca caatcctttt tctcagagga    1260
ctgtgtgtta tagcttggtc ccaggggatt catcatgatc gtgggattag ttggccagtt    1320
tcctcaaatg tgtttttcat gttgagaaag ctccttaaat ctggtctgtc cagaatgttt    1380
ctgtcttcta gaaggactct ctgtcattgt atctttcctc tctctgtttc cccttgtcct    1440
tgttctcctc acggtcctcc ccatcccttc accttccttc acgttctctc tactcttctt    1500
cccttatctc tgggctcctt ctcacctgtt agtggcttct tcagtcaccc tttgcacatg    1560
ctacaaggga cattggtgtt gatactgggt tggaagcagt aataacccta ctgtgtttct    1620
ccctttgtga ctcttgtaac agaaaacaac ttacacatta ggtggatgac caacttgatc    1680
ccattttaaa agagtagaga aaacatgata tttttaccct taacactctc ttatgatact    1740
aaccactgcc tcaatggcaa tacaactaat gtaaaaacat tattttaact tctttcaaat    1800
atcaagaggg tgtggaaggg agagagacac tgactctaag ctcatagtga tatgtggggc    1860
atttattggg attaagatat tgattaaatg attagggtgg gggtacctat tggataccat    1920
```

-continued

```
caagctgtgt cactgcctga agtggtagtt gggatttttt tttggttctg tttgtcttct   1980

ttggtttgtt ttaactatag agaccattct gctcttgaac tcctagagtt ccacctggct   2040

ttgcctctca ggtcctggga ttaaagccat atgtcacctt acccagccag gatgtttctt   2100

gttttggttt caattttaga gcctctggct tgtaagattt ttataaagta gagtttgatt   2160

cataggtggc cagagttgtg actcatagat gggttttagt gaggtcttag gcatccaccc   2220

cttataatgc tgttacccag ggtgactgtg gaccacagca ctgtgttatg agatggtgga   2280

ggtcatggca cattctatag gaaaagagaa gccaagcccc tagtctcacc aggcacaacc   2340

ttgagtcctc actgctctcc tctgccaaca ggaccttttg tccagatttc tgagtattct   2400

ctagttacat ttgtatttga actatatttg tgttatctgt aattctgtat ttgttttgtt   2460

tgtgtgtggt tttgtatttt ccagattatt tttaattcac ctgttgctat tcaaatcaat   2520

gtatctgtac tgcttcatca acacagcctg ttaaataaaa gtcgtgtctg ttgttgttga   2580

atgata                                                              2586
```

<210> SEQ ID NO 2
<211> LENGTH: 336
<212> TYPE: PRT
<213> ORGANISM: Rattus norvegicus
<220> FEATURE:
<221> NAME/KEY: PEPTIDE
<222> LOCATION: (1)...(336)
<223> OTHER INFORMATION: Fit-1S

<400> SEQUENCE: 2

```
Met Ile Gly Lys Trp Arg Met Gly Leu Trp Ala Leu Ala Ile Leu Thr
 1               5                  10                  15

Val Pro Met Tyr Phe Ile Val Thr Glu Gly Arg Lys Thr Ser Trp Gly
            20                  25                  30

Leu Glu Asn Glu Ala Leu Ile Val Arg Cys Pro Gln Arg Gly Gly Ala
        35                  40                  45

Ile Asn Pro Val Glu Trp Tyr Tyr Ser Asn Thr Asn Glu Arg Ile Pro
    50                  55                  60

Thr Gln Lys Arg Asn Arg Ile Phe Val Ser Arg Asp Arg Leu Lys Phe
65                  70                  75                  80

Leu Pro Ala Lys Val Glu Asp Ser Gly Ile Tyr Thr Cys Val Ile Arg
                85                  90                  95

Ser Pro Glu Ser Ile Lys Thr Gly Ser Leu Asn Val Thr Ile Tyr Lys
            100                 105                 110

Arg Pro Pro Asn Cys Lys Ile Pro Asp Tyr Met Met Tyr Ser Thr Val
        115                 120                 125

Asp Gly Ser Asp Lys Asn Ser Lys Ile Thr Cys Pro Thr Ile Ala Leu
    130                 135                 140

Tyr Asn Trp Thr Ala Pro Val Gln Trp Phe Lys Asn Cys Lys Ala Leu
145                 150                 155                 160

Gln Gly Pro Arg Phe Arg Ala His Met Ser Tyr Leu Phe Ile Asp Lys
                165                 170                 175

Val Ser His Val Asp Glu Gly Asp Tyr Thr Cys Arg Phe Thr His Thr
            180                 185                 190

Glu Asn Gly Thr Asn Tyr Ile Val Thr Ala Thr Arg Ser Phe Thr Val
        195                 200                 205

Glu Glu Lys Gly Phe Ser Thr Phe Pro Val Ile Thr Asn Pro Pro His
    210                 215                 220
```

-continued

```
Asn Tyr Thr Val Glu Val Glu Ile Gly Lys Thr Ala Asn Ile Ala Cys
225                 230                 235                 240

Ser Ala Cys Phe Gly Thr Ala Ser Gln Phe Val Ala Val Leu Trp Gln
                245                 250                 255

Ile Asn Lys Thr Arg Ile Gly Ser Phe Gly Lys Ala Arg Ile Gln Glu
            260                 265                 270

Glu Lys Gly Pro Asn Lys Ser Ser Ser Asn Gly Met Ile Cys Leu Thr
        275                 280                 285

Ser Leu Leu Arg Ile Thr Gly Val Thr Asp Lys Asp Phe Ser Leu Lys
    290                 295                 300

Tyr Asp Cys Val Ala Met Asn His His Gly Val Ile Arg His Pro Val
305                 310                 315                 320

Arg Leu Arg Arg Lys Gln Pro Ser Lys Glu Cys Leu Ser Gln Ile Ala
                325                 330                 335


<210> SEQ ID NO 3
<211> LENGTH: 2065
<212> TYPE: DNA
<213> ORGANISM: Rattus norvegicus
<220> FEATURE:
<221> NAME/KEY: mRNA
<222> LOCATION: (1)...(2065)
<223> OTHER INFORMATION: Fit-1M

<400> SEQUENCE: 3

aggagaaaag actgggatat gctagcttgc tagctccagc aagcggcggt atgcgcggtc     60

tttaaaatag acagacatag aggctttggg ggagaggaag aagtgcctgg gatgaagaag    120

agatgcacct acccggcagg ggtgaaatcc caagctacac tgatttctct tttggaccct    180

acatcagaca gcacacatca accgcctagt ggactcaccg ttaccttcct gtgccattgc    240

catcggagag atctcggcca tcaatcacta gcacatgatt ggcaaatgga gaatggggct    300

ttgggctttg gcaattctga cagttcccat gtatttcata gtgacagagg gcagaaaaac    360

atcctggggt ctagaaaacg aggctttaat tgtcagatgc cccaaagag gaggtgcgat     420

taaccctgtg gaatggtatt attcaaatac aaatgaaaga attcctactc aaaagagaaa    480

tcggatcttc gtctcaagag atcgtctgaa gtttctacca gccaaagtgg aagactctgg    540

gatttatacg tgtgttatca gaagccctga atcgattaag accggatctt tgaatgtcac    600

catatataaa agaccaccaa actgcaaaat ccctgattac atgatgtact cgacagtaga    660

tggatcagat aaaaattcca agataacatg tccaacaatt gccttgtata attggacagc    720

gcctgttcag tggtttaaga actgcaaagc tctccaaggg ccaaggttca gggcacacat    780

gtcctatttg ttcattgaca aagtgagtca tgttgatgaa ggtgactaca catgtcgatt    840

cactcacacg gagaacggaa ccaattacat tgtgactgcc accagatcat tcacagttga    900

agaaaaaggc ttctctacat ttccagtaat tacaaaccct ccacacaact acacagtgga    960

agtggaaata ggaaaaacag caaacattgc ctgctcagct tgctttggca cagcctctca   1020

gttcgttgct gtcctgtggc agattaacaa aacgagaatt ggatcttttg gcaaagcaag   1080

aattcaagaa gagaaaggcc caaataaaag ttccagcaat ggcatgattt gcttaacctc   1140

actgttaagg ataactggtg tgaccgacaa ggacttctcc ctgaaatatg actgtgtggc   1200

catgaaccat cacggagtga taaggcaccc cgtaagactg agaaggaaac aaccaattga   1260

ccaccaaagc acctactaca tagttgccgg atgtagttta ttgctaatgt ttatcaatgt   1320

cttggtgata gtcttaaaag tgttctggat tgaggttgct ctgttctgga gagatataat   1380
```

```
ggcaccttac aaaacccaga atgatggaaa gctctatgat gcttacatca tttaccctcg   1440

ggtcttccgg ggcagcgcag cagggaccgg ctctgtggag tactttgttc actacactct   1500

gcccgacgtt ctcgaaaata aatgtggcta caagttgtgc atttacggga gagacctgct   1560

gcctgggcaa gatgcggcca ctgtggtgga aagcagtatc cagaatagta gacggcaagt   1620

gtttgtcctg gcccctcaca tgatgcacag caaagagttt gcctatgagc aggagatcgc   1680

cctgcacagc gccctcatcc agaacaactc caaggtgatt ctgattgaaa tggagcctat   1740

gggtgaggca agccgactgc agcttgggga tctgcaagat tctctccagc atcttgtgaa   1800

aatgcagggg accatcaagt ggagggaaga ccacgtggcc gacaaacagt ctctaagctc   1860

caaattctgg aagcatgtga gataccaaat gccagtcccg aaaagacccc ccaagatggc   1920

tctgttgcc gctccgttga gtggcaaggt gtgcttggac ctgaaacact tttgagtcgt    1980

gacttgcct actcagagct ggggaatccc agcagtaggc cccagaagtg aaggtgtgaa    2040

acttgaaat gccaagggtg gggcc                                          2065
```

```
<210> SEQ ID NO 4
<211> LENGTH: 566
<212> TYPE: PRT
<213> ORGANISM: Rattus norvegicus
<220> FEATURE:
<221> NAME/KEY: PEPTIDE
<222> LOCATION: (1)...(566)
<223> OTHER INFORMATION: Fit-1M

<400> SEQUENCE: 4

Met Ile Gly Lys Trp Arg Met Gly Leu Trp Ala Leu Ala Ile Leu Thr
 1               5                  10                  15

Val Pro Met Tyr Phe Ile Val Thr Glu Gly Arg Lys Thr Ser Trp Gly
            20                  25                  30

Leu Glu Asn Glu Ala Leu Ile Val Arg Cys Pro Gln Arg Gly Gly Ala
        35                  40                  45

Ile Asn Pro Val Glu Trp Tyr Tyr Ser Asn Thr Asn Glu Arg Ile Pro
    50                  55                  60

Thr Gln Lys Arg Asn Arg Ile Phe Val Ser Arg Asp Arg Leu Lys Phe
65                  70                  75                  80

Leu Pro Ala Lys Val Glu Asp Ser Gly Ile Tyr Thr Cys Val Ile Arg
                85                  90                  95

Ser Pro Glu Ser Ile Lys Thr Gly Ser Leu Asn Val Thr Ile Tyr Lys
            100                 105                 110

Arg Pro Pro Asn Cys Lys Ile Pro Asp Tyr Met Met Tyr Ser Thr Val
        115                 120                 125

Asp Gly Ser Asp Lys Asn Ser Lys Ile Thr Cys Pro Thr Ile Ala Leu
    130                 135                 140

Tyr Asn Trp Thr Ala Pro Val Gln Trp Phe Lys Asn Cys Lys Ala Leu
145                 150                 155                 160

Gln Gly Pro Arg Phe Arg Ala His Met Ser Tyr Leu Phe Ile Asp Lys
                165                 170                 175

Val Ser His Val Asp Glu Gly Asp Tyr Thr Cys Arg Phe Thr His Thr
            180                 185                 190

Glu Asn Gly Thr Asn Tyr Ile Val Thr Ala Thr Arg Ser Phe Thr Val
        195                 200                 205

Glu Glu Lys Gly Phe Ser Thr Phe Pro Val Ile Thr Asn Pro Pro His
    210                 215                 220

Asn Tyr Thr Val Glu Val Glu Ile Gly Lys Thr Ala Asn Ile Ala Cys
```

-continued

```
225                 230                 235                 240

Ser Ala Cys Phe Gly Thr Ala Ser Gln Phe Val Ala Val Leu Trp Gln
                245                 250                 255

Ile Asn Lys Thr Arg Ile Gly Ser Phe Gly Lys Ala Arg Ile Gln Glu
            260                 265                 270

Glu Lys Gly Pro Asn Lys Ser Ser Ser Asn Gly Met Ile Cys Leu Thr
        275                 280                 285

Ser Leu Leu Arg Ile Thr Gly Val Thr Asp Lys Asp Phe Ser Leu Lys
    290                 295                 300

Tyr Asp Cys Val Ala Met Asn His His Gly Val Ile Arg His Pro Val
305                 310                 315                 320

Arg Leu Arg Arg Lys Gln Pro Ile Asp His Gln Ser Thr Tyr Tyr Ile
                325                 330                 335

Val Ala Gly Cys Ser Leu Leu Leu Met Phe Ile Asn Val Leu Val Ile
            340                 345                 350

Val Leu Lys Val Phe Trp Ile Glu Val Ala Leu Phe Trp Arg Asp Ile
        355                 360                 365

Met Ala Pro Tyr Lys Thr Gln Asn Asp Gly Lys Leu Tyr Asp Ala Tyr
    370                 375                 380

Ile Ile Tyr Pro Arg Val Phe Arg Gly Ser Ala Ala Gly Thr Gly Ser
385                 390                 395                 400

Val Glu Tyr Phe Val His Tyr Thr Leu Pro Asp Val Leu Glu Asn Lys
                405                 410                 415

Cys Gly Tyr Lys Leu Cys Ile Tyr Gly Arg Asp Leu Leu Pro Gly Gln
            420                 425                 430

Asp Ala Ala Thr Val Val Glu Ser Ser Ile Gln Asn Ser Arg Arg Gln
        435                 440                 445

Val Phe Val Leu Ala Pro His Met Met His Ser Lys Glu Phe Ala Tyr
    450                 455                 460

Glu Gln Glu Ile Ala Leu His Ser Ala Leu Ile Gln Asn Asn Ser Lys
465                 470                 475                 480

Val Ile Leu Ile Glu Met Glu Pro Met Gly Glu Ala Ser Arg Leu Gln
                485                 490                 495

Leu Gly Asp Leu Gln Asp Ser Leu Gln His Leu Val Lys Met Gln Gly
            500                 505                 510

Thr Ile Lys Trp Arg Glu Asp His Val Ala Asp Lys Gln Ser Leu Ser
        515                 520                 525

Ser Lys Phe Trp Lys His Val Arg Tyr Gln Met Pro Val Pro Lys Arg
    530                 535                 540

Pro Pro Lys Met Ala Ser Val Ala Ala Pro Leu Ser Gly Lys Val Cys
545                 550                 555                 560

Leu Asp Leu Lys His Phe
                565
```

<210> SEQ ID NO 5
<211> LENGTH: 1614
<212> TYPE: DNA
<213> ORGANISM: Rattus norvegicus
<220> FEATURE:
<221> NAME/KEY: mRNA
<222> LOCATION: (1)...(1614)
<223> OTHER INFORMATION: vacuolar ATPase

<400> SEQUENCE: 5

```
cgggccagca caagatggcg ttgcgagcga tgcggggaat cgtgaacggg gccgcgcccg      60
```

-continued

```
agctgcccgt gcccaccggt gggccgatgg ccggagctcg ggagcaggcg ctggcggtga    120

gccggaacta cctctcccag cctcgtctca cctacaagac tgtctctgga gtgaatggtc    180

cactagtgat cttagatcat gtaaagtttc ccagatatgc tgagattgtc cacttgacat    240

taccagatgg cacaaaaaga agtgggcaag ttctagaagt tagtggctcc aaagctgtgg    300

ttcaggtatt tgaaggaaca tccggcatag atgccaagaa aacatcctgt gagtttactg    360

gagatattct ccgcacacca gtgtctgagg atatgcttgg tcgagtattc aatggatcag    420

gaaaacccat tgaccgaggt cctgtggtgt tggccgaaga cttccttgac atcatgggtc    480

agccaatcaa ccctcagtgt cgcatctacc cagaagagat gattcagacg ggcatttctg    540

ccatcgacgg catgaacagt attgcgaggg gacagaaaat ccccatcttt tctgctgccg    600

ggttaccaca caacgagatt gcagctcaga tctgtcgcca ggctggtttg gtaaagaaat    660

ccaaagacgt ggtagactac agtgaagaaa actttgccat tgtgtttgct gctatgggag    720

taaacatgga aacagcccgg ttcttcaaat ctgactttga agaaaatggc tcaatggaca    780

atgtctgcct tttcttgaat ctggctaatg acccaactat cgagaggatc atcactcctc    840

gcctggctct gaccaccgct gagtttctgg cttaccagtg tgagaagcat gtcctggtca    900

tcctgacaga tatgagttct tacgctgaag cacttcgaga ggtttcagct gccagggaag    960

aggttcctgg tcggcgaggc ttccccggct acatgtatac ggatttagcc accatctatg   1020

aacgcgctgg gcgagtggaa ggtagaaatg gctctattac ccaaatccct attctcacca   1080

tgcccaatga tgatatcact catcctatcc ctgacttgac tgggtatatt actgagggcc   1140

agatctatgt ggacagacag ctgcacaaca gacagattta ccctcctatt aatgtgctgc   1200

cctcactctc tcggttaatg aagtcagcta ttggagaagg aatgaccagg aaggatcatg   1260

ctgatgtgtc taaccagttg tacgcatgct atgctatcgg taaggatgtg caagccatga   1320

aagctgtggt gggagaagaa gccctgacct cagatgacct cctttacttg gaatttctgc   1380

agaagtttga gaaaaacttc attactcagg gtccctatga aaatcgaact gtctatgaga   1440

tttggacat tggctggcag ttgcttcgaa tcttccccaa agaaatgctg aagaggatcc    1500

tcagagtac cctgagcgaa ttttaccctc gagactctgc aaagcactag ctgctgctgc    1560

tgtgcggct cgaccctctt gtgaagtgct ggttctgttt cctgattcct tttg          1614
```

```
<210> SEQ ID NO 6
<211> LENGTH: 511
<212> TYPE: PRT
<213> ORGANISM: Rattus norvegicus
<220> FEATURE:
<221> NAME/KEY: PEPTIDE
<222> LOCATION: (1)...(511)
<223> OTHER INFORMATION: vacuolar ATPase

<400> SEQUENCE: 6

Met Ala Leu Arg Ala Met Arg Gly Ile Val Asn Gly Ala Ala Pro Glu
 1               5                  10                  15

Leu Pro Val Pro Thr Gly Gly Pro Met Ala Gly Ala Arg Glu Gln Ala
            20                  25                  30

Leu Ala Val Ser Arg Asn Tyr Leu Ser Gln Pro Arg Leu Thr Tyr Lys
        35                  40                  45

Thr Val Ser Gly Val Asn Gly Pro Leu Val Ile Leu Asp His Val Lys
    50                  55                  60

Phe Pro Arg Tyr Ala Glu Ile Val His Leu Thr Leu Pro Asp Gly Thr
65                  70                  75                  80
```

-continued

```
Lys Arg Ser Gly Gln Val Leu Glu Val Ser Gly Ser Lys Ala Val Val
                85                  90                  95

Gln Val Phe Glu Gly Thr Ser Gly Ile Asp Ala Lys Lys Thr Ser Cys
            100                 105                 110

Glu Phe Thr Gly Asp Ile Leu Arg Thr Pro Val Ser Glu Asp Met Leu
        115                 120                 125

Gly Arg Val Phe Asn Gly Ser Gly Lys Pro Ile Asp Arg Gly Pro Val
    130                 135                 140

Val Leu Ala Glu Asp Phe Leu Asp Ile Met Gly Gln Pro Ile Asn Pro
145                 150                 155                 160

Gln Cys Arg Ile Tyr Pro Glu Glu Met Ile Gln Thr Gly Ile Ser Ala
                165                 170                 175

Ile Asp Gly Met Asn Ser Ile Ala Arg Gly Gln Lys Ile Pro Ile Phe
            180                 185                 190

Ser Ala Ala Gly Leu Pro His Asn Glu Ile Ala Ala Gln Ile Cys Arg
        195                 200                 205

Gln Ala Gly Leu Val Lys Lys Ser Lys Asp Val Val Asp Tyr Ser Glu
    210                 215                 220

Glu Asn Phe Ala Ile Val Phe Ala Ala Met Gly Val Asn Met Glu Thr
225                 230                 235                 240

Ala Arg Phe Phe Lys Ser Asp Phe Glu Glu Asn Gly Ser Met Asp Asn
                245                 250                 255

Val Cys Leu Phe Leu Asn Leu Ala Asn Asp Pro Thr Ile Glu Arg Ile
            260                 265                 270

Ile Thr Pro Arg Leu Ala Leu Thr Thr Ala Glu Phe Leu Ala Tyr Gln
        275                 280                 285

Cys Glu Lys His Val Leu Val Ile Leu Thr Asp Met Ser Ser Tyr Ala
    290                 295                 300

Glu Ala Leu Arg Glu Val Ser Ala Ala Arg Glu Glu Val Pro Gly Arg
305                 310                 315                 320

Arg Gly Phe Pro Gly Tyr Met Tyr Thr Asp Leu Ala Thr Ile Tyr Glu
                325                 330                 335

Arg Ala Gly Arg Val Glu Gly Arg Asn Gly Ser Ile Thr Gln Ile Pro
            340                 345                 350

Ile Leu Thr Met Pro Asn Asp Asp Ile Thr His Pro Ile Pro Asp Leu
        355                 360                 365

Thr Gly Tyr Ile Thr Glu Gly Gln Ile Tyr Val Asp Arg Gln Leu His
    370                 375                 380

Asn Arg Gln Ile Tyr Pro Pro Ile Asn Val Leu Pro Ser Leu Ser Arg
385                 390                 395                 400

Leu Met Lys Ser Ala Ile Gly Glu Gly Met Thr Arg Lys Asp His Ala
                405                 410                 415

Asp Val Ser Asn Gln Leu Tyr Ala Cys Tyr Ala Ile Gly Lys Asp Val
            420                 425                 430

Gln Ala Met Lys Ala Val Val Gly Glu Glu Ala Leu Thr Ser Asp Asp
        435                 440                 445

Leu Leu Tyr Leu Glu Phe Leu Gln Lys Phe Glu Lys Asn Phe Ile Thr
    450                 455                 460

Gln Gly Pro Tyr Glu Asn Arg Thr Val Tyr Glu Thr Leu Asp Ile Gly
465                 470                 475                 480

Trp Gln Leu Leu Arg Ile Phe Pro Lys Glu Met Leu Lys Arg Ile Pro
                485                 490                 495

Gln Ser Thr Leu Ser Glu Phe Tyr Pro Arg Asp Ser Ala Lys His
```

-continued 500 505 510

<210> SEQ ID NO 7
<211> LENGTH: 2747
<212> TYPE: DNA
<213> ORGANISM: Rattus norvegicus
<220> FEATURE:
<221> NAME/KEY: mRNA
<222> LOCATION: (1)...(2747)
<223> OTHER INFORMATION: glycoprotein CD44

<400> SEQUENCE: 7

```
ctcattgccc agcagccccc agccagtgac aggttccatt caccctcttt gccccttccc     60

ccgcgaccct tttccagagg ctactagatc ctttggtttc atcctgcaca tcatggacaa    120

ggtttggtgg cacacagctt ggggactact ttgcctctta cagttgagcc tggcacagca    180

gcagatcgat ttgaatataa cctgccgtta cgcaggtgta ttccatgtgg agaaaaatgg    240

ccgctacagt atctccagga ctgaagcagc tgacctctgc gaggctttca acaccacctt    300

gcccaccatg gctcagatgg agttagccct gagaaagggg tttgaaacat gcaggtatgg    360

gttcatagaa ggacacgtgg taatcccgag gatccacccc aacgctatct gtgcagccaa    420

caacacagga gtgtatatcc tcctcgcatc caacacctcc cactatgaca catattgctt    480

caatgcctca gctcctcttg aagaagactg tacatcagtc acagacctac ccaattcctt    540

cgatggacca gttaccataa ctattgtcaa ccgtgatggc acccgctaca gcaagaaggg    600

cgagtataga acacaccaag aagacatcga tgcctcaaac attatagatg aggatgtcag    660

cagtggatcc accattgaga agagcacccc agaaggctac attttgcaca ccgaccttcc    720

cacttcacag cctactggag accgggatga cgccttcttt attgggagca ccctggccac    780

cagtgatgga gactcatcca tggaccccag gggtggtttc gacactgtga ctcatggatc    840

cgaattagct ggacactcaa gtgggaatca agacagtgga gtgaccacaa cttctggtcc    900

tgcgaggaga cctcagattc cagagtggct tatcatcttg gcatccctcc tggcgctggc    960

tctgattctt gccgtctgca ttgctgtcaa cagtaggaga aggtgtgggc agaagaagaa   1020

gctggtgatc aacagtggca atggaacagt ggaagacagg aaaccaagtg aactcaacgg   1080

ggaggccagc aagtctcagg aaatggtgca tttggtgaac aaggaaccaa cagagactcc   1140

ggaccagttt atgacagctg atgagacccg gaatctgcag agtgtggata tgaagattgg   1200

ggtgtagtgc ctatgccact aacttgaaaa gacacaacaa ttggagacat gtcattactg   1260

ggagctggga cccttaacag atgcaatgtg ctactgatta tttttattg ggattatttt   1320

gggcataaaa tttccctttt tttgtttttt aaaagtttgt tttccaattt atgaaaatag   1380

cattgctttc tgaaatgagg gtctcttcca gttcctcctt agaggccttg cattaccagg   1440

gtatgctacc ataggcttct accaaatgaa tactcttggt cccgattgaa cccaaagtcc   1500

caggtaacat ccaccagcta aggatttccc cagaacttag agagattggt ctctgggagg   1560

aaatttgaat gggtccatat tgcctcccag cagtccaatc tgtaggcatt gctttgcagt   1620

ggatgggaga tcaggtgtac tggttacaca ctctctttat agactccctt ctgctggaaa   1680

atttccacat gcttctgaga gattccccaa aggtgacgct atttatcttt agtaagctat   1740

ttatctttgt ttttgaaata tcaaaccctg gaggtccttt tttcagtatg actttttttta   1800

ttttgttttt ttttatttttg ttttttaggt tactttgtca gaagcataac agggtataag   1860

ttgattcata ataaatacct gtccatcttc catcttgacc tgttgtgctg tgatccttca   1920

gtttctaaat cagcaaggtc tgagtctttg tagcacatca atgtgacctt agtatggtcc   1980
```

-continued

```
tctgaaactc atgttagagc atccgtgccc tgcttgggtt tacccagctg aatctcagaa   2040

gatcaaggac aggagcactg ttttcattct aggactatca aaggggtttc tctcctgttc   2100

aagaatctga attgggagta ggagagcttc tgtccctttt atgtttcgat aaccacccat   2160

ttctctttct taaagggcac attaagtttt tatatcttac aacattcgcg gtcctgtttc   2220

atagacactg atcttattgg cactttcaca aaacagtgtg gaggggactt ctgacacctt   2280

atagtaaaag gagaagccaa cagaaatgaa agtgtggaca gagagcagta gattggcatg   2340

aggaggcatg atgtacaacc cccagaccac tctttccatc accacatttg ttgatgcttt   2400

cgcaagccag ttggtactta gaatcagttc cccagggaat ccttcaaaaa gccataagaa   2460

tgcccacccc tggaatctta ccaccaccag atgagcaggt ttatggttta gcaaaaggag   2520

aatgctgtca ccctctgacc tcatagtttt cacatactgg gcaagtgttc atctgccagg   2580

atgccccatt gctcctaggt cttcccaggt accttgtaga agaacttaaa tctataaaat   2640

aaggctttct ctaaaatgga acttcctttc taaggctccc atttttactg ttgactaaat   2700

ttatatgttt aatagttttt tttcaaataa aaacaaacac aaaaagg                 2747
```

```
<210> SEQ ID NO 8
<211> LENGTH: 364
<212> TYPE: PRT
<213> ORGANISM: Rattus norvegicus
<220> FEATURE:
<221> NAME/KEY: PEPTIDE
<222> LOCATION: (1)...(364)
<223> OTHER INFORMATION: glycoprotein CD44

<400> SEQUENCE: 8

Met Asp Lys Val Trp Trp His Thr Ala Trp Gly Leu Leu Cys Leu Leu
 1               5                  10                  15

Gln Leu Ser Leu Ala Gln Gln Gln Ile Asp Leu Asn Ile Thr Cys Arg
            20                  25                  30

Tyr Ala Gly Val Phe His Val Glu Lys Asn Gly Arg Tyr Ser Ile Ser
        35                  40                  45

Arg Thr Glu Ala Ala Asp Leu Cys Glu Ala Phe Asn Thr Thr Leu Pro
    50                  55                  60

Thr Met Ala Gln Met Glu Leu Ala Leu Arg Lys Gly Phe Glu Thr Cys
65                  70                  75                  80

Arg Tyr Gly Phe Ile Glu Gly His Val Val Ile Pro Arg Ile His Pro
                85                  90                  95

Asn Ala Ile Cys Ala Ala Asn Asn Thr Gly Val Tyr Ile Leu Leu Ala
            100                 105                 110

Ser Asn Thr Ser His Tyr Asp Thr Tyr Cys Phe Asn Ala Ser Ala Pro
        115                 120                 125

Leu Glu Glu Asp Cys Thr Ser Val Thr Asp Leu Pro Asn Ser Phe Asp
    130                 135                 140

Gly Pro Val Thr Ile Thr Ile Val Asn Arg Asp Gly Thr Arg Tyr Ser
145                 150                 155                 160

Lys Lys Gly Glu Tyr Arg Thr His Gln Glu Asp Ile Asp Ala Ser Asn
                165                 170                 175

Ile Ile Asp Glu Asp Val Ser Ser Gly Ser Thr Ile Glu Lys Ser Thr
            180                 185                 190

Pro Glu Gly Tyr Ile Leu His Thr Asp Leu Pro Thr Ser Gln Pro Thr
        195                 200                 205

Gly Asp Arg Asp Asp Ala Phe Phe Ile Gly Ser Thr Leu Ala Thr Ser
```

-continued

```
    210                 215                 220

Asp Gly Asp Ser Ser Met Asp Pro Arg Gly Gly Phe Asp Thr Val Thr
225                 230                 235                 240

His Gly Ser Glu Leu Ala Gly His Ser Ser Gly Asn Gln Asp Ser Gly
                245                 250                 255

Val Thr Thr Thr Ser Gly Pro Ala Arg Arg Pro Gln Ile Pro Glu Trp
            260                 265                 270

Leu Ile Ile Leu Ala Ser Leu Leu Ala Leu Ala Leu Ile Leu Ala Val
        275                 280                 285

Cys Ile Ala Val Asn Ser Arg Arg Arg Cys Gly Gln Lys Lys Lys Leu
    290                 295                 300

Val Ile Asn Ser Gly Asn Gly Thr Val Glu Asp Arg Lys Pro Ser Glu
305                 310                 315                 320

Leu Asn Gly Glu Ala Ser Lys Ser Gln Glu Met Val His Leu Val Asn
                325                 330                 335

Lys Glu Pro Thr Glu Thr Pro Asp Gln Phe Met Thr Ala Asp Glu Thr
            340                 345                 350

Arg Asn Leu Gln Ser Val Asp Met Lys Ile Gly Val
        355                 360


<210> SEQ ID NO 9
<211> LENGTH: 5028
<212> TYPE: DNA
<213> ORGANISM: Rattus norvegicus
<220> FEATURE:
<221> NAME/KEY: mRNA
<222> LOCATION: (1)...(5028)
<223> OTHER INFORMATION: Lot-1

<400> SEQUENCE: 9

gcctggcagg cgggagaacg ctccggagtt gtggccgtgg gcaccgggct cgcggcaaga     60

ggagcggaga gcgggcatct cctgagcgcc gtcatggctg cttaggctgc gcctgccagc    120

ggaccgacgg tgtcgcccga atccggctcg gataggtctg gttggagtct gtgcctgctt    180

gcttggcgtg tggttgttcc tgcttgattg gcacggtgcc attggcttcg tatttgggaa    240

tcggaggagt taatcttgtc tcttctcaca ggttcgagtc ctcagacctt ctgcaggact    300

ccatccatat ctgcctcgca gctgactctc ctgctcacac agaagacggc catcctagat    360

ccccagctat tgtgctgacc atccccttcc tgctccggat ctcgcctggc tgctaggctg    420

tggtgctgcc ttttcagagt caggctgtag cgactccccg ccttcgtccc ggctgggctt    480

aggtggaaca gtggttcatc tcatctcatc agcacttctg aagaagaaag tgtgagaagc    540

agaggccatg gctccttttc gctgtcaaaa atgcggcaag tccttcctca ccctggagaa    600

gttcaccatc cacaattatt cccacaccag ggagcgccca ttcaagtgct ccaagactga    660

gtgtggcaaa gccttcgtct ccaagtataa gctgatgaga cacatggcta cgcactctcc    720

ccagaagacg caccagtgca ctcattgtga aaagactttc aaccggaagg atcatctgaa    780

gaatcacctc cagacccacg atcccaacaa gatgatctac gcctgcgaag attgtggcaa    840

gaaataccac accatgctgg gctacaagag gcacatggcc ctgcattcgg ccagcagcgg    900

cgatctcacc tgcggcgtct gcaccctgga gctggggagc accgaggtcc tgctggacca    960

cctcaagtct cacgcggaag aaaaggccca ccacgcgccc agggagaaga aacaccagtg   1020

cgaccactgc gagagatgct tctacacccg gaaggatgtg cgtcgccacc tggtggtcca   1080

cacaggatgc aaggacttcc tgtgtcagtt ctgcgcccag agatttgggc gcaaagacca   1140
```

-continued

```
cctcactcgt cacaccaaga agacccactc ccaggagctg atgcaagaga gcctgcaagc   1200
aggagaatac cagggcggtt accaacccat tgcgcctccg ttccagatca aggctgatcc   1260
catgcctcct ttccagttag aaatgccccc cgagagcggg cttgatgggg gcttgcctcc   1320
tgagattcat ggtctagtgc ttgcttcccc agaggaggtt ccccagccta tgctgtctat   1380
gccgccaatg cagccaatgc cagagcagcc tttcactctg caccctgggg tagttccctc   1440
ctctcctccc ccgatcattc ttcaggagca taagtacagc ccagttccta cctcttttgc   1500
cccgttcgta agcatgccga tgaaagcaga tctcaagggc ttttgcaaca tgggtctctt   1560
tgaggaattt cctctgcaag agtgtcagtc gcctgtcaag ttcagtcagt gctttgagat   1620
ggctaaggaa gggtttggga aagtcaccct gcccaaagag ctgctggtag atgctgtaaa   1680
tatagccatt cctggctctc tggagatttc ctctctcttg ggttctggc agctgccccc   1740
tcctcctccc cagaatggct tcatgaatgg caccatccct gtgggggccg gggagccgct   1800
gccccatagg ataacttgtc tggcacagca gcagccacca cctctgctac ctccgccgcc   1860
gccgctgccg ctgccagagc cgctgccaca gccacagctg ccgccacagt ttcagttgca   1920
gctccagccc cagccccaga tgcagcccca gatgcagctg cagcctctac agctgcagct   1980
gccccagctg ctgccccagc tgcagcccga gcctgagcca gagccagagc cagaggaaga   2040
agaggaagaa gaagaagaga tagaagaaga agaagagatc gaagaagaag aagaagccga   2100
accagaagca gaagaagaag aggaggcaga agacgaagag gaggcagagg aagaggaaga   2160
agagccacag ccagaagaag cccaaatagc aatgagcgct gtgaatatgg gccagccccc   2220
gctacccccg accccctcatg ttttcacagc tggcaccaac actgctatcc tgccccattt   2280
ccaccacgcg ttcagataaa ttggtttttt aagagggtgc ttctcttctg gaagatgttt   2340
caaacaccag ttccagttcc agacatcagt tacagtttga agagaagcgt tggaaaaaca   2400
ggaatggggt ttctagctta ttgccatgag tagattgaga aaaagaactc tcttaactgc   2460
atgcactgtg ccaatacata tatatatata tatatatata tatatatgta tatatatata   2520
tatatatatc atccttagta ttcatgcttt gtaccaaact tagtgagtgc gggcgttctc   2580
cgtaatcgaa ctgcaagtag tatcatatta ttaccctgat attgttagtc tcatattatt   2640
agccttgtat tattctcata taatcaaaac caagatccaa aacatgagct gctaatttgt   2700
aaatatcgtg ttgagtgtta gccgtcgtag tgatgttagc tgcgtagttg cgtgttagca   2760
ctgcctagga agggcacgag ggccaagttg ggcttctccc acttggaaga tgttttgaag   2820
agaaggggtg gatctccgta gggcgtccgt aactaggccg tgtgttcttt tcagggaccc   2880
gtctaccttc aggattggat gtagtttagt cgctcttctt cttagctcgc tttgtagttt   2940
gtccttctgg tagcctactg tgtgtgtctg tgtgtagctt tataggaaag ttccgtgtga   3000
agctgtcggt gtcttcgttt tcaaaagtga attttaaatg tatttttcaa tatttttcat   3060
gtgatgttgt accaatgtga attatgactt cgtttatctt aaagacaaaa ctggttgtca   3120
gtcatatctg acaggaagaa agaaatccct gtgggtaggc aagtcaagtg gccaactaat   3180
gagaagaagc atcaatcgaa agtgttggct gactgggaca ctcatgattc tcacaggact   3240
ttgagaaacg tactggaatt aaaaaaaaaa aagcttaagt acattagata agaattttct   3300
ttgcctagct taacctacta cttaagcctc ttaagttctg aagtattgtg atcaaccaat   3360
aggaaaatgt atctgtagtt gatgaatttc agtccttgtt actttgtatc ccaagaggtt   3420
tgtgttttgg gaatgtaacc gtacttgtaa tctcagttgg tatcttgcta atcgatttga   3480
aagtgtaaaa cctaaccctt gaagactctg tatttccttt tttgagactg tatttcccag   3540
```

-continued

```
catgtatacc ctaacctttg gagactctgt attctgtttt tgagactttc cccccgcccc   3600
ccagcatatg taccccgacc cttgaagact gtatttcgtt tttgagagcg tatttcccag   3660
catatataca ctaacccttg aagactctgt atttcctttt ttgagactgt atttcccagc   3720
atatatacac taacccttga agactctgta tttcctttt tgagactgta tttcccagca   3780
tatatacact aacctttgaa gactctgtat tctgttttg agaccccccc ccagcatatg   3840
taccctaacc cttgaagact gtatttcgtt tttgagaacg tatttcccag catatataca   3900
ctaacctttg gaagactctg tatttcattt ttgagactgt gtttcttagt atacataccc   3960
taacctttga aagactccat ttttgagact tccccccccc cagcatttgt gccctaaccc   4020
ttggaggctt tgtatttttt ttttgagact tttccgccag catatataca ctaacccttg   4080
aagactctgt atttcatttt tgagactttt ttccccagca tatataccgt aacccttgaa   4140
gactctgtat tccgttttg agattttttt ccctcagcat atataccca acctttgaag   4200
actctgtatt tcatttttga gacttttcc cagcatatat accctaacct ttgaagactc   4260
tgtattccat ttttgagatt ttttccctca gcatatatac cctaaccttt gaagactctg   4320
tatttcgttt ttgagatttt ttcccccagc atataaacac taacctttga agactctgta   4380
tttcattttt gagacttttt tcccagcata tataccctaa cccttgaaga ctctgtaatc   4440
tgtttttttt tttttttgag actttttccc ccagcatata tacactaacc tttgaagact   4500
ctgtattcca ttttttgaga cttttttccc cagcatatat accctaacct ttgaagactc   4560
tgtatttcat ttttgagact ttttccccag catatatacc ctaacctttg aagactctgt   4620
attccgtttt tgagaccccc cccccggcat gaataccta atctttgaag actctggtat   4680
ttcatttttg agattttttt cccctcagca tatatacact aacctttgta gactctgtat   4740
tccgtttttg agactttccc cccccagcat gtataccta acctttgaag actctgtatt   4800
tccagcattt gtaccctacc cttgaagact ctgtatttcc cagcatttgt accctaaccc   4860
ttgaagaccc tgtatttcgt ttgtaagact tttccccagc atatatatcc tacatataat   4920
aaacgctaag catctagcaa aaaaaaaaaa aaaaaaaaaa aaaaaaaaaa aaaaaaaaaa   4980
aaaaaaaaaa aaaaaaaaaa aaaaaaaaaa aaaaaaaaaa aaaaaaaa
```

<210> SEQ ID NO 10
<211> LENGTH: 583
<212> TYPE: PRT
<213> ORGANISM: Rattus norvegicus
<220> FEATURE:
<221> NAME/KEY: PEPTIDE
<222> LOCATION: (1)...(583)
<223> OTHER INFORMATION: Lot-1

<400> SEQUENCE: 10

```
Met Ala Pro Phe Arg Cys Gln Lys Cys Gly Lys Ser Phe Leu Thr Leu
 1               5                  10                  15

Glu Lys Phe Thr Ile His Asn Tyr Ser His Thr Arg Glu Arg Pro Phe
            20                  25                  30

Lys Cys Ser Lys Thr Glu Cys Gly Lys Ala Phe Val Ser Lys Tyr Lys
        35                  40                  45

Leu Met Arg His Met Ala Thr His Ser Pro Gln Lys Thr His Gln Cys
    50                  55                  60

Thr His Cys Glu Lys Thr Phe Asn Arg Lys Asp His Leu Lys Asn His
65                  70                  75                  80

Leu Gln Thr His Asp Pro Asn Lys Met Ile Tyr Ala Cys Glu Asp Cys
```

-continued

```
                85                  90                  95

Gly Lys Lys Tyr His Thr Met Leu Gly Tyr Lys Arg His Met Ala Leu
            100                 105                 110

His Ser Ala Ser Ser Gly Asp Leu Thr Cys Gly Val Cys Thr Leu Glu
        115                 120                 125

Leu Gly Ser Thr Glu Val Leu Leu Asp His Leu Lys Ser His Ala Glu
    130                 135                 140

Glu Lys Ala His His Ala Pro Arg Glu Lys Lys His Gln Cys Asp His
145                 150                 155                 160

Cys Glu Arg Cys Phe Tyr Thr Arg Lys Asp Val Arg Arg His Leu Val
                165                 170                 175

Val His Thr Gly Cys Lys Asp Phe Leu Cys Gln Phe Cys Ala Gln Arg
            180                 185                 190

Phe Gly Arg Lys Asp His Leu Thr Arg His Thr Lys Lys Thr His Ser
        195                 200                 205

Gln Glu Leu Met Gln Glu Ser Leu Gln Ala Gly Glu Tyr Gln Gly Gly
    210                 215                 220

Tyr Gln Pro Ile Ala Pro Pro Phe Gln Ile Lys Ala Asp Pro Met Pro
225                 230                 235                 240

Pro Phe Gln Leu Glu Met Pro Pro Glu Ser Gly Leu Asp Gly Gly Leu
                245                 250                 255

Pro Pro Glu Ile His Gly Leu Val Leu Ala Ser Pro Glu Glu Val Pro
            260                 265                 270

Gln Pro Met Leu Ser Met Pro Pro Met Gln Pro Met Pro Glu Gln Pro
        275                 280                 285

Phe Thr Leu His Pro Gly Val Val Pro Ser Ser Pro Pro Pro Ile Ile
    290                 295                 300

Leu Gln Glu His Lys Tyr Ser Pro Val Pro Thr Ser Phe Ala Pro Phe
305                 310                 315                 320

Val Ser Met Pro Met Lys Ala Asp Leu Lys Gly Phe Cys Asn Met Gly
                325                 330                 335

Leu Phe Glu Glu Phe Pro Leu Gln Glu Cys Gln Ser Pro Val Lys Phe
            340                 345                 350

Ser Gln Cys Phe Glu Met Ala Lys Glu Gly Phe Gly Lys Val Thr Leu
        355                 360                 365

Pro Lys Glu Leu Leu Val Asp Ala Val Asn Ile Ala Ile Pro Gly Ser
    370                 375                 380

Leu Glu Ile Ser Ser Leu Leu Gly Phe Trp Gln Leu Pro Pro Pro Pro
385                 390                 395                 400

Pro Gln Asn Gly Phe Met Asn Gly Thr Ile Pro Val Gly Ala Gly Glu
                405                 410                 415

Pro Leu Pro His Arg Ile Thr Cys Leu Ala Gln Gln Gln Pro Pro Pro
            420                 425                 430

Leu Leu Pro Pro Pro Pro Pro Leu Pro Leu Pro Glu Pro Leu Pro Gln
        435                 440                 445

Pro Gln Leu Pro Pro Gln Phe Gln Leu Gln Leu Gln Pro Gln Pro Gln
    450                 455                 460

Met Gln Pro Gln Met Gln Leu Gln Pro Leu Gln Leu Gln Leu Pro Gln
465                 470                 475                 480

Leu Leu Pro Gln Leu Gln Pro Glu Pro Glu Pro Glu Pro Glu Pro Glu
                485                 490                 495

Glu Glu Glu Glu Glu Glu Glu Glu Ile Glu Glu Glu Glu Glu Ile Glu
            500                 505                 510
```

```
Glu Glu Glu Glu Ala Glu Pro Glu Ala Glu Glu Glu Glu Glu Ala Glu
        515                 520                 525

Asp Glu Glu Glu Ala Glu Glu Glu Glu Glu Glu Pro Gln Pro Glu Glu
    530                 535                 540

Ala Gln Ile Ala Met Ser Ala Val Asn Met Gly Gln Pro Pro Leu Pro
545                 550                 555                 560

Pro Thr Pro His Val Phe Thr Ala Gly Thr Asn Thr Ala Ile Leu Pro
                565                 570                 575

His Phe His His Ala Phe Arg
            580


<210> SEQ ID NO 11
<211> LENGTH: 658
<212> TYPE: DNA
<213> ORGANISM: Rattus norvegicus
<220> FEATURE:
<221> NAME/KEY: mRNA
<222> LOCATION: (1)...(658)
<223> OTHER INFORMATION: AA892598 (EST196401)

<400> SEQUENCE: 11

acaaacactt tttattttgt ttttaattta gaacatgata catattcaca agatttacac     60

tttatatcat accaaagcaa tctagaaaca ctgtacagag cacacttgaa catttagaag    120

gctatatata atctgtggta aagtcatagg catcgtcttc ttcactcatt ttatccaaga    180

taaaggatct gtcagatggt ttacttgctg ttgattgccc aggtgacatc tccctggtct    240

cttctacagg agtcacatct gagatctctg cattttttc accagtaaca tgttcttgat     300

catcaccatc ctgttggtct tctgtctgtt ttggtgactc ttcggggatg tccttttctt    360

ctagtattcc atttgtcagg cccgaagacc ggaaaaggat tttattagtt aaatgagggc    420

ccttgaggac ttgtatgctg tgtgcattat tcttttctag ttcttctaga ttaaagcccc    480

cttcatgat tgctgtaata ttctcattaa aatgaggaga atgattccag gatgcagggg     540

atggcagta gtaacctaat gaggcacctg tccactcaga ccatagcagc ttagcagcac     600

ttcgacatt tgggcttcca cctttttggt gcagacctct tctctgagca agtttagt       658


<210> SEQ ID NO 12
<211> LENGTH: 480
<212> TYPE: DNA
<213> ORGANISM: Rattus norvegicus
<220> FEATURE:
<221> NAME/KEY: mRNA
<222> LOCATION: (1)...(480)
<223> OTHER INFORMATION: AA900476 (Mrg-1)

<400> SEQUENCE: 12

ttttttttt tttttttgtt tgtttttgat tttttttaat tcacaccgaa gaagttgggg      60

gtgggggcag ggagggtgat ttctttcagc cgcgaggtta accgagtcaa cagctgactc    120

tgctgggctg ctgtttgcac acgaagtccg tcataaaatc aaactcattt tggcccagcc    180

agagttctgg cagctccttg atgcggtcca aacccatctc tatcactaag gacataagca    240

cttcctcgtc gatgaaatca gtgtctatga cattgggcgg cagcattgcc gcggggacgt    300

gagccaccga ggcgggcatg gtgctgccac cgccactgcc gcccgcgctg ctgccacccg    360

cgccgcccga ggtgccgccg gagccgccgg gggtgccgct gccacccgcg ccgccagggg    420

tgctgctgcc tccactgtgc ttggggttgc aatctcggaa gtgctggttt gtcccgttca    480
```

-continued

<210> SEQ ID NO 13
<211> LENGTH: 2646
<212> TYPE: DNA
<213> ORGANISM: Mus musculus
<220> FEATURE:
<221> NAME/KEY: mRNA
<222> LOCATION: (1)...(2646)
<223> OTHER INFORMATION: ST2

<400> SEQUENCE: 13

```
gcagaaatga gacgaaggag cgccaagtag cctcacggct ctgagcttat tctctccagc     60
ccttcatctg ggtatctaca gtgatttctc ttctggaccc tacctcagag agcacttgtc    120
aaccgcctag tgaacacacc attactatcc tgtgccattg ccatagagag acctcagcca    180
tcaatcacta gcacatgatt gacagacaga gaatgggact ttgggctttg gcaattctga    240
cacttcccat gtatttgaca gttacggagg gcagtaaatc gtcctggggt ctggaaaatg    300
aggctttaat tgtgagatgc ccccaaagag gacgctcgac ttatcctgtg gaatggtatt    360
actcagatac aaatgaaagt attcctactc aaaaaagaaa tcggatcttt gtctcaagag    420
atcgtctgaa gtttctacca gccagagtgg aagactctgg gatttatgct tgtgttatca    480
gaagccccaa cttgaataag actggatact tgaatgtcac catacataaa aagccgccaa    540
gctgcaatat ccctgattat ttgatgtact cgacagtacg tggatcagat aaaaatttca    600
agataacgtg tccaacaatt gacctgtata attggacagc acctgttcag tggtttaaga    660
actgcaaagc tctccaagag ccaaggttca gggcacacag gtcctacttg ttcattgaca    720
acgtgactca tgatgatgaa ggtgactaca cttgtcaatt cacacacgcg gagaatggaa    780
ccaactacat cgtgacggcc accagatcat tcacagttga agaaaaaggc ttttctatgt    840
ttccagtaat tacaaatcct ccatacaacc acacaatgga agtggaaata ggaaaaccag    900
caagtattgc ctgttcagct tgctttggca aaggctctca cttcttggct gatgtcctgt    960
ggcagattaa caaaacagta gttggaaatt ttggtgaagc aagaattcaa gaagaggaag   1020
gtcgaaatga aagttccagc aatgacatgg attgtttaac ctcagtgtta aggataactg   1080
gtgtgacaga aaaggacctg tccctggaat atgactgtct ggccctgaac cttcatggca   1140
tgataaggca caccataagg ctgagaagga aacaaccaag taaggagtgt ccctcacaca   1200
ttgcttgaat aaattggctg aatcagctgt gcactgcatc cgttttctcc gaggactgtg   1260
tgttgtagct tggtcccagg gaatccatca tgatcaaggg aatagttggc ctgtttcatc   1320
aagtgttctt ctcacgttga ggaagctcct taaatctggt ctttccagaa tgtttctgtc   1380
ttccaacagg aatctctgtc attgtatcct tcccctctct gtgtcccctc ctccttgttc   1440
tcccggcagt cctccccatc tcctcacctc ccttaatgtg ttcttgaccc ccttctctct   1500
tttccttctc tctgagctcc ttctcaccca atagtggctt ttgcagtcat cctttgtacc   1560
gactacaagg gacattggta ttggtagtgg gttcagagca gtaataactc tgctgtgtct   1620
ctttgtataa ccttgtcatg gaaaacaact tacaaacttt cattctgagc agttattaat   1680
tcccttgctt ggtccttggg ttgacaggtg cagccatcat gatagataga tgaccaacct   1740
gatccgattt taaaagagta aacatctttt ttacccttat cactctctta tgatactgac   1800
cactgcctta ctggcaatac aactaatatg aaaacatttt taatttcttt caaatatcaa   1860
gagggcatgg gagggagaga gacactaact ctaagatcat agcaatatgt ggggcattta   1920
tttggatgaa tatattgatt aaaagggtag ggtggaggta cctattagat tcagtcatgc   1980
tgtgtctctg cctgaagtgg tatttgggat ttttgttgat tctgtttgtc ttcttttgtt   2040
```

-continued

```
tgtttttact atagaaacta ttctgccctt gtactcctag agtcacctgt ctttgcctcc   2100

agttactggg actaaagcta tgtgtcacct tactgagcca gggtgtttct tgttttggtt   2160

ttgattttag agcctctggc ttgtaacatt tttataaaac agaattttga ttcctaggtg   2220

gccagagttg tgactcatag agggattttt gtgctgttgt gatcagtgag gtcttgggga   2280

tctgcccctg ataatggtgt tactccgggt gactgtggac cacagcactg tgttcccaga   2340

tggtggtggt cactgcacat tctgcaggaa aagagaatcc aaacccctat tctcacccag   2400

tttgaccttg attccacaat gccttcctct gtaacaggat cttttgtcta gatttctgag   2460

tgtactttag ttcacgtttg tattagaatt atatttttta atcagtaatt ttgtatttgt   2520

tttgtttgtg tgtgatttct ttgttttcca gtttattttt aattcacttg ttgctattca   2580

aatcaatgtg ttcatactgt ttgaacaaca cagcgtatta aataaaattc gtgtctattg   2640

ttcttg                                                               2646
```

<210> SEQ ID NO 14
<211> LENGTH: 4989
<212> TYPE: DNA
<213> ORGANISM: Mus musculus
<220> FEATURE:
<221> NAME/KEY: mRNA
<222> LOCATION: (1)...(4989)
<223> OTHER INFORMATION: ST2L

<400> SEQUENCE: 14

```
tgccattgcc atagagagac ctcagccatc aatcactagc acatgattga cagacagaga     60

atgggacttt gggctttggc aattctgaca cttcccatgt atttgacagt tacggagggc    120

agtaaatcgt cctggggtct ggaaaatgag gctttaattg tgagatgccc ccaaagagga    180

cgctcgactt atcctgtgga atggtattac tcagatacaa atgaaagtat tcctactcaa    240

aaaagaaatc ggatctttgt ctcaagagat cgtctgaagt ttctaccagc cagagtggaa    300

gactctggga tttatgcttg tgttatcaga agccccaact tgaataagac tggatacttg    360

aatgtcacca tacataaaaa gccgccaagc tgcaatatcc ctgattattt gatgtactcg    420

acagtacgtg gatcagataa aaatttcaag ataacgtgtc caacaattga cctgtataat    480

tggacagcac ctgttcagtg gtttaagaac tgcaaagctc tccaagagcc aaggttcagg    540

gcacacaggt cctacttgtt cattgacaac gtgactcatg atgatgaagg tgactacact    600

tgtcaattca cacacgcgga gaatggaacc aactacatcg tgacggccac cagatcattc    660

acagttgaag aaaaaggctt ttctatgttt ccagtaatta caaatcctcc atacaaccac    720

acaatggaag tggaaatagg aaaaccagca agtattgcct gttcagcttg ctttggcaaa    780

ggctctcact tcttggctga tgtcctgtgg cagattaaca aaacagtagt tggaaatttt    840

ggtgaagcaa gaattcaaga agaggaaggt cgaaatgaaa gttccagcaa tgacatggat    900

tgtttaacct cagtgttaag gataactggt gtgacagaaa aggacctgtc cctggaatat    960

gactgtctgg ccctgaacct tcatggcatg ataaggcaca ccataaggct gagaaggaaa   1020

caaccaattg atcaccgaag catctactac atagttgctg gatgtagttt attgctaatg   1080

tttatcaatg tcttggtgat agtcttaaaa gtgttctgga ttgaggttgc tctgttctgg   1140

agagatatag tgacacctta caaaacccgg aacgatggca agctctacga tgcgtacatc   1200

atttaccctc gggtcttccg gggcagcgcg gcgggaaccc actctgtgga gtactttgtt   1260

caccacactc tgcccgacgt tcttgaaaat aaatgtggct acaaattgtg catttatggg   1320

agagacctgt tacctgggca agatgcagcc accgtggtgg aaagcagtat ccagaatagc   1380
```

-continued

```
agaagacagg tgtttgttct ggcccctcac atgatgcaca gcaaggaatt tgcctacgag 1440
caggagattg ctctgcacag cgccctcatc cagaacaact ccaaggtgat tcttattgaa 1500
atggagcctc tgggtgaggc aagccgacta caggttgggg acctgcaaga ttctctccag 1560
catcttgtga aaattcaggg gaccatcaag tggagggaag atcatgtggc cgacaagcag 1620
tctctaagtt ccaaattctg gaagcatgtg aggtaccaaa tgccagtgcc agaaagagcc 1680
tccaagacgg catctgttgc ggctccgttg agtggcaagg catgcttaga cctgaaacac 1740
ttttgagttg agagctgcgg agtcccagca gtaggcaccg gagtgcaggt gtgcagactt 1800
gaaatgccaa gggtgggggc cccaagtctc agctaaagag caactctagt ttattttcct 1860
ggttatggta ggagccaccc atcgtttgtt tccggtttcc ttttcctact tcactcttgt 1920
ggcacaagat caaccctgag ctttttcctt ttcttttatt tctctttttg ttccttcttt 1980
taaaagcttt ttaaaattga ttatcttatt tatctacctt tcaaaggtta tccccccttcc 2040
cggtgccccc tctacaaatc cccatcctgc ttccctcctc cctgcttcta tgagggtgcc 2100
cccccacctg cccatccact ccagccttac aggccttgtg ttcccctatg ctggggcatc 2160
gagcctccat aagacctccc ctctcattca tcaattatct acattctgaa tatcaagccg 2220
acacttttgt ttttgttttt gatttttga gacagggttt ctctgtgtag ccctggctgt 2280
cttgaaactc acattgtaga ccaggctggc ctcgaactca gaaatcagcc tgcctctgcc 2340
tccccgagtg ctgggattaa aggcgtgcgc caccacgccg ggctaagcct acactttcag 2400
aataaagttc tgattcacct caaagagcag tctcattccc agaggcagag agccggaaag 2460
agcctccaat gtgcttgtcc aggcagagct gaccttattt gcttaccagt cacaggtaaa 2520
caaagcgttt ctccgtgttg cctcttgtag acatccctgt aatagattag gaagggaatg 2580
agccgtccta ctgaccagtt tgtgaattgt ggtagaaaaa gcgttgacgt ttgttaaata 2640
cttgttagca atgtaaacct cattcctaac acaccagaat ttcttacttt ttattcgtca 2700
attaccgagt tttgtcaagt cagtattaac agatttggtc gaataccttta cccaaattgc 2760
cattacagtc gagcatgttt tcagttctaa atgcctttta tatatttttt attcttctta 2820
gaaatacttc ctcactttaa aagtaatgta aagatgtgtt agaaaacata aggtgtaaga 2880
gaaagtatga taaaatataa aaaataatag aaaggaaagg aaatataatg aaaatcataa 2940
ctcttaagat taattttggt aggtctgtat tttaaaatat aattaaattt tataccgata 3000
acttttatag ctgagattgt acactacaga ctaggcagct tttcctattt accaccataa 3060
tgaaaactgg tggctgattt ctttaacatt cacagaagtt ccaaatgtct cattttagac 3120
tgtgctgcag actatggctg aagcagccag aatgagaaac aggtctgcca tgtcacatcg 3180
ggacattttc ctacttactg aaatgtatct gtcactgtgc gacagctaac ttttgtgata 3240
ctcctatgaa atgtgtaggg aatttggaca gaacagaatc aatctatagt cagaggtcct 3300
ctggacagtc ttttccagga gcacacacag accgtgaggt cctaggcacc caggaaacgg 3360
atccagagcc caggcaagtg tcttacaggt accttgaatt ttgccaatag atatgagccc 3420
tgccttagct gagttgctca gtcggtgatg ggactccagg ctgaggtgac aatgaacaca 3480
gaatttggga gactcttgaa aggaggggaa tgttgaactc acggtcaaca tatgaggctg 3540
cagagaagcc gtatgcagaa gtgtgtgtag aggatctaga gtagcccgtt tctctgggga 3600
cagtgtgctc ttagtctgta cccttaggct gggttgccag gtaaacattt gctagtgttc 3660
agttcaaagg ctgaagcttg agctgagggt gatgaggaat tcaaacttcc cctcgcatgc 3720
```

```
atccaccctg tggttgcctg gtttgctaag tccacctgct ctgctgtagt agaaggtttt   3780

gatcttctgc agcttcatct acttcttagt gagttgccaa aactgaccac tgaaaagcat   3840

gctgtgtaca taactgtctc atgtcccaga acgtgcaatc aggaggaagt cctcactccc   3900

gataacggaa tccttgctct gtggctgtga ggacgtccct tagcaacctc agatagtaat   3960

ttttcttagg ttggatggaa catagtaacg tgctggattc tttgctaact gaaaatagaa   4020

gtattcggat ttcagaaaga actggataaa tattaatgtt ggtgattatg aaatctcatt   4080

gtgagccgtg tgagtttgag tgtgtattcc atgattgtgc tgaatgaaga cctctaaaaa   4140

tgaaattctc tccaatctca tccctgggaa tagttgcttc ctcatgcctg ctgctccatc   4200

catggaaaat gactaaagag aattattatt tgttcccgag attcttctga taagtctaaa   4260

ctatttgcat gtaattgagc tgggcagcat ggcacacttg ggaggcagag gcaggtggat   4320

ctctgtgagt ttgaggccag cctgctctac agagttagtt ccaggacacc agagctacaa   4380

aaagaaaacc tgtcctaaca acaacagcaa cagctgcagc agcaacaaca acaacaaaga   4440

aaaagaagag gaggaggagg aaaggaaaga aggaagaagg aagaagaaag ggaagaaata   4500

atagattttt ctgtaatgaa cacacatatg ctttgatgct tttgctaaac tcaaaatatt   4560

agttttattt tactgttttg aaaggttcaa agcatgatcc atgtaaaaat gtcttctgtg   4620

gggctttctc ccatttctac ttttgttccc ctcatttctt caaagtgctt gtccaggcag   4680

agctgacctt atttgcttac cagttacagg taaacaaagc gtttcctcgt gttgcctctt   4740

gtagccatct ctgtattaga ttaggaaggg aaggagccgt cctactgtcc agtttgtgag   4800

ttctggtaga aagagtgttg aagtttgtta aatgcttgtt ttccatgtat caaaatgtta   4860

tgcctttcct atttattatt gtatgacaaa ttatttttca ctgggcaaaa ataattgtgc   4920

cattgactcc ttgtgtgttt tcttcatgtg tgtttgaaga gttctagctt attaaaaaaa   4980

aaaatctag                                                           4989
```

```
<210> SEQ ID NO 15
<211> LENGTH: 2681
<212> TYPE: DNA
<213> ORGANISM: Bos taurus
<220> FEATURE:
<221> NAME/KEY: mRNA
<222> LOCATION: (1)...(2681)
<223> OTHER INFORMATION: Bovine vacuolar H+-ATPase

<400> SEQUENCE: 15

gaattcggcc gcgaggagac aagatggcgc tgcgggcgat gcgggggatc gtgaacgggg     60

ccgcgcctga gctaccagta cccaccagcg ggctggcggg gtctcgagag caggcgctgg    120

cagtgagccg aaactacctc tcccagcctc gtctcaccta caagactgtc tctggagtga    180

atggtccact agtgatctta gatcatgtaa agtttcccag atatgctgag attgtccact    240

tgacattacc agatggcaca aaaagaagtg ggcaagttct agaagttagt ggctccaaag    300

ctgtggttca ggtatttgaa ggaacatccg gcatagatgc caagaaaaca tcctgtgagt    360

ttactggaga tattctccgc acaccagtgt ctgaggatat gcttggtcga gtattcaatg    420

gatcaggaaa acccattgac cgaggtcctg tggtgttggc cgaagacttc cttgacatca    480

tgggtcagcc aatcaaccct cattttcgca tctacccaga agagatgatt cagactggca    540

tttctgccat cgacggcatg aacagtattg cgaggggaca gaaaatcccc atcttttctg    600

ctgccgggtt accacacaac gagattgcag ctcagatctg tcgccaggct ggtttggtaa    660

agaaatccaa agacgtggta gactacagtg aagaaaactt tgccattgtg tttgctgcta    720
```

-continued

```
tgggagtaaa catggaaaca gcccggttct tcaaatctga ctttgaagaa aatggctcaa    780

tggacaatgt ctgccttttc ttgaatctgg ctaatgaccc aactatcgag aggatcatca    840

ctcctcgcct ggctctgacc accgctgagt ttctggctta ccagtgtgag aagcatgtcc    900

tggtcatcct gacagatatg agttcttacg ctgaagcact tcgagaggtt tcagctgcca    960

gggaagaggt tcctggtcgg cgaggcttcc ccggctacat gtatacggat ttagccacca   1020

tctatgaacg cgctgggcga gtggaaggta gaaatggctc tattacccaa atccctattc   1080

tcaccatgcc caatgatgat atcactcatc ctatccctga cttgactggg tatattactg   1140

agggccagat ctatgtggac agacagctgc acaacagaca gatttaccct cctattaatg   1200

tgctgccctc actctctcgg ttaatgaagt cagctattgg agaaggaatg accaggaagg   1260

atcatgctga tgtgtctaac cagttgtacg catgctatgc tatcggtaag gatgtgcaag   1320

ccatgaaagc tgtggtggga gaagaagccc tgacctcaga tgacctcctt tacttggaat   1380

ttctgcagaa gtttgagaaa aacttcatta ctcagggtcc ctatgaaaat cgaactgtct   1440

atgagacttt ggacattggc tggcagttgc ttcgaatctt ccccaaagaa atgctgaaga   1500

ggatccctca gagtaccctg agcgaatttt accctcgaga ctctgcaaag cactagctgc   1560

tgctgcttgt gcggctcgac cctcttgtca agtgctggtt ctgtttgctg attccttttg   1620

cactcctcca tccacctgtg tgtgggagtt cacctgttac cctgtaatta aagacaaagg   1680

ctaggtaact gttgtgccag tgttcagcgt ttaaactgct aaccgattga gagatccccg   1740

ctcagaacct caccttctgt gctgtcttta aagtggcgga ggtgaggctt gcttaccggt   1800

gtatctattt gtacatagtg gagagctagt tgcgaataat gtcttgtttg ggtctcccaa   1860

accctacctc tcaactccct taagagtatc aactgttttg aagttaaaat gcttcagtct   1920

caaatttagg ggcaaggtgg agactggaag aattctcctt tcagaagaac catgaggctc   1980

gtggctgagc tccctctgga gtactagtgt acctgtgggt ctgtcctctg ctctgtgcag   2040

atgggtttta ctgtctgctt gagttttctt aggaaaagag ttctgttctg ccagtgctgc   2100

gagttgggat tcctgtgtgg ccatctttct ctttgaggcc taaagagtca gcaccactgt   2160

gcagcggcat tctcctgcag ggtggcgtg ccttgtgctg atgaccccac tgggctgcag   2220

tcataggaga actgagactt ggaaaatgct ggggcacagt taagaaaacc tacatcccac   2280

cctcatcttg tgtttatggt ggcttaggtc tctgcattgc cctccagatc ctgaggtggg   2340

gcatggagat gacttgcctt aggtttgtgg atgctttaaa ctctgctcag tcctcaagct   2400

ttctgactca gctctccctt ttctggttga tcttgtggca cgtgtagcaa tgtttctttc   2460

attcctgccc cttcctggct tgagctctta gctgtattct gtgtgcctct gccgtgtctg   2520

ctgtttgggt ctctgtgctg tgtgttctca ggtgcagcca taacttcccc actccgagca   2580

ttccaccttc cagttgtttt tctctgaggg gatgggggg cggtcagcat gattatattt    2640

taatgtagaa aatgtgacat ctcgttataa atgcggaatt c                        2681
```

```
<210> SEQ ID NO 16
<211> LENGTH: 2594
<212> TYPE: DNA
<213> ORGANISM: Homo sapiens
<220> FEATURE:
<221> NAME/KEY: mRNA
<222> LOCATION: (1)...(2594)
<223> OTHER INFORMATION: human vacuolar H+-ATPase

<400> SEQUENCE: 16
```

-continued

```
gaattccggg gacagaggag acaagatggc gctgcgggcg atgcggggga ttgtcaacgg     60
ggccgcaccc gagctacccg tccccaccgg tgggccggcg gtgggatctc gggagcaggc    120
gctggcagtc agtcggaact acctctccca gcctcgcctc acatacaaga cagtatctgg    180
agtcaatggt ccactagtga tcttagatca tgttaagttt cccaggtatg ctgaaattgt    240
ccatttgacc ttaccggatg gcacaaagag aagtgggcaa gttctggaag ttagtggttc    300
caaggcagta gttcaggtat ttgaagggac ttcaggtata gatgctaaga aaacgtcctg    360
tgagtttact ggggatattc tccgaacacc ggtgtctgag gatatgcttg gtcgggtatt    420
caatggatcg ggaaaaccca ttgacagagg tcctgttgta ctggccgaag acttccttga    480
tatcatgggt cagccaatca accctcaatg tcgaatctac ccagaggaaa tgattcagac    540
tggcatttcg gccatcgatg ggatgaacag tattgctagg gggcagaaaa ttcctatctt    600
ctctgctgct gggctaccac acaatgagat tgcagctcag atctgtcgcc aggctggttt    660
ggtaaagaaa tccaaagatg tagtagacta cagtgaggaa aattttgcaa ttgtatttgc    720
tgctatgggt gtaaacatgg aaactgcccg gttcttcaaa tctgactttg aagaaaatgg    780
ctcaatggac aatgtctgcc tctttttgaa cttggctaat gacccaacca ttgagcgaat    840
tatcactcct cgcctggctc taaccacagc tgaatttctg gcgtaccaat gtgagaaaca    900
tgtattggtt attctaacag acatgagttc ttatgctgaa gcacttcgag aggtttcagc    960
agccagggaa gaggtacctg gtcgacgagg ttttccaggt tacatgtata cagatttagc   1020
cacgatatat gaacgcgctg ggcgagtgga agggagaaac ggctcgatta ctcaaatccc   1080
tattctaacc atgcctaatg atgatatcac tcaccccatc ccagacttga ctggctacat   1140
tacagagggg cagatctatg tggacagaca gctgcacaac agacagattt atccacctat   1200
caatgtgctg ccctcactat cacggttaat gaagtctgct attggagaag ggatgaccag   1260
gaaggatcat gccgatgtat ctaaccagct atatgcgtgc tatgctattg gaaaggatgt   1320
gcaagccatg aaagctgtcg ttggagaaga agcccttacc tcagatgatc ttctctactt   1380
ggaatttctg cagaagtttg agaggaactt cattgctcag ggtccttacg aaaatcgcac   1440
tgtctttgag actttggaca ttggctggca gctactccga atcttcccca aagaaatgct   1500
gaagagaatc cctcagagca ccctcagcga attttaccct cgagactctg caaagcatta   1560
gctgctgctt ctgcattgct ccgcgctctt gtgaaatact ggttctgttt tctttattcc   1620
ttttgcactc tcggttccca cctttgtgtt ggagtttacc atgttaccct gtaattaaaa   1680
acaaagaata ggtaacatat tgtgccagtg ttgcaacgtt ttaaactgct aacagacctt   1740
aaaatatccc cctacctggg tcctcagtgc tatgtttaaa gtgctgcagg gatggagtgg   1800
cgttttctta ttgctgtatg tattgtacat agtggagtag ttagttacct gataacagtc   1860
ttgttatttg ggtctcttag accttacctc tcaactccct caagagtacc agtctctgaa   1920
gttataatgc tttggtctct acattagggg caagatccag tctgagagaa gtctcctttg   1980
agaagggcca agaggctctt tcctgagtgt ttgctttcgg tttgttggta tgcctgtatt   2040
gctgggctgt gctgctgctc gaagcagatg gttttgactg tctttttgct ctttcctata   2100
taatgaatag atgagtgaaa ggagttttct ttttctcttt agtacttacg tattgggatt   2160
cctgtgtctt acagctctcc ctctccaaat aatacacaga atcctgcaac tttttgcaca   2220
gctggtatct gtctggtagc agtgagaccc cttgtcttgg tgatccttac tgggtttcca   2280
agcagaggag tcacatgatt acaattgcca gtagagttgt tgtttggggt acaagatgag   2340
aagaaagaaa aacctacagc ctttctacat tctgacatgc taacagtggt ttaagtttct   2400
```

```
aaagtgttta ccagatgctg aaggcaaggg gagggagcag aagcacttat gtttacggat   2460

attttaaact ctgttagaga gcagcctttg aaaatcccca atttggttct gctttttgac   2520

ctctctctac cttttcaggg taatctttgt ggcacaaacg atagcatttc caagctttag   2580

agttttctga attc                                                     2594


<210> SEQ ID NO 17
<211> LENGTH: 1536
<212> TYPE: DNA
<213> ORGANISM: Mus musculus
<220> FEATURE:
<221> NAME/KEY: mRNA
<222> LOCATION: (1)...(1536)
<223> OTHER INFORMATION: mouse vacuolar H+-ATPase

<400> SEQUENCE: 17

atggcgttgc gagcgatgcg gggaatcgtg aacggggccg cacccgaact gcccgtgccc     60

acccgtccgc cgatggccgg agctcgggag caggcgctgg cggtgggccg gaactaccta    120

tcccagcctc gtctcaccta caagactgtc tctggggtga atggtccact agtgatccta    180

gatcatgtga agtttcccag atacgctgag attgtccact tgacattacc agatggcaca    240

aagagaagtg ggcaagtctt agaagttagt ggctccaaag cagtggttca ggtatttgaa    300

gggacatctg gtatagacgc caagaaaaca tcctgtgagt ttactggaga tattctccga    360

acaccagtgt ctgaggatat gcttggtcgg gtattcaacg gatcaggaaa acccattgac    420

cgaggccctg tggtgctggc tgaagacttc cttgacatca tgggtcagcc aatcaaccct    480

cagtgtcgga tctatccaga agagatgatt cagacgggca tttccgccat cgatggcatg    540

aacagtattg ctaggggaca gaaaatcccg atcttttctg ctgctggatt accccataac    600

gagattgcag ctcagatctg tcgccaggct ggtttggtaa agaaatccaa agatgtagtg    660

gactatagtg aagaaaattt tgccattgtg tttgctgcta tgggagtaaa catggaaaca    720

gcccggttct ttaaatctga ctttgaagaa aatggctcaa tggacaatgt ctgcctgttt    780

ttgatcttgc ctaatgaccc aaccattgag cggatcatca ctccctgcct ggctctgacc    840

acggccgagt ttctggcata tcagtgtgag aagcacgtgc tggtgatcct gacggacacg    900

agctcctatc ccgaagcgct tcgagaggtt tcagctgcca gggaagaggt ccctggtcgg    960

cgaggcttcc caggctacat gtataccgac ttagccacaa tctatgaacg tgccggtcga   1020

gtggaaggta gaaacggctc tattacccaa atccctattc tcaccatgcc caatgacgat   1080

atcactcatc ccatccctga cttgactggg tacattactg agggccagat ctatgtggac   1140

agacagctgc acaacagaca gatttaccct cctattaatg tgctgccctc actctctcgg   1200

ttaatgaagt cacctatcgg agaaggaatg accagaaagg atcacgctga tgtgtctaac   1260

cagttgtatg cgtgctatgc catcggtaag gacgtgcaag ccatgaaagc cgtggtggga   1320

gaggaagccc tgacctcgga tgatctgctt tacctggaat ttctgcagaa gtttgagaag   1380

aacttcatta ctcagggtcc ctatgaaaac cgaactgttt atgagacttt ggacattggc   1440

tggcagttgc ttcgaatctt ccccaaagaa atgctgaaga gaatccctca gagcaccctg   1500

agcgaatttt accctcgaga ctctgcaaag cactag                             1536


<210> SEQ ID NO 18
<211> LENGTH: 2820
<212> TYPE: DNA
<213> ORGANISM: Homo Sapiens
<220> FEATURE:
```

<221> NAME/KEY: mRNA
<222> LOCATION: (1)...(2820)
<223> OTHER INFORMATION: human vacuolar H+-ATPase (56,000 subunit -HO57)

<400> SEQUENCE: 18

```
aagatggcgc tgcgggcgat gcgggggatt gtcaacgggg ccgcacccga gctacccgtg     60
cccaccggtg ggccggcggt gggagctcgg gagcaggcgc tggcagtcag tcggaactac    120
ctctcccagc ctcgcctcac atacaagaca gtatctggag tcaatggtcc actagtgatc    180
ttagatcatg ttaagtttcc caggtatgct gaaattgtcc atttgacctt accggatggc    240
acaaagagaa gtgggcaagt tctggaagtt agtggttcca aggcagtagt tcaggtattt    300
gaagggactt caggtataga tgctaagaaa acgtcctgtg agtttactgg ggatattctc    360
cgaacaccgg tgtctgagga tatgcttggt cgggtattca atggatcggg aaaacccatt    420
gacagaggtc ctgttgtact ggccgaagac ttcttggata tcatgggtca gccaatcaac    480
cctcaatgtc gaatctaccc agaggaaatg attcagactg gcatttcggc catcgatggg    540
atgaacagta ttgctagggg gcagaaaatt cctatcttct ctgctgctgg gctaccacac    600
aatgagattg cagctcagat ctgtcgccag gctggtttgg taaagaaatc caaagatgta    660
gtagactaca gtgaggaaaa ttttgcaatt gtatttgctg ctatgggtgt aaacatggaa    720
actgcccggt tcttcaaatc tgactttgaa gaaaatggct caatggacaa tgtctgcctc    780
tttttgaact tggctaatga cccaaccatt gagcgaatta tcactcctcg cctggctcta    840
accacagctg aatttctggc gtaccaatgt gagaaacatg tattggttat tctaacagac    900
atgagttctt atgctgaagc acttcgagag gtttcagcag ccagggaaga ggtacctggt    960
cgacgaggtt ttccaggtta catgtataca gatttagcca cgatatatga acgcgctggg   1020
cgagtggaag ggagaaacgg ctcgattact caaatcccta ttctaaccat gcctaatgat   1080
gatatcactc accccatccc agacttgact ggctacatta cagaggggct gatctatgtg   1140
gacagacagc tgcacaacag acagatttat ccacctatca atgtgctgcc ctcactatca   1200
cggttaatga agtctgctat tggagaaggg atgaccagga aggatcatgc cgatgtatct   1260
aaccagctat atgcgtgcta tgctattgga aaggatgtgc aagccatgaa agctgtcgtt   1320
ggagaagaag cccttacctc agatgatctt ctctacttgg aatttctgca gaagtttgag   1380
aggaacttca ttgctcaggg tccttacgaa aatcgcactg tctttgagac tttggacatt   1440
ggctggcagc tactccgaat cttcccccaaa gaaatgctga agagaatccc tcagagcacc   1500
ctcagcgaat tttaccctcg agactctgca aagcattagc tgctgcttct gcattgctcc   1560
gcgctcttgt gaaatactgg ttctgttttc tttattcctt ttgcactctc ggttcccacc   1620
tttgtgttgg agtttaccat gttaccctgt aattaaaaac aaagaatagg taacatattg   1680
tgccagtgtt gcaacgtttt aaactgctaa cagaccttaa aatatccccc tacctgggtc   1740
ctcagtgcta tgtttaaagt gctgcaggga tggagtggcg ttttcttatt gctgtatgta   1800
ttgtacatag tggagtagtt agttacctga taacagtctt gttatttggg tctcttagac   1860
cttacctctc aactccctca agagtaccag tctctgaagt tataatgctt tggtctctac   1920
attagggaca agatccagtc tgagagaagt ctcctttgag aagggccaag aggctctttc   1980
ctgagtgttt cgtttcggtt gttggtatgc ctgtattgct gggctgtgct gctgctcgaa   2040
gcagatggtt ttgactgtct tttgctcttt tcctatataa tgaatagatg agtgaaagga   2100
gttttctttt tctctttagt acttacgtat tgggattcct gtgtcttaca gctctccctc   2160
tccaaataat acacagaatc ctgcaacttt ttgcacagct ggtatctgtc tggtagcagt   2220
```

```
gagacccctt gtcttggtga tccttactgg gtttccaagc agaggagtca catgattaca   2280

attgccagta gagttgttgt ttggggtaca agatgagaag aaagaaaaac ctacagcctt   2340

tctacattct gacatgctaa cagtggttta agtttctaaa gtgtttacca gatgctgaag   2400

gcaaggggag ggagcagaag cacttatgtt tacggatatt ttaaactctg ttagagagca   2460

gcctttgaaa atccccaatt tggttctgct ttttgacctc tctctacctt ttcagggtaa   2520

tctttgtggc acaaacgata gcatttccaa gctttagagt tttctgaatt cctgcgcctt   2580

cctgacgtga gccctgagcg atcttctatg cagttctgcc atgcgtcctg ttggtctctc   2640

gtgttcttt gttacttggg tgcaatagca acttccctac cccgtgcatt ccatctttca   2700

gttgtgtaa agttcttcac ttttttctct gagggctggg ggttggggga gtcagcatga   2760

tatatttta atgtagaaaa aatgtgacat ctggatataa aatgaaaata aatgttaaat   2820
```

<210> SEQ ID NO 19
<211> LENGTH: 2457
<212> TYPE: DNA
<213> ORGANISM: Homo sapiens
<220> FEATURE:
<221> NAME/KEY: mRNA
<222> LOCATION: (1)...(2457)
<223> OTHER INFORMATION: human vacuolar H+-ATPase B subunit

<400> SEQUENCE: 19

```
gatgctaaga aaacgtcctg tgagtttact ggggatattc tccgaacacc agtgtctgag     60

gatatgcttg gtcgggtatt caatggatcg ggaaaaccca ttgacagagg tcctgttgta    120

ctggctgaag acttccttga tatcatgggt cagccaatca accctcaatg tcgaatctac    180

ccagaggaaa tgattcagac tggcatttca gccatcgatg gaatgaacag tattgccagg    240

gggcagaaaa ttcctatctt ctctgctgct gggctaccac acaatgagat tgcagctcag    300

atctgtcgcc aggctggttt ggtaaagaaa tccaaagatg tagtagacta cagtgaggaa    360

aattttgcaa ttgtatttgc tgctatgggt gtaaacatgg aaaccgcccg attcttcaaa    420

tctgactttg aagaaaatgg ctcaatggac aatgtctgcc tctttttgaa cttggcgaat    480

gacccaacca ttgagcgaat tatcactcct cgcctggctc taaccacagc tgaatttctg    540

gcataccaat gtgagaaaca cgtactggtt atcctcacag acatgagttc ttacgctgaa    600

gcacttcgag aggtttcagc agccagggaa gaggttcctg gtcgacgagg cttcccaggt    660

tacatgtata cagatttagc cacaatatat gaacgcgctg ggcgagtgga agggagaaac    720

ggctcgatta ctcaaatccc tattcttacc atgcctaatg atgatatcac tcacccaatc    780

ccggacttga ctggctacat tacagagggg cagatctatg tggacagaca gctacacaac    840

agacagattt atccacctat caatgtgcta ccgtcactat cacggttaat gaagtctgct    900

attggagaag ggatgaccag gaaggatcat gccgatgtat ctaaccagct gtatcgcgcg    960

tatgctattg ggaaggatgt acaagccgtg aaagctgtcg ttggagaaga agcccttacc   1020

tcagatgatc ttctctactt ggaatttctg cagaagtttg agaggaactt tattgctcag   1080

ggtccttacg aaaatcgcac tgtctttgag actttggaca ttggctggca gctgctccga   1140

atcttcccca aagaaatgct gaagagaatc cctcagagca ccctcagcga attttaccct   1200

cgagactctg cgaacgatta gctgccgctt ctgcactgct ccacactctt gtgaaatact   1260

ggttctattt tctttattcc ttttgcgctc cccaatcccc acctttgtgt tggagtttac   1320

tgtgttaccc tgtaattaaa aacaaagaat aggtaacata ttgtgccagt gttgcaacgt   1380
```

-continued

```
tttaaactgc taacagacct taaaatattc cgttcagaaa acctgggtcc tcagtgctat   1440

gtttaaagta gctgcaggga tggagtggcg ttttcctatt gctgtatgta ttgtacatag   1500

cggagtagtt agttacctga taacggtctc attatttggg cctcttagac cttacctctc   1560

aactccctca agagtaccag tctctgaagt tataatgctt tggtctctac attaggggca   1620

agatccggtc taaaagaagt ctcctttgag aagggccaag aggtctttcc tgagtgtatg   1680

ctttcggttt gttggtatgc ctgtgttgct gggctgtact gatactcgaa gcagatggtt   1740

ttaactgtgt acttactctt actgtataat gaatagatga gtgaaagcag ttttcttttt   1800

ctctttagta catatgtatt gggattcctg tgtcttacag ctctccctct cctaaataat   1860

acacagaatc ctgcaacttt tgcacagcgg tgtctgtcag gtagcagtga ggccccttgt   1920

cttggtgatc cttactggat ttccaagcag aggagtcacg tgattaaaat cgctaataga   1980

gttgttgttt gggggacaag ataagaagaa aggaaaaacc tacagccttt ctacattctg   2040

acatactaac agtggtttca gtttctaaag cgtttaccag atgcgaaggc aaggtgggga   2100

gcaaacgcac ttatgtttac ggatatttta aactctgtta gagagcagcc tttgaaaatc   2160

ccgaattttg ttctactttt tgacctctct ctaccttttc agggtaatct ttgtggcaca   2220

aacaatagca tttccaagct ttagagttct ctgaattcct gcgccttcct gaacgtgagc   2280

cctgagcgat cttctatgca gttctgccat gtgtcctgtt tggtctctct gtgttctttg   2340

ttacttgtgc aatagcgact tccctactcc gtgcattcca tctttcatgt tgtgtaaagt   2400

tcttcacttt tttctttgag ggggtggggg tgggggggag tcagcatgat tatattt      2457
```

```
<210> SEQ ID NO 20
<211> LENGTH: 2676
<212> TYPE: DNA
<213> ORGANISM: Bos taurus
<220> FEATURE:
<221> NAME/KEY: mRNA
<222> LOCATION: (1)...(2676)
<223> OTHER INFORMATION: bovine vacuolar H+-ATPase B subunit

<400> SEQUENCE: 20

aagatggcgc tgcgggcgat gcgggggatc gtgaacgggg ccgcgcctga gctaccagta     60

cccaccagcg ggcccctggc ggggtctcga gagcaggcgc tggcagttag ccggaactac    120

ctctcccagc ctcgtctcac gtacaagaca gtatcaggag ttaatggtcc actagtgatc    180

ttagaccatg ttaagtttcc cagatatgct gagattgtgc acttaacact acctgacggg    240

acgaagcgga ctgggcaagt tctagaagtt agtggttcca aagctgtggt tcaggtattt    300

gaagggactt caggtataga tgccaagaaa acgtcctgtg agtttactgg ggatattctc    360

cgaacgccag tgtctgagga tatgcttggt cgggtattca atggatcagg aaaacccatt    420

gacagaggtc ctgttgtcct ggctgaagac ttccttgaca tcatgggcca gccaatcaac    480

cctcaatgtc gaatctatcc agaggagatg attcagactg gcatttcggc catagatggc    540

atgaacagta ttgctcgggg gcagaagatt cctatcttct ctgctgctgg cttaccgcac    600

aatgagattg cagctcaaat ctgtcgccag gctggtttgg taaaaaagtc caaagatgta    660

gtggactaca gtgaggaaaa ttttgcgatt gtatttgctg ctatgggtgt aaacatggaa    720

actgcccggt tcttcaaatc tgactttgag gaaaatggct caatggacaa tgtctgcctg    780

tttttgaact tggctaatga cccaactatt gagcgaatta tcactcctcg attggctcta    840

accacggccg agttcctggc ctatcagtgt gagaaacatg tattggttat cctaacagac    900

atgagttctt atgctgaagc acttcgagag gtttcagcag ccagggaaga ggttcctggt    960
```

-continued

```
cgacgaggtt tcccaggtta catgtataca gatttagcca caatatatga acgtgctggt   1020

cgagtggaag gtcgaaatgg ctctattact caaattccta ttctcaccat gcctaacgat   1080

gatatcactc acccaatccc tgacttgact ggatatatta cagaggggca gatctatgtg   1140

gacagacagc tacacaacag acagatttat ccaccaatta atgtgctgcc ctccttgtcg   1200

cggttgatga agtctgctat tggagaaggc atgaccagaa aggatcacgc cgatgtgtct   1260

aaccagctgt atgcgtgcta tgctattggt aaggatgtac aagccatgaa agctgtcgtt   1320

ggagaagaag ctcttacctc agatgatctt ctttacttgg aatttctgca gaagtttgag   1380

aggaacttta ttgctcaggg tccttatgaa aaccgcactg tgtatgagac tttggacatt   1440

ggctggcaac tgctccgaat cttccccaaa gaaatgctga agaggatccc tcagagcacc   1500

ctgagcgaat tctaccctcg agactctgcg aacagttagc tgctacttca tcgctggctc   1560

gatgctcttg tgaagtactg gttctatttt ctttattcct ttttgcactc ccccatcccc   1620

acctttgtgt tggagtttac tgtgttaccc tgtaattaaa aacaaagact aggtaacata   1680

ctgtgccagt gttgcaatgt tttaaactgc taacagactt taaaatatcc cctgtttaga   1740

aaaaccttgg atccttccaa cgctttcttc aaagcagctg agagttggag gtggagtttt   1800

tcatcaatgt gtgtatttgt acatagtggt gtaccttact gcctagtgtc ctcattattg   1860

gggtctctta gcccttgcct ctccaccctg gcaatagtat cactatctga agttacagtg   1920

ctttggtctc cagctaggga caagagaggg gtctgaaagc acttctcaga gccaagaggc   1980

tttcctgagt gctggtttta gattttggta tgcctcaggg tctgtgccgc tgctctcacg   2040

agatggtttt tactgcccgc ctgctctttc ctgtctaata gatagactag aaaaggagtt   2100

ccatttcctc tttggtacgg attagcttca acctccatgt cttactgctc ttcctcccta   2160

tgataacaca gaatcatgcc acttttgccc tgctggcaat cgctctgagc agcaagatgc   2220

cctgtggtaa tgatccttac tgggtttcct tgcagaagaa tcatcattac aataattaat   2280

agaactttgc ttggaaagag ttgggataca attgtttaag agttaaaaaa aaaatccttt   2340

ctacacttgg acgtgccaac agtggtttta agtttctaga atgttgacca gatgctagaa   2400

aggcaagtgg ggaagagaaa gcacttctgt ttatggattt tttaatttaa tgtatggata   2460

ttttaaactc tgttagacag tagcctttgg gaaatcccca ttgggtcctg cttttcaacc   2520

tctttgcttt tcagggtagt tcttgtggca caagtgacag cattaaaagc ttttagcctt   2580

ttaattcctc ctccttcctg ctgcgagccc tgagctgtct tctatgcact tctgacgtgt   2640

ctcctgttgg gtctctgtgt tctttgttcc ttgccg                             2676
```

<210> SEQ ID NO 21
<211> LENGTH: 3035
<212> TYPE: DNA
<213> ORGANISM: Gallus gallus
<220> FEATURE:
<221> NAME/KEY: mRNA
<222> LOCATION: (1)...(3035)
<223> OTHER INFORMATION: gallus vacuolar H+-ATPase

<400> SEQUENCE: 21

```
cggcggatgg tgaacggcgc cgggcccggc ggggcgcgcg agcaggcggc ggcgctgacg     60

cgggactttc tgtcccagcc gcgcctcact tataaaaccg tgtctggtgt gaatggcccc    120

ctggttatct tggatcaagt gaagtttcct aggtacgcgg agattgtcca cttgactctt    180

cctgatggca ccagaagaag tgggcaggtt ctggaagtca gtggctccaa agctgtggtt    240
```

-continued

```
caggtatttg agggcacttc aggtattgat gctaagaaaa catcctgtga gtttactggg    300

gacattcttc gaacccctgt ctctgaagat atgcttggca gagtatttaa tggatcagga    360

aaacccatag acagaggccc cgctgttttg gctgaagact tcctggatat aatgggtcag    420

ccaatcaatc cccagtgtcg aatctatcca gaagagatga ttcagactgg catttctgca    480

atagacggta tgaacagcat tgccaggggg cagaaaatcc ccatattctc tgctgctggt    540

ttgccccaca atgagattgc agctcagatc tgtcgccagg ctggcttggt gaagaaatcc    600

aaagatgtga tggattacag tgaagaaaat tttgccatcg tgtttgctgc tatgggtgtg    660

aacatggaaa ctgctcggtt cttcaaatca gactttgagg aaaatgggtc catggacaac    720

gtgtgtctgt tcttgaattt ggccaatgac ccaaccattg aacgcattat cacacctcgt    780

ctggctctaa caacggcaga gttcttggca tatcagtgtg agaagcatgt gctggtcatt    840

ctgacagata tgagctccta tgctgaagct ctacgagagg tctcagcagc tagagaggag    900

gtacctggcc gtcgtggttt cccaggttac atgtacactg acttggctac tatatatgaa    960

cgtgctgggc gtgtggaagg cagaaatggc tcaattactc agattcccat tcttaccatg   1020

cccaatgatg atattactca tcctatccct gacttgactg gatacatcac tgagggacaa   1080

atctatgtgg ataggcagct gcacaacaga cagatttacc cacctattaa tgtactgccc   1140

tccttgtctc gactgatgaa gtcagctatt ggagagggca tgaccaggaa ggatcatgca   1200

gatgtatcca accaactgta tgcctgctat gctattggga aggacgtgca ggccatgaag   1260

gctgtagttg gtgaggaagc tcttacctca gatgatcttc tttatctgga gtttctgcag   1320

aagtttgaga agaacttcat tgctcagggt ccttatgaaa atcgtactgt ttacgagacc   1380

ttggacattg gatggcagct tttgcgaatc ttccccaagg agatgttgaa gagaattccc   1440

caaacaacac tggctgaatt ctatcctcga gattcgactg caaaacacta accacaactt   1500

cgtctccaac cccttgctct gtgaaatgct gtttgttttc ctttttttcat gtgttgatgt   1560

ttacttgtcg cccttacgat taaaaccaag aataggtgac atttgtgcca gtgttccaat   1620

gtacactgat accagttctt aaaatagccc ttcttctaaa gcctggatct tcaggaagac   1680

ctttaggcca gctcttacat atgtgcaata gctattgtta agctttcttt tttgtttgaa   1740

ctggaccttt tataggcatt tcaaatgaat gtcagaggat taccagaaac tgcaaatctt   1800

taattccaaa ccaggagcat gtgggttaga aagactaaat gtgacttaat gtccaaagca   1860

tctgctcatt ttgatcacgt gcagttgcct tgctgctggt agaacagatg gctctctgct   1920

gtcctgctgc tgtgcctgaa gaccaggcta acatgtgcaa agtgtggtgc acaatgtcat   1980

atctctaaaa aatgcaagtc actgatttaa ctgtggttta aaattcttaa aggcgtgtat   2040

gaactaagga cactagtgag catgctaagt gcttttctgc tagcaaggtc tcagtgcaga   2100

ggtcacaggc cagtgggttg cttacctgaa ggcagcgtgt tatggctcag tggctgaatt   2160

aaaggtccaa attgtacctt gaagcttgca aagaaagatt cctacttaac ttttcttttt   2220

cattgtggaa atgccagaga cgtgtgacag cagctgaagc gctctgagat cagtagtgtc   2280

agtaggttaa gactggctaa ttcaaggctc catgctgcta ttgaagggga tgatatgaga   2340

tgtaaagaaa acctctttat gcgagacaca attgtactgg tgggaggtca gcttttaaaa   2400

tgcgttggac taaacaatgc aacagcagaa agcaacctaa tgcatgaaag gatattgaat   2460

tctgctacaa agcgtgctgt aggtggcgct gggtcctggg tcgtgttcag agctcttgtg   2520

gtttgcactc caggcacaga tttggctagc caggagagct cagcattccc tatcactgcg   2580

aacttggcta gcctcttcag tgttatttct tactttaaac tggttcagac gaggctcaga   2640
```

-continued

```
gcccagtgct ggcaggcttg ctggcttttt tttttttccc aggcttaatg taatcttatc   2700

tctggtctag ctcaccaaag catgttgcac ctctctgaac gccttcagtg cttgtctagg   2760

aaggtgctaa cgtgactcaa aggatagcgt gctaattcca gctttccctg atgtttcctg   2820

tgtgcagttc tatgggtttg ttcagtgttc tctgtaactt ggacacaata gtaactttat   2880

ccagtgcat tccactctaa agctgtgtca agtctatttt tttctcttga ggtaggaatg   2940

gaggctgca agtgttggca tgagaatact ttaatgtaga gaatatctaa ataaattaaa   3000

atgaaaggt gttgaacaaa aaaaaaaaaa aaaaa                              3035


<210> SEQ ID NO 22
<211> LENGTH: 1737
<212> TYPE: DNA
<213> ORGANISM: Homo sapiens
<220> FEATURE:
<221> NAME/KEY: mRNA
<222> LOCATION: (1)...(1737)
<223> OTHER INFORMATION: human CD44R

<400> SEQUENCE: 22

ccagcctctg ccaggttcgg tccgccatcc tcgtcccgtc ctccgccggc ccctgccccg     60

cgcccaggga tcctccagct cctttcgccc gcgccctccg ttcgctccgg acaccatgga    120

caagttttgg tggcacgcag cctggggact ctgcctcgtg ccgctgagcc tggcgcagat    180

cgatttgaat ataacctgcc gctttgcagg tgtattccac gtggagaaaa atggtcgcta    240

cagcatctct cggacggagg ccgctgacct ctgcaaggct ttcaatagca ccttgcccac    300

aatggcccag atggagaaag ctctgagcat cggatttgag acctgcaggt atgggttcat    360

agaagggcac gtggtgattc cccggatcca ccccaactcc atctgtgcag caaacaacac    420

aggggtgtac atcctcacat ccaacacctc ccagtatgac acatattgct tcaatgcttc    480

agctccacct gaagaagatt gtacatcagt cacagacctg cccaatgcct ttgatggacc    540

aattaccata actattgtta accgtgatgg cacccgctat gtccagaaag gagaatacag    600

aacgaatcct gaagacatct accccagcaa ccctactgat gatgacgtga gcagcggctc    660

ctccagtgaa aggagcagca cttcaggagg ttacatcttt tacacctttt ctactgtaca    720

ccccatccca gacgaagaca gtccctggat caccgacagc acagacagaa tccctgctac    780

caatatggac tccagtcata gtacaacgct tcagcctact gcaaatccaa acacaggttt    840

ggtggaagat ttggacagga caggacctct ttcaatgaca acgcagcaga gtaattctca    900

gagcttctct acatcacatg aaggcttgga agaagataaa gaccatccaa caacttctac    960

tctgacatca agcaatagga atgatgtcac aggtggaaga agagacccaa atcattctga   1020

aggctcaact actttactgg aaggttatac ctctcattac ccacacacga aggaaagcag   1080

gaccttcatc ccagtgacct cagctaagac tgggtccttt ggagttactg cagttactgt   1140

tggagattcc aactctaatg tcaatcgttc cttatcagga gaccaagaca cattccaccc   1200

cagtgggggg tcccatacca ctcatggatc tgaatcagat ggacactcac atgggagtca   1260

agaaggtgga gcaaacacaa cctctggtcc tataaggaca ccccaaattc cagaatggct   1320

gatcatcttg gcatccctct tggccttggc tttgattctt gcagtttgca ttgcagtcaa   1380

cagtcgaaga aggtgtgggc agaagaaaaa gctagtgatc aacagtggca atggagctgt   1440

ggaggacaga aagccaagtg gactcaacgg agaggccagc aagtctcagg aaatggtgca   1500

tttggtgaac aaggagtcgt cagaaactcc agaccagttt atgacagctg atgagacaag   1560
```

-continued

```
gaacctgcag aatgtggaca tgaagattgg ggtgtaacac ctacaccatt atcttggaaa   1620

gaaacaaccg ttggaaacat aaccattaca gggagctggg acacttaaca gatgcaatgt   1680

gctactgatt gtttcattgc gaatcttttt tagcataaaa ttttctactc tttttaa      1737


<210> SEQ ID NO 23
<211> LENGTH: 1297
<212> TYPE: DNA
<213> ORGANISM: Homo sapiens
<220> FEATURE:
<221> NAME/KEY: mRNA
<222> LOCATION: (1)...(1297)
<223> OTHER INFORMATION: human CD44

<400> SEQUENCE: 23

cctgccccgc gcccagggat cctccagctc ctttcgcccg cgccctccgt tcgctccgga     60

caccatggac aagttttggt ggcacgcagc ctggggactc tgcctcgtgc cgctgagcct    120

ggcgcagatc gatttgaata tgacctgccg ctttgcaggt gtattccacg tggagaaaaa    180

tggtcgctac agcatctctc ggacggaggc cgctgacctc tgcaaggctt tcaatagcac    240

cttgcccaca atggcccaga tggagaaagc tctgagcatc ggatttgaga cctgcaggta    300

tgggttcata gaagggcacg tggtgattcc ccggatccac cccaactcca tctgtgcagc    360

aaacaacaca ggggtgtaca tcctcacatc caacacctcc cagtatgaca catattgctt    420

caatgcttca gctccacctg aagaagattg tacatcagtc acagacctgc ccaatgcctt    480

tgatggacca attaccataa ctattgttaa ccgtgatggc acccgctatg tccagaaagg    540

agaatacaga acgaatcctg aagacatcta ccccagcaac cctactgatg atgacgtgag    600

cagcggctcc tccagtgaaa ggagcagcac ttcaggaggt tacatctttt acaccttttc    660

tactgtacac cccatcccag acgaagacag tccctggatc accgacagca cagacagaat    720

ccctgctacc agagaccaag acacattcca ccccagtggg gggtcccata ccactcatgg    780

atctgaatca gatggacact cacatgggag tcaagaaggt ggagcaaaca caacctctgg    840

tcctataagg acaccccaaa ttccagaatg gctgatcatc ttggcatccc tcttggcctt    900

ggctttgatt cttgcagttt gcattgcagt caacagtcga agaaggtgtg ggcagaagaa    960

aaagctagtg atcaacagtg gcaatggagc tgtggaggac agaaagccaa gtggactcaa   1020

cggagaggcc agcaagtctc aggaaatggt gcatttggtg aacaaggagt cgtcagaaac   1080

tccagaccag tttatgacag ctgatgagac aaggaacctg cagaatgtgg acatgaagat   1140

tggggtgtaa cacctacacc attatcttgg aaagaaacaa ccgttggaaa cataaccatt   1200

cagggagct gggacactta acagatgcaa tgtgctactg attgtttcat tgcgaatctt    1260

tttagataa aatttttact ttaaaaaaaa aaaaaaa                             1297


<210> SEQ ID NO 24
<211> LENGTH: 1177
<212> TYPE: DNA
<213> ORGANISM: Mus musculus
<220> FEATURE:
<221> NAME/KEY: mRNA
<222> LOCATION: (1)...(1177)
<223> OTHER INFORMATION: mouse CD44

<400> SEQUENCE: 24

gaattctgcg ccctcggttg gctccggacg ccatggacaa gttttggtgg cacacagctt     60

ggggactttg cctcttgcag ttgagcctgg cacatcagca gatcgatttg aatgtaacct    120

gccgctacgc aggtgtattc catgtggaga aaaatggccg ctacagtatc tcccggactg    180
```

-continued

```
aggcagctga cctctgccag gctttcaaca gtaccttacc caccatggac caaatgaagt    240

tggccctgag caagggtttt gaaacatgca ggtatgggtt catagaagga aatgtggtaa    300

ttccgaggat tcatcccaac gctatctgtg cagccaacca cacaggagta tatatcctcg    360

tcacgtccaa cacctcccac tatgacacat attgcttcaa tgcctcagcc cctcctgaag    420

aagactgtac atcagtcaca gacctaccca attccttcga tggaccggtt accataacta    480

ttgtcaaccg tgatggtact cgctacagca agaagggcga gtatagaaca caccaagaag    540

acatcgatgc ttcaaacatt atagatgacg atgtcagcag cggctccacc atcgagaaga    600

gcaccccaga aggctacatt ttgcacacct accttcctac tgaacagcct actggagatc    660

aggatgactc cttctttatc cggagcacct tggccaccag agatcgagac tcatccaagg    720

actccagggg gagttcccgc actgtgactc atggatccga attagctgga cactcaagtg    780

cgaaccagga cagtggagtg accacaactt ctggtcctat gaggagacct cagattccag    840

aatggctcat catcttggca tctctcctgg cactggctct gattcttgcc gtctgcatcg    900

cggtcaatag taggagaagg tgtgggcaga agaaaaagct ggtgatcaac ggtggcaatg    960

ggacagtgga agacaggaaa cccagtgagc tcaacgggga ggccagcaag tctcaggaaa   1020

tggtgcattt ggtgaacaag gaaccatcag agaccccaga ccagtgtatg acagctgacg   1080

agacccggaa tctgcagagt gtggacatga agattggggt gtagtgccta cgccattaac   1140

ttgaaaagac agcacgattg gaaacgtcat tgaattc                            1177
```

```
<210> SEQ ID NO 25
<211> LENGTH: 1089
<212> TYPE: DNA
<213> ORGANISM: Cricetulus
<220> FEATURE:
<221> NAME/KEY: mRNA
<222> LOCATION: (1)...(1089)
<223> OTHER INFORMATION: hamster CD44

<400> SEQUENCE: 25

atggacaagt tttggtggca cgcagcttgg ggactctgcc tcttgccgct gagcctggcg     60

cacgagcaga tcgatttgaa cataacctgc cgctatgcag gtgtattcca cgtggagaaa    120

aatggccgct acagcatctc acggactgag gcagctgacc tctgccaagc tttcaacagc    180

actctgccca ccatggacca gatggtgatg gccctgagca agggctttga aacatgcagg    240

tatgggttca tagaaggcca cgtggtgatc ccgaggatcc agcccaatgc catctgtgca    300

gccaaccaca ctggggtgta tatcctcaca tccaacacat ctcactacga tacatattgc    360

ttcaatgcct cagcacccct tgaagaagac tgtacatctg tcacagacct gcccaattcc    420

ttcgaaggac cagttaccat aactattgtc aaccgtgatg gtacccgcta cagcaagaag    480

ggcgagtata gaacacacca agaagacatt gatgcctcaa ataccacaga tgatgatgtc    540

agcagcggat cctccagtga gaagagcacc tcagggggct atgttttcca cacctacctt    600

cccactatac actcaactgc agaccaggat gatccctact tcatcgggag caccatggcc    660

accagagacc aagactcatc catggatccc agggggaatt ccctcactgt gactgatgga    720

tccaaattaa ctgaacactc aagtgggaat caagacagtg ggcttaactc aacttctcgt    780

cctggaggaa aacctcgagt tccagaatgg ctcatcgtct tggcatctct cctggcgctg    840

gctctgattc ttgctgtttg cattgctgtc aacagtagga gaaggtgtgg acagaagaaa    900

aagctggtga tcaacagtgg caatggaaag gtggaggaca ggaagccaag tgagctcaac    960
```

-continued

```
gggaggcca gcaagtctca ggaaatggtg catttggtga acaaggaacc atcagagact    1020

ctgaccagt ttatgacagc tgatgagacc cggaatctgc agaatgtgga catgaagatt    1080

gggtgtag                                                            1089
```

```
<210> SEQ ID NO 26
<211> LENGTH: 4632
<212> TYPE: DNA
<213> ORGANISM: Homo sapiens
<220> FEATURE:
<221> NAME/KEY: mRNA
<222> LOCATION: (1)...(4632)
<223> OTHER INFORMATION: human LOT1

<400> SEQUENCE: 26

ccgtgctcac agctcaacaa cgcggggcct tggcgcgcgg ggcgcttccc cgggtcgccg      60

tcatggccgc ggaggtggca cgcccgagcg gcctcgcctg agctccgggg gtcgtcgccc     120

cgcagggatt gctgtcacgt ctaatgtggc tgctgcctcg tgtcacatct gaaactcatc     180

tgtacctcac ttanaaagtg gttctgatta gacaagactt ttcgttgcag tcgacagaaa     240

cctaatggga ccattgaaga attccaaaca ggcaagtgac aggaacatat ttgcatgtta     300

gaagaatcag cctggcagca gcattgtgat tagaatgaag gggaaccgtc caaaaacaga     360

ctggggaacc aatatggatc tgcctctagc atgcggaaat atctctctac actgacctaa     420

ctgactcact aagcttgtgg tttgtttaaa ggaagccaca tgaaaattga gtttgggcca     480

atagagtgaa ctcgttctcc attctctagc atccctcccc atgcaaccac cctatccctg     540

ccaagtttct gggcaccaca gattggaaag tagcctcctg taggtatttg cccatgttaa     600

gtggtggggt ctctttctgt cttcccttct tggtctcacc tgtctggtgt gacaagggaa     660

gcatgtgcca accaaggcta gacccttgtg agaccagagc agccccactt tcggtaaagc     720

aagcaacctc tgcttacttg cccaacacac cctagcttcc gtgttccttg ccttgtgagt     780

tatcttcttg ggtacaattt aacacagcgt tcccacctcc ttataactaa aatagctaga     840

gggggctttg tgcctcaaac cccaaggaga ccatcttggc aatctctgcc tctgcaacag     900

ggcacttgct ccctgggcaa ctcctttccc aggtcatctt ctcccttgac atgcccatca     960

gatttaatag tgtgcctatt tggcagaaaa atggggtccc ttggttgctg attcttagga    1020

atgtgaggtt ctcccagcca gagctctcag cactaaaagt tctagtctct gcgtaatggc    1080

cggcatatct ttggcgtatc taaaatcctc ttcagtttcc agcagggtct ttataagctt    1140

cttctgaagg tctcagacat tcagccacgg aactcaagtg gaatttgttt ggataacgtg    1200

actgatttca aagcccggac ccttagacgt gcccatttgg tgctgcaagt actgaacatt    1260

actacaacat cttacagtca acaaatttga cacattaaag atttatatcc tttcttttgg    1320

gttaggatct tctctcccct aaagcatctc agtttccagc atgcaatcat ttccatctta    1380

tggaaatcag ccatcccgct ccgtgccagc atgctaccct gggaggcaca tccaggcttg    1440

ggaaacgggg gtgtcctgga tctcatgact ccagcagcac cagctgctct ctttcctctt    1500

ccaagtagac ttccgttccc cccccacttg ggtgtttttg tttgttttag caattcagag    1560

ctcaagataa agaccttaaa gataactttg tgtgtctctc cctttctagg tatttgcata    1620

ggaatcagag gagttaatct tgtttgaatc ttcagacaaa cttctgggag gactcggtcc    1680

ctgcctcgca gcagatgttt ccctgtcact cagtagccaa tccgggggac ccaggacatg    1740

ccccagctat agtgatgcag attacctttc tgctcctgaa tcgcacctgt gcctcagact    1800

ttctcccctc agcttgagac tgcatgtaaa ctgggatgtg tgaaagcagg aagcaaagct    1860
```

-continued

```
agtgacagct gagaggtcca tgtctgggta gaaccaggcc cacgatgctg cctctcccgt   1920
gttctggagt tcagctgcag ggattctgct gatgtgccca gcaccatcgt tctgtttgtg   1980
cttaaatggc acagcatttg gtcagcacat ctgaaaagga aggtgtgaga agcaaagccc   2040
atggccacgt tcccctgcca gttatgtggc aagacgttcc tcaccctgga gaagttcacg   2100
attcacaatt attcccactc cagggagcgg ccgtacaagt gtgtgcagcc tgactgtggc   2160
aaagcctttg tttccagata taaattgatg aggcatatgg ctacccattc tccccagaaa   2220
tctcaccagt gtgctcactg tgagaagacg ttcaaccgga aagaccacct gaaaaaccac   2280
ttccagaccc acgaccccaa caaaatggcc tttgggtgtg aggagtgtgg gaagaagtac   2340
aacaccatgc tgggctataa gaggcacctg gccctccatg cggccagcag tggggacctc   2400
acctgtgggg tctgtgccct ggagctaggg agcaccgagg tgctactgga ccacctcaaa   2460
gcccatgcgg aagagaagcc ccctagcgga accaaggaaa agaagcacca gtgcgaccac   2520
tgtgaaagat gcttctacac ccggaaggat gtgcgacgcc acctggtggt ccacacagga   2580
tgcaaggact tcctgtgcca gttctgtgcc cagagatttg ggcgcaagga tcacctcacc   2640
cggcatacca agaagaccca ctcacaggag ctgatgaaag agagcttgca gaccggagac   2700
cttctgagca ccttccacac catctcgcct tcattccaac tgaaggctgc tgccttgcct   2760
cctttccctt taggagcttc tgcccagaac gggcttgcaa gtagcttgcc agctgaggtc   2820
catagcctca ccctcagtcc cccagaacaa gccgcccagc ctatgcagcc gctgccagag   2880
tccctggcct ccctccaccc ctcggtatcc cctggctctc ctccgccacc ccttcccaat   2940
cacaagtaca acaccacttc tacctcatac tccccacttg caagcctgcc cctcaaagca   3000
gatactaaag gtttttgcaa tatcagtttg tttgaggact tgcctctgca agagcctcag   3060
tcacctcaaa agctcaaccc aggttttgat ctggctaagg gaaatgctgg taaagtaaac   3120
ctgcccaagg agctgcctgc agatgctgtg aacctaacaa tacctgcctc tctggacctg   3180
tccccccctgt tgggcttctg gcagctgccc cctcctgcta cccaaaatac ctttgggaat   3240
agcactcttg ccctggggcc tggggaatct ttgccccaca ggttaagctg tctggggcag   3300
cagcagcaag aacccccact tgccatgggc actgtgagcc tgggccagct ccccctgccc   3360
cccatccctc atgtgttctc agctggcact ggctctgcca tcctgcctca tttccatcat   3420
gcattcagat aattgatttt taaagggtat ttttcgtatt ctggaagatg ttttaagaag   3480
cattttaaat gtcagttaca atatgagaaa gatttggaaa acgagactgg gactatggct   3540
tattcagtga tgactggctt gagatgataa gagaattctc gaactgcatg tattgtgcca   3600
atctgtcctg agtgttcatg ctttgtacca aatttaatga acgcgtgttc tgtaatcaaa   3660
ctgcaaatat tgtcataacc aacatccaaa atgacggctg ctatatataa gtgtttgtca   3720
tatggaattt aatcgtaagc catgatcata atgttaacta aataacttta tgtggcactg   3780
cctagtaagg gaactatgga aaggtttgga tttctccaaa tctgggagaa ttttcaaaat   3840
aagaaaataa cctttatatg atatactatg actaggctgt gtatttcttt tcagggattt   3900
ttctaccttc agggttggat gtagtttagt tactattacc atagccaacc tgtagtttta   3960
catatacatt ttcttgtgga gcaatagagt tctccatttt acagaagcat tttaaatgta   4020
gtttgaatat tttccacaag atgctgcaat gtgagttatc acttcattta tcttaaagaa   4080
agactaaact ggttgtcagt tacatctgac agaaaaaaaa aaaaaaatca ctgtgtaacc   4140
agggttaagt ggttaaaata atccagggcg tcagtcaaag gcattttgct gactttaata   4200
```

```
ttgattatat ttttaacagg gaatttaagg aaaatattac cggggaatta aaaaatatat   4260

atatattaaa acaagaattt tcctttgccc ctgtccagcc taaacctacc tacctcaagg   4320

ctgcctaagt tcctaagtat tgtttgtaat cacccaataa ataagtgcat ttgtaattca   4380

tcagtcatta ttagctttta ttaaaagaag attacgtttt acaatgtaac tataatctct   4440

tgaatttggt atcttattaa tgagttttaa agatgtaaaa cctaaccttt tttaaagctc   4500

cattgtctta tgtttttaga ggcttttccg taaacatata tcttacatat aataaacttt   4560

caaatcttg caaaaaaaaa aaaaaaaaaa aaaaaaaaaa aaaaaaaaaa aaaaaaaaaa    4620

aaaaaaaaa aa                                                        4632
```

```
<210> SEQ ID NO 27
<211> LENGTH: 2828
<212> TYPE: DNA
<213> ORGANISM: Homo sapiens
<220> FEATURE:
<221> NAME/KEY: mRNA
<222> LOCATION: (1)...(2828)
<223> OTHER INFORMATION: human ZAC zinc finger protein

<400> SEQUENCE: 27

cggcattttg ggacaactgt ttttaacgtt aataaatcac ttaggcgaga tataaattgg     60

ctttgttcca tagcagattt gcctttgtac tagttaagaa aatcctgaaa agctttccct    120

gtaagaggat cagttggttg gaatagcctt ggtaggaaga agccaagttt gataattact    180

tggtgaacgg aaatgctggt ttccaaatgc tcatcagggt tcagtggcac aaagctggct    240

gtagacttgg cttctgtaga tttggtaaaa acgtaaattc ctggggtccc agtgatgctg    300

ttttagtctg tactgatttg ccctgtggcc acccaggaat ctgtattttt aaaagttttc    360

catgctgatt ctaatgcata gccaggttta gtaaccattt aattcagtat tcaacttaga    420

gacttcaacc ttcttgcact gcaaatttga taaatctttg tttatatgaa tctcctttgt    480

tgagtgccaa ctggttattt gctgactttc tttcaattca gaatttgttt taggttctgt    540

tattgcatag atttgcatac ctgttttatg gtattttaat actgttggtt ttaaaaaata    600

ccatttcctc tgagtgctgt tctgaatata ttatgtaagc aattttgtgt gttctttttt    660

ttccacttgc ataaagcagg ggaaaagttg agagtttttc ttaatccagt tgcaagtagg    720

acaaaggata tgagtgttta aagatcatct attaaaatgc atgaaaaaac actagaaaat    780

ctcctgtgca catcgccagt cgtgtgtgtg ctctagaagt gaagttcagg gggtaacata    840

atggaggaat gttttcctag cttcattccc tgacgatgta caaggtctct tctcacaggt    900

ttgaatcttc agacaaactt ctgggaggac tcggtccctg cctcgcagca gatgttccct    960

gtcactcagt agccaatccg ggggacccag gacatgcccc agctatagtg atgcagatta   1020

cctttctgct cctgaatcgc acctgtgcct cagactttct cccctcagct tgagactgca   1080

tgtaaactgg gatgtgtgaa agcaggaagc aaagctagtg acagctgaga ggtccatgtc   1140

tgggtagaac caggcccacg atgctgcctc tcccgtggtc tggagttcag ctgcagggac   1200

tctgctgatt ggcccagcac catcgttctg tttgtgctta aatggcacag catttggtca   1260

gcacatctga aaaggaaggt gtgagaagca aagcccatgg ccacgttccc ctgccagtta   1320

tgtggcaaga cgttcctcac cctggagaag ttcacgattc acaattattc ccactccagg   1380

gagcggccgt acaagtgtgt gcagcctgac tgtggcaaag cctttgtttc cagatataaa   1440

ttgatgaggc atatggctac ccattctccc cagaaatctc accagtgtgc tcactgtgag   1500

aagacgttca accggaaaga ccacctgaaa aaccacctcc agacccacga ccccaacaaa   1560
```

```
atggcctttg ggtgtgagga gtgtgggaag aagtacaaca ccatgctggg ctataagagg   1620

cacctggccc tccatgcggc cagcagtggg gacctcacct gtggggtctg tgccctggag   1680

ctagggagca ccgaggtgct actggaccac ctcaaagccc atgcggaaga gaagccccct   1740

agcggaacca aggaaaagaa gcaccagtgc gaccactgtg aaagatgctt ctacacccgg   1800

aaggatgtgc gacgccacct ggtggtccac acaggatgca aggacttcct gtgccagttc   1860

tgtgcccaga gatttgggcg caaggatcac ctcacccggc ataccaagaa gacccactca   1920

caggagctga tgaaagagag cttgcagacc ggagaccttc tgagcacctt ccacaccatc   1980

tcgccttcat tccaactgaa ggctgctgcc ttgcctcctt tccctttagg agcttctgcc   2040

cagaacgggc ttgcaagtag cttgccagct gaggtccata gcctcaccct cagtccccca   2100

gaacaagccg cccagcctat gcagccgctg ccagagtccc tggcctccct ccacccctcg   2160

gtatcccctg gctctcctcc gccacccctt cccaatcaca agtacaacac cacttctacc   2220

tcatactccc cacttgcaag cctgcccctc aaagcagata ctaaaggttt ttgcaatatc   2280

agtttgtttg aggacttgcc tctgcaagag cctcagtcac ctcaaaagct caacccaggt   2340

tttgatctgg ctaagggaaa tgctggtaaa gtaaacctgc ccaaggagct gcctgcagat   2400

gctgtgaacc taacaatacc tgcctctctg gacctgtccc ccctgttggg cttctggcag   2460

ctgccccctc ctgctaccca aaataccttt gggaatagca ctcttgccct ggggcctggg   2520

gaatctttgc cccacaggtt aagctgtctg gggcagcagc agcaagaacc cccacttgcc   2580

atgggcactg tgagcctggg ccagctcccc ctgcccccca tccctcatgt gttctcagct   2640

ggcactggct ctgccatcct gcctcatttc catcatgcat tcagataatt gatttttaaa   2700

gtgtattttt cgtattctgg aagatgtttt aagaagcatt ttaaatgtca gttacaatat   2760

gagaaagatt tggaaaacga gactgggact atggcttatt cagtgatgac tggcttgaga   2820

tgataaga                                                            2828
```

<210> SEQ ID NO 28
<211> LENGTH: 3975
<212> TYPE: DNA
<213> ORGANISM: Mus musculus
<220> FEATURE:
<221> NAME/KEY: mRNA
<222> LOCATION: (1)...(3975)
<223> OTHER INFORMATION: mouse ZAC1 zinc finger protein

<400> SEQUENCE: 28

```
tgtctcttct cacaggtttg agtcttcaga cttctacaga actccataat atctgcctca     60

cagctggctt tcctgctctc acagaagata cccagctatt gtgctctgga tctctcctgg    120

ctgctaggct gtagcgctgc ctttctggag tcaggctgta gtgactcccc accttctttc    180

tgtctgggct taaatggcac agcagttcct cagcacatct gaagaagaaa gtgtgagaac    240

caaaggccat ggctccattc cgctgtcaaa aatgtggcaa gtccttcgtc accctggaga    300

agttcaccat tcacaattat tcccactcca gggagcgccc attcaagtgc tcgaaggctg    360

agtgtggcaa agccttcgtc tccaagtata agctgatgag acacatggcc acacactcgc    420

cacagaagat tcaccagtgt actcactgtg agaagacatt caaccggaag gaccacctga    480

agaaccacct ccagacccac gatcccaaca agatctccta cgcgtgtgac gattgcggca    540

agaagtacca caccatgctg ggctacaaga ggcacctggc cctgcactcg gcgagcaatg    600

gcgatctcac ctgtggggtg tgcaccctgg agctggggag caccgaggtc ctgctggacc    660
```

-continued

```
acctcaagtc tcacgcggaa gaaaaggcca accaggcacc cagggagaag aaataccagt    720
gcgaccactg tgatagatgc ttctacaccc ggaaagatgt gcgtcgccac ctggtggtcc    780
acacaggatg caaggacttc ctgtgtcagt tctgtgccca gagatttggg cgcaaagacc    840
acctcactcg tcacaccaag aagacccact cccaggagct gatgcaagag aatatgcagg    900
caggagatta ccagagcaat ttccaactca ttgcgccttc aacttcgttc cagataaagg    960
ttgatcccat gcctcctttc cagctaggag cggctcccga gaacgggctt gatggtggct   1020
tgccacccga ggttcatggt ctagtgcttg ctgccccaga agaagctccc caacccatgc   1080
cgccccttgga gcctttggag cctttggagc ctttggagcc tttggagccg atgcagtctt   1140
tggagccttt gcagcctttg gagccgatgc agcctttgga gccaatgcag cctttggagc   1200
cgatgcagcc tttagagcct ttggagcctc tggagccgat gcagcctttg gagccgatgc   1260
agcctttgga gcctatgcag ccaatgctgc caatgcagcc aatgcagcca atgcagccaa   1320
tgcagccaat gctgccaatg cagccaatgc tgccaatgca gccaatgcag ccaatgcagc   1380
caatgctgcc aatgccagag ccgtctttca ctctgcaccc tggcgtagtt cccacctctc   1440
ctcccccaat tattcttcag gagcataagt ataatcctgt tcctacctca tatgccccat   1500
ttgtaggcat gcccgtcaaa gcagatggca aggccttttg caacgtgggt ttctttgagg   1560
aatttcctct gcaagagcct caggcgcctc tcaagttcaa cccatgtttt gagatgccta   1620
tggaggggtt tgggaaagtc accctgtcca aagagctgct ggtagatgct gtgaatatag   1680
ccattcctgc ctctctggag atttcctccc tattggggtt ttggcagctc ccccctccta   1740
ctccccagaa tggctttgtg aatagcacca tccctgtggg gcctggggag ccactgcccc   1800
ataggataac ctgtctggcg cagcagcagc caccgccact gccgccgcca ccaccgctgc   1860
cactgccaca gccactgcca gtgccacagc cactaccaca gccacagatg cagccacagt   1920
ttcagttgca gatccagccc cagatgcagc cccagatgca gctgcagcca ctgcagctgc   1980
agctaccaca gctgctgccg caactgcaac ctcagcagca gcctgatcct gagccagagc   2040
cagagccaga gccagagcca gagccagagc cagagccgga accggaaccg gagccagagc   2100
cagagccaga accagagcca gaggaagaac aggaagaggc agaagaagag gcagaggaag   2160
gagcagagga aggagcagaa ccagaggcac aggcagaaga agaggaagag gaagaggaag   2220
cggaagagcc acagccagaa gaagcccaaa tagcagtgag tgctgtgaat ctgggccagc   2280
ccccccctacc cccaactccc catattttca cagctggctc caacactgct atcctgcccc   2340
atttccatca cgcatttaga taaattggtt tttaagaggg tgcttctctt gtgggagatg   2400
ttttaaacat cagttacagt ttgaggagaa gcattggaaa acaggaatgg ggttttagct   2460
tatttgtcat aagtagcttg agaaaaagaa ttctctaact gcatgcgttg tgccaatata   2520
tacccttagt attcatgctt cctaccaaat ttagtgagcg tgtgtgcatt ctgtaatcaa   2580
actgcaaata ttatcatatt atcctattat tacccttgta ttattaccct catattatta   2640
ccctcatatt atcctcatta tcttataatc acgtgattac gtgataagat ccaaaacatg   2700
agctgctatt ttgtaaatat cgtgttgagt gtaagctgtt gtagtgatgt tagctatgta   2760
actgtgtgta gcctaggaag gggatgatgg taaagtttgg aattctccaa cttggaaggt   2820
gtttttaaga gaaggggata atctttgtat ggcgtttata actaggctgt gtgtttcttt   2880
tcagggactc gtctataaga aatggacagt ttagttcctc ttcttgttag cttactctgt   2940
agtttcttct tcttgttgcc cattgtgtag ctttatagag tgtgacgcta ttgatgtctc   3000
catttttttaa agtgaattta aatgtactgt tcaatatttt tcatgtgatg ttgttccaat   3060
```

```
gtgagttacg acttcattta tcttaaagac aaaactggtt gtcagtcata tctgacagaa   3120

gaaagaaatc actgtgtaac caagtcaagt ggccaactaa ttgaagaaga atcaatcaaa   3180

gtgtttgtgg actgtgatac tcattatgtt tttaacagga atttaagaaa atgtactgga   3240

atttaaaaaa agcataagta tattagataa gaattttctt tgcctagctt aacctactac   3300

ttaagctgct taagttctga agtattgttt gtaatcacca atagaaaagt gtatctgtag   3360

atgatcaatt taagtcattg ttagtttgta tcccaagagg attgtgtttt gcaatgtaac   3420

ctacttgtaa tctcccttga taccttgtta atcgattttg aagtgtaaac ctaacctttg   3480

aagactctgt atttccttct tgagactgta tcccccagat atatctccta acctttgaag   3540

actctgtatt tcatttttga gactgtattc cccaggattt atctcctaac ctttgtagac   3600

tctgtatttc gtttttgaga ctgtctttcc cagcatatat ctcctgacct ttgacaactc   3660

tgtatttcgt ttttgagact gtattcccca gcatatatct cctgaccttt gaagaccctg   3720

cattttgttt ttgagatgga attcaacagc atatatctcc taatctttga tgactctgta   3780

ttttgttttt gagattgtat tccccagcat atatctccta acctttgaag actctgtatt   3840

catttttga gactgtattc cccaacgtgt atctcctaac ctttgaataa tctccacttt    3900

tttttgaga ctgtattccc cagcatatat ctcctaacct ttgactctgt actttgtttt    3960

gagagtgta ttccc                                                     3975
```

```
<210> SEQ ID NO 29
<211> LENGTH: 536
<212> TYPE: DNA
<213> ORGANISM: Homo sapiens

<400> SEQUENCE: 29

tctgaaattt ttattcattt catatattag gatttagctg gttacaggtc acttttctaa     60

tgacatcaag aactactcaa agacacattg tgtgtgtata tatatataca cacacacaca    120

cacacacaca caatatatat acacacacat atatatatgt gtgtgtatac atatatctaa    180

agacctataa aaccatgttt tgtgggtttt tttttttttt ggtatttcta cttttcccat    240

agtatttcca tacctcacca gtgctaggta tggtactatc ctatgtatat tggatacctc    300

atgtttcttg ataatttaag aaaattcaat ttatgctgct ggtatatctt ccagtaatat    360

aaaatttca gaattttaag agtttttcag gtagaaaaat ttagcaaaac caaaagagaa     420

atggagggaa aaaaaggtct aagaaaaaca taaaagccag tggagtatgc taatgggaaa    480

aaaattaaca taaggcttca caatttacaa tggctggagg aaataaaact ggatgg        536
```

```
<210> SEQ ID NO 30
<211> LENGTH: 2059
<212> TYPE: DNA
<213> ORGANISM: Homo sapiens
<220> FEATURE:
<221> NAME/KEY: mRNA
<222> LOCATION: (1)...(2059)
<223> OTHER INFORMATION: putative nucleotide binding protein,
      estradiol-induced (E2IG3)

<400> SEQUENCE: 30

gcggccgcca agcgatccct gctccgcgcg acactgcgtg cccgcgcacg cagagaggcg     60

gtgacgcact ttacggcggc acgtaagtgc gtgacgctcg tcagtggctt cagttcacas    120

gtggcgccmg sasgmrggtt gctgtgtttg tgcttccttc tacagccaat atgaaaaggc    180

ctaagttaaa gaaagcaagt aaacgcatga cctgccataa gcggtataaa atccaaaaaa    240
```

-continued

```
aggttcgaga acatcatcga aaattaagaa aggaggctaa aaagcagggt cacaagaagc    300
ctaggaaaga cccaggagtt ccaaacagtg ctccctttaa ggaggctctt cttagggaag    360
ctgagctaag gaaacagagg cttgaagaac taaaacagca gcagaaactt gacaggcaga    420
aggaactaga aaagaaaaga aaacttgaaa ctaatcctga tattaagcca tcaaatgtgg    480
aacctatgga aaaggagttt gggctttgca aaactgagaa caaagccaag tcgggcaaac    540
agaattcaaa gaagctgtac tgccaagaac ttaaaaaggt gattgaagcc tccgatgttg    600
tcctagaggt gttggatgcc agagatcctc ttggttgcag atgtcctcag gtagaagagg    660
ccattgtcca gagtggacag aaaaagctgg tacttatatt aaataaatca gatctggtac    720
caaaggagaa tttggagagc tggctaaatt atttgaagaa agaattgcca acagtggtgt    780
tcagagcctc aacaaaacca aaggataaag ggaagataac caagcgtgtg aaggcaaaga    840
agaatgctgc tccattcaga agtgaagtct gctttgggaa agagggcctt tggaaacttc    900
ttggaggttt tcaggaaact tgcagcaaag ccattcgggt tggagtaatt ggtttcccaa    960
atgtggggaa aagcagcatt atcaatagct taaaacaaga acagatgtgt aatgttggtg   1020
tatccatggg gcttacaagg agcatgcaag ttgtcccctt ggacaaacag atcacaatca   1080
tagatagtcc gagcttcatc gtatctccac ttaattcctc ctctgcgctt gctctgcgaa   1140
gtccagcaag tattgaagta gtaaaaccga tggaggctgc cagtgccatc ctttcccagg   1200
ctgatgctcg acaggtagta ctgaaatata ctgtcccagg ctacaggaat tctctggaat   1260
tttttactat gcttgctcag agaagaggta tgcaccaaaa aggtggaatc ccaaatgttg   1320
aaggtgctgc caaactgctg tggtctgagt ggacaggtgc ctcattagct tactattgcc   1380
atccccctac atcttggact cctcctccat attttaatga gagtattgtg gtagacatga   1440
aaagcggctt caatctggaa gaactggaaa agaacaatgc acagagcata agagccatca   1500
agggccctca tttggccaat agcatccttt tccagtcttc cggtctgaca aatggaataa   1560
tagaagaaaa ggacatacat gaagaattgc caaaacggaa agaaaggaag caggaggaga   1620
gggaggatga caaagacagt gaccaggaaa ctgttgatga agaagttgat gaaaacagct   1680
caggcatgtt tgctgcagaa gagacagggg aggcacttct gaggagacta cagcaggtga   1740
acagtctaca aggtctttta tcttggataa aatcattgaa gaggatgatg cttatgactt   1800
cagtacagat tatgtgtaac agaacaatgg ctttttatga tttttttttt taacatttta   1860
agcagactgc taaactgttc tctgtataag ttatggtatg catgagctgt gtaaattttg   1920
gaatatgta ttatattaaa accaggcaac ttggaatccc taaattctgt aaaaagacaa    1980
tcatctcat tgtgagtgga agtagttatc tggaataaaa aaagaagata cctattgaaa    2040
aaaaaaaaa aaaaaaaaa                                                 2059
```

<210> SEQ ID NO 31
<211> LENGTH: 1943
<212> TYPE: DNA
<213> ORGANISM: Mus musculus
<220> FEATURE:
<221> NAME/KEY: mRNA
<222> LOCATION: (1)...(1943)
<223> OTHER INFORMATION: mouse mrg-1

<400> SEQUENCE: 31

```
cctggcggtc ttgcggagtg ctagggcagc ggaggaaaag aaaagggaac ggctcggaat     60
ttgctccagc ggctgctgca agacctcggc gccaacctcg caccgggagc gcctcacagc    120
```

-continued

```
ccatcggctg tccctctatg tgctgctgag ccggtcctgg actcgacgag cccgccttcg    180

gtgttccgag cagaaatcgc aaagacggaa ggactggaaa tggcagacca tatgatggcc    240

atgaaccacg ggcgcttccc cgacggcacc aacgggctgc accaccaccc tgcccaccgc    300

atgggcatgg ggcagttccc gagcccgcat catcaccagc agcagcagcc ccagcacgcc    360

ttcaacgccc tcatgggcga gcacatacac tacggcgcgg gcaacatgaa tgcaacgagc    420

ggcatcaggc acgccatggg gccggggact gtgaacgggg ggcacccccc gagcgctctg    480

gccccggccg ccaggtttaa caactcccag ttcatgggtc cccggtggc cagccaggga    540

ggctccctgc cggccagcat gcagctgcag aagctcaaca accagtattt caaccatcac    600

ccctaccccc acaaccacta catgcctgat ttgcacccca ctgcaggcca ccagatgaac    660

gggacaaacc agcacttccg agattgcaac cccaagcaca gcggaggcag cagcacccct    720

ggcggtgcgg gtggcagcgg cacccccggc ggctccggcg gcacctcggg cggcgcgggt    780

ggcagcagcg cgggcggcac gtgcggtggc agcaccatgc ccgcctcggt ggctcacgtc    840

cccgcggcaa tgctgccgcc caatgtcata gacactgatt tcatcgacga ggaagtgctt    900

atgtccttag tgatagaaat gggtttggac cgcatcaagg agctgcccga actctggctg    960

gggcaaaatg agtttgattt tatgacggac ttcgtgtgca agcagcagcc cagcagagtc   1020

agctgttgac tcggttaacc tcgcaggcgg aaacaaatca ccctccccac cccaccccca   1080

cccccaactt cttcggtgtg aattaaaaaa aaaacaaaaa aacaaacatt cccttagacg   1140

cagtatctcg cttttcagat cctgaaaggg ttgagaacct ggaaacaaag taaactataa   1200

acttgtacaa attggtttaa aaaaaaaaaa agattgctgc cactttttcc tattcttgtt   1260

tcgtttttg tagccttgac attcacctcc cttatgtagt tgaaatatct agctaacttg   1320

gctctttttt gttgtttgtt tttactcctt tatttcctca ctttatttcc tcactttctc   1380

ccgtgctcaa ctgttagata ttaagcttgg caaactgctt aatcttgtgg attttgtaga   1440

tggtttcaaa tgactgcgct gctttcagat tcatgagtga aaggaaacat tgcatttgtt   1500

ggctgcatga tctttgaagg gcagatatta ctgcacaaac tgccatctcg cttcattttt   1560

tttaactatg cattcgagta cagacttaag ttttcaaata tgctaaactg gaagattaaa   1620

catgtgggcc aaaccgttct ggatcaggaa aagtcatacc gttcactttc aagttggctg   1680

tctcccctcc cccatatgta cagacaataa tagggtgtgg aatgtcgtca gtggcaaaca   1740

tttcacagat tttatttttg tttctgtctt caacattttt gacactgtgc taatagttat   1800

attcagtaca tgaaaagata ctactgtgtt gaaagctttt taggaaattt tgacagtatt   1860

tttgtacaaa acattttttt gagaaaatac ttgttaattt attctatttt aatttgccaa   1920

tgtcaataaa aagttaagaa ata                                              1943
```

<210> SEQ ID NO 32
<211> LENGTH: 6324
<212> TYPE: DNA
<213> ORGANISM: Homo sapiens
<220> FEATURE:
<221> NAME/KEY: mRNA
<222> LOCATION: (1)...(6324)
<223> OTHER INFORMATION: human p35srj

<400> SEQUENCE: 32

```
atcaagtta acatgaggcc agtaggagaa gccctaatcc aaaaggacta gagtccttgt      60

aaaagggga actttggaca cagagataca catacagggg ggcgggggt ggaaaacgtc      120

catgaagat gaaggtgggg atcagtgtga tgcatctaca agtcaaggga caccaaagat     180
```

-continued

```
gccgggaaa ccaccaaaag ccaggaaaga gacacggaat agattctctc tcacggtctt    240
agaaccaac cctgccaaca acttggcctt gtacctctag cctccagaac tgtgagacaa    300
aatgttttg ttgtttaaag cttgatcagc cttaagtttg tattagactg gtgcaaaagt    360
attacagtt ttcgccattg ctttcaatgg caaaaatcac aattactttt gcaccaacct    420
aatagtact gtgttatggc agctctggga aatgaataca accattcagt gctgtgaggg    480
cacagacag atcacttgct cgctcaccca ggttcacggg ataaaccctg gttatacgga    540
cttctggga gccctgggtt actgtaagtg ccccctaact ggactccctg tttcctgtct    600
actttctct aaccattctc cacagcactg ccctgatctt tctaaaatcc aaatctttcc    660
atctcatgg cttcacaagc ttttacctgc ctcccaatgt ctttgggata cagcaaaatt    720
ctcagcttg aggccacaat gcccttggca tccggcccca gcatatttct ccaaccttat    780
tctctcatc tttgcattca ctccctagcc atacattttc taccccactc ctaatgggac    840
aaacttcca ttcatcctga ggcctccact tagtcaccat ctccaccgga aagccttccc    900
aagcaccca ggagggggt aggtgtccct cctatgtgct ctccaaagcc ctttccttca    960
tgcctttgt ggcatttatc acagtgtgtt caaggcctgt ttgtcagttt tctccctgtg   1020
ccatgagtt cctatcttgt ttgtatctcc aggcaccaag aaagcacttg gcacttggag   1080
acattcagt ggacggatga gaataaatga acaaagcatg ccatgttcca accagctggt   1140
ccagaacta ttttgttctc ctttaaggga tgggggatgg gcaggtgacc tttccaggga   1200
ttcccaata gtaggtagaa ccactggagc tggatggagc tccacctttc cttagtggtt   1260
caagaggaa tttagattag acattcaaaa gctgtttctt gtgtcgaaag acacttgcag   1320
acaaagaag ggaaagtaaa caatcccgcg atttttcagg ttgggtttta ccaatatttt   1380
gaatctgtt tttttatagg aagtggcccc ttcaggtatc caagcctctg atacggtaaa   1440
tgcatgtcc tgacctacag gtaaaggtgg tgggaggtta ggagaatagg gaattgttgc   1500
actaacaat gcaatgtgtc atgtgcccgt atctctaaaa agtaaatatt tttgaggttt   1560
aaaattatt tgcctgcacg gtttgccgga gagcctggaa gaggaaagaa gacaagacac   1620
aagtaacaa catttacaaa aatatgcctg actaggaaaa gacagagggg tcatagacga   1680
aataatcag gattgggtct cttttgcaaa ttcctgaacg gggaaatgta tcagaatttc   1740
agtcctcaa gaaacagggc ctttaaaagt cttgtgtgca agaaggggga aaaagacgag   1800
gggggcgg ggaggcggac tcgctcttcg cagcaggaag tcttcaatgg ctatcgagtt   1860
tgaagaaac aactgcccag aagtccttat tcggagcgct aaactcgatt ttaccacata   1920
agagcaatg taaaagctca gaacagcccc atcatggtgt tggggaaaca actcggcttc   1980
ccatgtgag aaagccagag agctccgact tggtagtagc ccagacctgt gttaggggtt   2040
tatttgcaa gtcaatgaac caaacgggcg accaggctcg ttgtgccgcg ttgtggaagc   2100
aggttatta ttatcgccca ttgccccact gaacaatttc actgaaaagg aagagtccca   2160
ccgtgtgtg tgcgcgtggt gccatacggg acgtgcagct acgtgcccac ctccagaacg   2220
ctttattta caaagcgatt accacgttat ctatttgttt tccttttcca gcaagagcag   2280
cttactcag ccctcaaatt tcttaattac aaacccgttt gcttctaaat caaccccaaa   2340
cgtcaggca gagcccggag ggaggctctg caagtttgta cacaccccca cctcccggat   2400
cagggcaac agcagaagca agtaactgtg tatgtgcaaa aaggtggatc tggggacgag   2460
atcgctgag tttgtttaca gagcagagac gcctcagctc ggatgccaaa gctaccaaga   2520
```

-continued

```
ctgcaaacg caaacttagc agaagcacac gtaccccggg agcggcaggc gggcccgaaa   2580
cgcggactg gaattccagg gcgcgggagc gggggtggcc gggccctcga gcgcgctccg   2640
ccacctgca gcggctgccc ctccccgccc ccagctcctg tccttgaaag gagtggagga   2700
aaaaatgca tctacaagcg gtgatctaga gtaggtctac ccactgcccg tatgaaaaca   2760
aaaggcaca gcctaggaag gcgcgctcag gaaagggcgc attatttgtc cgggtcttta   2820
aacccaact cgaggaagca cagccattct tcgctgcctg tggaagcttt tgcaaaaccg   2880
ggaggcaca agggcactct ggagggcggg gggcgctggg cgagtcccct tttcccgtag   2940
gagcggggc agatcgctag gtgaaccgag tgagaaagct gggggtgggg tagatccagc   3000
tgagggggg cggtgagctc tcctcgtggc tatcccggca ggctctacct tcgggcgggg   3060
ggcaggggga ggattttccc cctgcctcgg gggtggctga gccaacctcg cgtttctggg   3120
cgggaagaa accagagtcg gggggcgacg gggcgactgg gcggcccccg ggccccgcag   3180
ctctgcagc acgtgccgcg ggcggcgggg acgcggctcc gggacccggt ccagggtgtt   3240
gcggtgttc cggaatccgc gtcttggcgc cgcccgccct ggaggctctc gctccgcctt   3300
ccgaaatgc ctatattaac tgtggccaaa gccctaagaa acacagctca ttgttggcag   3360
tgccgggcg gtcctgccga gctgtgaggg caacggaggg gaaataaaag ggaacggctc   3420
gaatctgcc ccagcggccg ctgcgagacc tcggcgccga catcgcgaca gcgaagcgct   3480
tgcacgcca ggaaggtccc ctctatgtgc tgctgagccg gtcctggacg cgacgagccc   3540
ccctcggtc ttcggagcag aaatcgcaaa aacggaaggt aagcgcgacg ggcgaagctg   3600
ctggggctc ttgccagccc agtcctccga gggcagggtt tgcccggagg aagaacgtga   3660
gcgaaactg gggaataaca acaggatgtg ctacaacagg atgaggaggg ctgatttaat   3720
cctgaagtt cgcagcaggg ctacggggca cttcctttta taggccactt cggggagcaa   3780
gggggtgtg ggctcgggtc cccccgcccg atcgcagggg aaggggctgt ttgtgcagcg   3840
ccggctgtg ttatgagtgg tagctcttcc gtggtggcta gcccgggtgc acaggctgtt   3900
gtgggatct tgggggtggt ggttcgcagc cgacgtgcgc ccgggaatcc tggggggcag   3960
ggcgagcaa aagtggggtg cgctgtggtg ggcgacacgt gtggcgcggg tctcattatc   4020
gccctttc acttccagga ctggaaatgg cagaccatat gatggccatg aaccacgggc   4080
cttccccga cggcaccaat gggctgcacc atcaccctgc ccaccgcatg ggcatggggc   4140
gttcccgag cccccatcac caccagcagc agcagcccca gcacgccttc aacgccctaa   4200
gggcgagca catacactac ggcgcgggca acatgaatgc cacgagcggc atcaggcatg   4260
gatggggcc ggggactgtg aacggagggc accccccgag cgcgctggcc cccgcggcca   4320
gtttaacaa ctcccagttc atgggtcccc cggtggccag ccagggaggc tccctgccgg   4380
cagcatgca gctgcagaag ctcaacaacc agtatttcaa ccatcacccc taccccccaca   4440
ccactacat gccggatttg caccctgctg caggccacca gatgaacggg acaaaccagc   4500
cttccgaga ttgcaacccc aagcacagcg gcggcagcag cacccccggc ggctcgggcg   4560
cagcagcac ccccggcggc tctggcagca gctcgggcgg cggcgcgggc agcagcaaca   4620
cggcggcgg cagcggcagc ggcaacatgc ccgcctccgt ggcccacgtc cccgctgcaa   4680
gctgccgcc caatgtcata gacactgatt tcatcgacga ggaagttctt atgtccttgg   4740
gatagaaat gggtttggac cgcatcaagg agctgcccga actctggctg gggcaaaacg   4800
gtttgattt tatgacggac ttcgtgtgca aacagcagcc cagcagagtg agctgttgac   4860
cgatcgaaa ccccggcgaa agaaatcaaa cccccaactt cttcggcgtg aattaaaaga   4920
```

acattccct tagacacagt atctcacttt tcagatcttg aaaggtttga gaacttggaa 4980 caaagtaaa ctataaactt gtacaaattg gttttaaaaa aaattgctgc cacttttttt 5040 cctgttttt gtttcgtttt tgtagccttg acattcaccc acctccctta tgtagttgaa 5100 tatctagct aacttggtct ttttcgttgt ttgtttttac tcctttccct cactttctcc 5160 gtgctcaac tgttagatat taatcttggc aaactgctta atcttgtgga ttttgtagat 5220 gtttcaaat gactgaactg cattcagatt tacgagtgaa aggaaaaatt gcattagttg 5280 ttgcatgaa cttcgaaggg cagatattac tgcacaaact gccatctcgc ttcatttttt 5340 aactatgca tttgagtaca gactaatttt taaaatatgc taaactggaa gattaaacag 5400 tgtgggcca aactgttctg gatcaggaaa gtcatactgt tcactttcaa gttggctgtc 5460 cccccgccg ccccccccca cccccatatg tacagatgat aatagggtgt ggaatgtcgt 5520 agtggcaaa catttcacag atttttattt tgtttctgtc ttcaacattt ttgacactgt 5580 ctaatagtt atattcagta catgaaaaga tactactgtg ttgaaagcct tttaggaaat 5640 ttgacagta tttttgtaca aaacattttt ttgaaaaaat acttgttaat ttattctatt 5700 taatttgcc aatgtcaata aaaagttaag aaataacttg ttttctagaa gtcatttggg 5760 gtggttgtt ccctttggtg gctttttttcc ccccgtcttt gagttgaaca ctattgatga 5820 agtaagcat tccaaaggat aaattacagg acactaaaac aggtcatgat gagcttaagc 5880 gagagcagg atttaacata attggcataa tgcttcattg ttatcattgt aacatgcctc 5940 tggtgtgct ttaatcaaaa gctgcaaagt tgtcactgct tttttttttt tcttaattgc 6000 atcatatca agtgtactcc agagttagaa aggtttgcaa tactcaacat tatctttttc 6060 atgggcagg aggcaaaaaa aatcaagtgt ttctgtttat acctgattca actacttaaa 6120 agaggtaga ttggaataat acactgattg attgatgggt ggcattaaat ataaatctac 6180 tttatctcc agtgatgaga gttttatttc tcagcaaaag tgccaaggat aggtacatat 6240
tttctagcgt aatctctgaa acatgtctga ctggttata gttctgagaa gaagagcgaa 6300 atccccccttg aagcctttgt ccca

<210> SEQ ID NO 33
<211> LENGTH: 1919
<212> TYPE: DNA
<213> ORGANISM: Homo sapiens
<220> FEATURE:
<221> NAME/KEY: mRNA
<222> LOCATION: (1)...(1919)
<223> OTHER INFORMATION: human p35srj (MRG1)

<400> SEQUENCE: 33
gtcctgccga gctgtgaggg caacggaggg gaaataaaag ggaacggctc cgaatctgcc 60
ccagcggccg ctgcgagacc tcggcgccga catcgcgaca gcgaagcgct ttgcacgcca 120
ggaaggtccc ctctatgtgc tgctgagccg gtcctggacg cgacgagccc gccctcggtc 180
ttcggagcag aaatcgcaaa aacggaagga ctggaaatgg cagaccatat gatggccatg 240
aaccacgggc gcttccccga cggcaccaat gggctgcacc atcaccctgc ccaccgcatg 300
ggcatggggc agttcccgag cccccatcac caccagcagc agcagcccca gcacgccttc 360
aacgccctaa tgggcgagca catacactac ggcgcgggca acatgaatgc cacgagcggc 420
atcaggcatg cgatggggcc ggggactgtg aacggagggc acccccccgag cgcgctggcc 480 cccgcggcca ggtttaacaa ctcccagttc atgggtcccc cggtggccag ccagggaggc 540

-continued

```
tccctgccgg ccagcatgca gctgcagaag ctcaacaacc agtatttcaa ccatcacccc    600

tacccccaca accactacat gccggatttg caccctgctg caggccacca gatgaacggg    660

acaaaccagc acttccgaga ttgcaacccc aagcacagcg gcggcagcag cacccccggc    720

ggctcgggcg gcagcagcac ccccggcggc tctggcagca gctcgggcgg cggcgcgggc    780

agcagcaaca gcggcggcgg cagcggcagc ggcaacatgc ccgcctccgt ggcccacgtc    840

cccgctgcaa tgctgccgcc caatgtcata gacactgatt tcatcgacga ggaagttctt    900

atgtccttgg tgatagaaat gggtttggac cgcatcaagg agctgcccga actctggctg    960

gggcaaaacg agtttgattt tatgacggac ttcgtgtgca aacagcagcc cagcagagtg   1020

agctgttgac tcgatcgaaa ccccggcgaa agaaatcaaa cccccaactt cttcggcgtg   1080

aattaaaaga aacattccct tagacacagt atctcacttt tcagatcttg aaaggtttga   1140

gaacttggaa acaaagtaaa ctataaactt gtacaaattg gttttaaaaa aaattgctgc   1200

cacttttttt tcctgttttt gtttcgtttt tgtagccttg acattcaccc acctccctta   1260

tgtagttgaa atatctagct aacttggtct tttcgttgt ttgtttttac tcctttccct   1320

cactttctcc agtgctcaac tgttagatat taatcttggc aaactgctta atcttgtgga   1380

ttttgtagat ggtttcaaat gactgaactg cattcagatt tacgagtgaa aggaaaaatt   1440

gcattagttg gttgcatgaa ctttgaaggg cagatattac tgcacaaact gccatctcgc   1500

ttcatttttt taactatgca tttgagtaca gactaatttt taaaatatgc taaactggaa   1560

gattaaacag atgtggccca aactgttctg gatcaggaaa gtcatactgt tcactttcaa   1620

gttggctgtc ccccccgccg ccccccccca cccccatatg tacagatgat aatagggtgt   1680

ggaatgtcgt cagtggcaaa catttcacag attattttgt ttctgtcttc aacatttttg   1740

acactgtgct aatagttata ttcagtacat gaaaagatac tactgtgttg aaagcctttt   1800

aggaaatttt gacagtattt ttgtacaaaa cattttttttg aaaaaatact tgttaattta   1860

ttctatttta atttgccaat gtcaataaaa agttaagaaa taaaaaaaaa aaaaaaaaa    1919
```